(12) United States Patent
Krantz et al.

(10) Patent No.: US 7,048,818 B2
(45) Date of Patent: May 23, 2006

(54) HOOK AND LOOP FASTENING

(75) Inventors: K. Theodor Krantz, Amherst, NH (US); Howard A. Kingsford, Amherst, NH (US); Martin I. Jacobs, Bedford, NH (US); William H. Shepard, Amherst, NH (US); William Clune, Concord, NH (US); Paul R. Erickson, New Boston, NH (US); John L. Boucher, Manchester, NH (US); Clinton Dowd, Goffstown, NH (US)

(73) Assignee: Velcro Industries B.V. (AN)

( * ) Notice: Subject to any disclaimer, the term of this patent is extended or adjusted under 35 U.S.C. 154(b) by 28 days.

(21) Appl. No.: 09/808,395

(22) Filed: Mar. 14, 2001

(65) Prior Publication Data

US 2002/0022108 A1 Feb. 21, 2002

Related U.S. Application Data

(60) Provisional application No. 60/242,877, filed on Oct. 24, 2000, and provisional application No. 60/189,125, filed on Mar. 14, 2000.

(51) Int. Cl.
*B32B 3/10* (2006.01)

(52) U.S. Cl. ..................... 156/66; 156/244.25; 156/245
(58) Field of Classification Search .................. 156/66, 156/160, 229, 242, 245, 244.11, 244.25
See application file for complete search history.

(56) References Cited

U.S. PATENT DOCUMENTS 679,918 A 8/1901 Shears (Continued)

FOREIGN PATENT DOCUMENTS

CN 1153701 A 11/1996

(Continued)

OTHER PUBLICATIONS

PCT International Search Report, International Appln. No. PCT/US01/08100 mailed Sep. 26, 2001 (7 pp).

(Continued)

*Primary Examiner*—Gladys JP Corcoran
(74) *Attorney, Agent, or Firm*—Fish & Richardson P.C.

(57) ABSTRACT

Fastenings, including stretchy or flexible "zebra-like" and "leopard-like" appearing materials, are disclosed having spaced bands or a distribution islands of molded loop-engageable hooks or molded pre-forms for hooks, between which are bands or regions of different character. Molding is by rigid molds filled from the base region of the stems. In embodiments, linear bands or islands of fastener elements are themselves inextensible in the direction of their extent and comprise multiple rows of fastener elements. For ease of forming a uniform, elastically stretchy or flexible product, the bands or islands of fastener elements extend in the machine direction during manufacture. Embodiments shown employ a widthwise continuous carrier of uniform character to which multiple spaced bands or islands of hooks have their molded stems in situ bonded, and in other embodiments, over-lapping margins of the bases of hook bands are in situ laminated to surface structure of adjacent bands of carrier using a laminating nip in which one of the rolls is a mold roll. For a preferred mode of manufacture of an elastically stretchy product, stretchy carrier material is stretchy only in the widthwise (cross-machine) direction. In composite hook and loop fastener products, the bands or regions of material between adjacent bands or islands of hooks comprise loop-engageable material, that is uniform in construction widthwise, the loop-forming material itself being an elastically stretchable or a flexible component. In useful product categories, the hook bands or islands and intervening regions of material have importantly different width ranges. Novel elastically stretchable and flexible loop-defining materials, and their methods of manufacture are shown. In situ lamination of hook, bands or islands on surfaces of materials held in a planar orientation or presenting a planar surface are also shown, flexible materials on tenter frames and rigid materials.

20 Claims, 43 Drawing Sheets

U.S. PATENT DOCUMENTS

| | | |
|---|---|---|
| 697,637 A | 4/1902 | Lee |
| 1,920,808 A | 8/1933 | Sander |
| 2,004,959 A | 6/1935 | Morin et al. |
| 2,026,904 A | 1/1936 | Morin et al. |
| 2,170,421 A | 8/1939 | Morin et al. |
| 2,367,690 A | 1/1945 | Purdy |
| 2,913,803 A | 11/1959 | Dodds |
| 3,000,384 A | 9/1961 | Piers, Jr. |
| 3,026,874 A | 3/1962 | Stevens |
| 3,086,529 A | 4/1963 | Munz et al. ............... 128/327 |
| 3,113,803 A | 12/1963 | Struble et al. |
| 3,147,528 A | 9/1964 | Erb |
| 3,152,381 A | 10/1964 | Priester, Jr. et al. |
| 3,194,234 A | 7/1965 | Duckman et al. |
| 3,214,323 A | 10/1965 | Russell et al. |
| 3,235,438 A | 2/1966 | Wisotzky |
| 3,312,583 A | 4/1967 | Rochlis |
| 3,334,626 A | 8/1967 | Schimmel |
| 3,341,386 A | 9/1967 | White et al. |
| 3,347,735 A | 10/1967 | Steinman |
| 3,372,444 A | 3/1968 | Mathison |
| 3,387,345 A | 6/1968 | Savoir |
| 3,442,270 A | 5/1969 | Steinman |
| 3,464,094 A | 9/1969 | Mates |
| 3,520,306 A | 7/1970 | Gardner et al. |
| 3,555,630 A | 1/1971 | Wylde |
| 3,594,863 A | 7/1971 | Erb |
| 3,594,865 A | 7/1971 | Erb |
| 3,608,035 A | 9/1971 | Frohlich |
| 3,665,921 A | 5/1972 | Stumpf |
| 3,665,922 A | 5/1972 | Skora |
| 3,674,618 A | 7/1972 | Spann |
| 3,683,921 A | 8/1972 | Brooks et al. |
| 3,694,537 A | 9/1972 | Fairbanks |
| 3,694,867 A | 10/1972 | Stumpf |
| 3,705,065 A | 12/1972 | Stumpf |
| 3,708,361 A | 1/1973 | Stumpf |
| 3,708,833 A | 1/1973 | Ribich et al. |
| 3,720,578 A | 3/1973 | Heling |
| 3,752,619 A | 8/1973 | Menzin |
| 3,758,657 A | 9/1973 | Menzin et al. |
| 3,762,000 A | 10/1973 | Menzin et al. |
| 3,822,162 A | 7/1974 | Stumpf |
| 3,863,640 A | 2/1975 | Haverstock |
| 3,880,161 A | 4/1975 | Fossel |
| 3,945,781 A | 3/1976 | Doleman |
| 3,954,105 A | 5/1976 | Nordby et al. |
| 3,968,803 A | 7/1976 | Hyman |
| 4,056,593 A | 11/1977 | de Navas Albareda |
| 4,074,397 A | 2/1978 | Rosin |
| 4,077,410 A | 3/1978 | Butterworth et al. |
| 4,088,136 A | 5/1978 | Hasslinger et al. |
| 4,097,634 A | 6/1978 | Bergh |
| 4,116,892 A | 9/1978 | Schwarz |
| 4,149,540 A | 4/1979 | Hasslinger |
| 4,154,885 A | 5/1979 | Tecl et al. |
| 4,154,889 A | 5/1979 | Platt |
| 4,181,127 A | 1/1980 | Linsky et al. |
| 4,207,885 A | 6/1980 | Hampton et al. |
| 4,223,059 A | 9/1980 | Schwarz |
| 4,247,967 A | 2/1981 | Swinton |
| 4,258,097 A | 3/1981 | Benedyk |
| 4,261,944 A | 4/1981 | Hufnagel et al. |
| 4,263,906 A | 4/1981 | Finley |
| 4,295,251 A | 10/1981 | Tatham et al. |
| 4,320,167 A | 3/1982 | Wishman |
| 4,363,845 A | 12/1982 | Hartmann |
| 4,377,889 A | 3/1983 | Tatham et al. |
| 4,379,189 A | 4/1983 | Platt |
| 4,389,442 A | 6/1983 | Pickens, Jr. et al. |
| 4,391,866 A | 7/1983 | Pickens, Jr. et al. |
| 4,399,816 A | 8/1983 | Spangler |
| 4,418,104 A | 11/1983 | Kiyomura et al. |
| 4,424,250 A | 1/1984 | Adams et al. |
| 4,446,189 A | 5/1984 | Romanek |
| 4,451,314 A | 5/1984 | Knoke et al. |
| 4,451,315 A | 5/1984 | Miyazaki |
| 4,465,486 A | 8/1984 | Hill |
| 4,470,410 A | 9/1984 | Elliott |
| 4,490,425 A | 12/1984 | Knoke et al. |
| 4,522,853 A | 6/1985 | Szonn et al. |
| 4,536,439 A | 8/1985 | Forsten |
| 4,541,154 A | 9/1985 | Ito et al. |
| 4,569,348 A | 2/1986 | Hasslinger |
| 4,592,118 A | 6/1986 | DeWoskin |
| 4,600,605 A | 7/1986 | Nakai et al. |
| 4,600,618 A | 7/1986 | Raychok, Jr. et al. |
| 4,615,084 A | 10/1986 | Erb |
| 4,624,116 A | 11/1986 | Rogers |
| 4,641,643 A | 2/1987 | Greer |
| 4,645,699 A | 2/1987 | Neveu |
| 4,654,246 A | 3/1987 | Provost et al. |
| 4,672,722 A | 6/1987 | Malamed |
| 4,705,710 A | 11/1987 | Matsuda |
| 4,706,914 A | 11/1987 | Ground |
| 4,709,695 A | 12/1987 | Kohn et al. |
| 4,732,146 A | 3/1988 | Fasline et al. |
| 4,732,800 A | 3/1988 | Groshens |
| 4,739,635 A | 4/1988 | Conley et al. |
| 4,750,443 A | 6/1988 | Blaustein et al. |
| 4,761,318 A | 8/1988 | Ott et al. |
| 4,775,310 A | 10/1988 | Fischer |
| 4,786,190 A | 11/1988 | Van Erden et al. |
| 4,794,028 A | 12/1988 | Fischer |
| 4,806,300 A | 2/1989 | Walton et al. |
| 4,815,172 A | 3/1989 | Ward |
| 4,854,735 A | 8/1989 | Rutledge |
| 4,872,243 A | 10/1989 | Fischer |
| 4,894,060 A | 1/1990 | Nestegard |
| 4,906,108 A | 3/1990 | Herrington et al. |
| 4,909,243 A | 3/1990 | Frank et al. |
| 4,913,560 A | 4/1990 | Herrington |
| 4,917,112 A | 4/1990 | Kalt |
| 4,920,235 A | 4/1990 | Yamaguchi |
| 4,931,343 A | 6/1990 | Becker et al. |
| 4,931,344 A | 6/1990 | Ogawa et al. |
| 4,933,224 A | 6/1990 | Hatch |
| 4,939,818 A | 7/1990 | Hahn |
| 4,955,981 A | 9/1990 | Provost |
| 4,972,829 A | 11/1990 | Knerr |
| 4,973,326 A | 11/1990 | Wood et al. |
| 4,981,749 A | 1/1991 | Kubo et al. |
| 4,984,339 A | 1/1991 | Provost et al. |
| 4,986,265 A | 1/1991 | Caponi |
| 4,992,124 A | 2/1991 | Kurihara et al. |
| 4,999,067 A | 3/1991 | Erb et al. |
| 5,015,251 A | 5/1991 | Cherubini |
| 5,032,122 A | 7/1991 | Noel et al. |
| 5,033,462 A | 7/1991 | Storey, Jr. et al. |
| 5,048,158 A | 9/1991 | Koerner |
| 5,066,289 A | 11/1991 | Polski |
| 5,086,763 A | 2/1992 | Hathman |
| 5,106,362 A | 4/1992 | Gilman |
| 5,116,563 A | 5/1992 | Thomas et al. |
| 5,131,119 A | 7/1992 | Murasaki et al. |
| 5,133,112 A | 7/1992 | Gomez-Acevedo |
| 5,137,508 A | 8/1992 | Engman |
| 5,142,743 A | 9/1992 | Hahn |
| 5,144,730 A | 9/1992 | Dilo |
| 5,151,320 A | 9/1992 | Homonoff et al. |
| 5,152,741 A | 10/1992 | Farnio |

| | | | | | |
|---|---|---|---|---|---|
| 5,167,613 A | 12/1992 | Karami et al. | 5,603,145 A | 2/1997 | Arakawa et al. |
| 5,168,603 A | 12/1992 | Reed | 5,603,946 A | 2/1997 | Constantine |
| 5,172,980 A | 12/1992 | Provost | 5,604,961 A | 2/1997 | Cole |
| 5,180,534 A | 1/1993 | Thomas et al. | 5,605,729 A | 2/1997 | Mody et al. |
| 5,200,245 A | 4/1993 | Brodrick, Jr. | 5,606,781 A | 3/1997 | Provost et al. |
| 5,214,942 A | 6/1993 | Peake, III et al. | 5,611,791 A | 3/1997 | Gorman et al. |
| 5,216,790 A | 6/1993 | Eschenbach | 5,614,232 A | 3/1997 | Torigoe et al. |
| 5,217,403 A | 6/1993 | Nobbs | 5,614,281 A | 3/1997 | Jackson et al. |
| 5,230,851 A | 7/1993 | Thomas | 5,615,460 A | 4/1997 | Welrich et al. |
| 5,231,738 A | 8/1993 | Higashinaka | 5,616,155 A | 4/1997 | Kronzer |
| 5,234,462 A | 8/1993 | Pavletic | 5,616,394 A | 4/1997 | Gorman et al. |
| 5,238,306 A | 8/1993 | Heintz et al. | 5,618,583 A | 4/1997 | Young et al. |
| 5,242,632 A | 9/1993 | Mende | 5,620,769 A | 4/1997 | Wessels et al. |
| 5,256,231 A | 10/1993 | Gorman et al. | 5,620,779 A | 4/1997 | Levy et al. |
| 5,260,015 A | 11/1993 | Kennedy et al. | 5,622,578 A | 4/1997 | Thomas |
| 5,267,453 A | 12/1993 | Peake, III et al. | 5,624,427 A | 4/1997 | Bergman et al. |
| 5,286,111 A | 2/1994 | Brembilla | 5,624,429 A | 4/1997 | Long et al. |
| 5,293,884 A | 3/1994 | Chapman et al. | 5,636,503 A | 6/1997 | Kaspszyk ...................... 54/23 |
| 5,300,058 A | 4/1994 | Goulait et al. | 5,637,080 A | 6/1997 | Geng |
| 5,304,162 A | 4/1994 | Kuen | 5,643,651 A | 7/1997 | Murasaki |
| 5,318,555 A | 6/1994 | Siebers et al. | 5,647,864 A | 7/1997 | Allen et al. |
| 5,318,741 A | 6/1994 | Thomas | 5,654,070 A | 8/1997 | Billarant |
| 5,321,855 A | 6/1994 | Ciuffo | 5,656,111 A | 8/1997 | Dilnik et al. |
| 5,326,415 A | 7/1994 | Thomas | 5,657,517 A | 8/1997 | Akeno et al. |
| 5,326,612 A | 7/1994 | Goulait | 5,662,599 A | 9/1997 | Reich et al. |
| 5,339,499 A | 8/1994 | Kennedy et al. | 5,664,302 A | 9/1997 | Thomas |
| 5,361,462 A | 11/1994 | Murasaki | 5,669,120 A | 9/1997 | Wessels et al. |
| 5,369,847 A | 12/1994 | Naya et al. | 5,669,900 A | 9/1997 | Bullwinkel et al. |
| 5,369,852 A | 12/1994 | Higashinaka | 5,669,901 A | 9/1997 | LaFortune et al. |
| 5,380,313 A | 1/1995 | Goulait et al. | 5,672,404 A | 9/1997 | Callahan, Jr. et al. |
| 5,382,461 A | 1/1995 | Wu | 5,685,756 A | 11/1997 | Noda |
| 5,383,872 A | 1/1995 | Roessler et al. | 5,695,377 A | 12/1997 | Triebes et al. |
| 5,386,595 A | 2/1995 | Kuen et al. | 5,699,593 A | 12/1997 | Jackson |
| 5,391,424 A | 2/1995 | Kolzer | 5,700,340 A | 12/1997 | Johnson et al. |
| 5,393,475 A | 2/1995 | Murasaki et al. | 5,702,356 A | 12/1997 | Hathman |
| 5,403,302 A | 4/1995 | Roessler et al. | 5,707,707 A | 1/1998 | Burnes et al. |
| 5,403,413 A | 4/1995 | Masuda | 5,722,968 A | 3/1998 | Datta et al. |
| 5,407,439 A | 4/1995 | Goulait | 5,736,214 A | 4/1998 | Billarant |
| 5,407,722 A | 4/1995 | Peake, III et al. | 5,747,584 A | 5/1998 | Noda |
| 5,415,626 A | 5/1995 | Goodman et al. | 5,749,129 A | 5/1998 | Murasaki et al. |
| 5,423,789 A | 6/1995 | Kuen | 5,755,015 A | 5/1998 | Akeno et al. |
| 5,431,622 A | 7/1995 | Pyrozyk et al. | 5,769,806 A | 6/1998 | Radow |
| 5,437,621 A | 8/1995 | Andrews et al. | 5,770,531 A | 6/1998 | Sudduth et al. |
| 5,437,623 A | 8/1995 | McClees et al. | 5,773,120 A | 6/1998 | Deka et al. |
| 5,441,687 A | 8/1995 | Murasaki et al. | 5,781,969 A | 7/1998 | Akeno et al. |
| 5,447,590 A | 9/1995 | Gilpatrick | 5,786,062 A | 7/1998 | Callahan, Jr. et al. |
| 5,449,340 A | 9/1995 | Tollini | 5,792,408 A | 8/1998 | Akeno et al. |
| 5,449,530 A | 9/1995 | Peake, III et al. | 5,800,845 A | 9/1998 | Akeno et al. |
| 5,452,877 A | 9/1995 | Riffle et al. | 5,807,300 A | 9/1998 | Nix, Jr. |
| 5,456,660 A | 10/1995 | Reich et al. | 5,816,709 A | 10/1998 | Demus |
| 5,470,417 A | 11/1995 | Goulait | 5,823,977 A | 10/1998 | Dalyea |
| 5,476,702 A | 12/1995 | Datta et al. | 5,830,298 A | 11/1998 | Jackson |
| 5,480,719 A | 1/1996 | Tollini | 5,843,018 A | 12/1998 | Shesol et al. |
| 5,500,268 A | 3/1996 | Billarant | 5,843,025 A | 12/1998 | Shaari |
| 5,505,747 A | 4/1996 | Chesley | 5,843,057 A | 12/1998 | McCormack |
| 5,512,234 A | 4/1996 | Takizawa et al. | 5,857,245 A | 1/1999 | Sakakibara et al. |
| 5,518,795 A | 5/1996 | Kennedy et al. | 5,858,515 A | 1/1999 | Stokes et al. |
| 5,531,732 A | 7/1996 | Wood | 5,868,275 A | 2/1999 | Moody |
| 5,535,787 A | 7/1996 | Howell | 5,876,365 A | 3/1999 | Hart |
| 5,537,720 A | 7/1996 | Takizawa et al. | 5,891,547 A | 4/1999 | Lawless |
| 5,537,723 A | 7/1996 | Yoshida et al. | 5,897,545 A | 4/1999 | Kline et al. |
| 5,542,942 A | 8/1996 | Kline et al. | 5,897,547 A | 4/1999 | Schmitz |
| 5,547,531 A | 8/1996 | Allen et al. | 5,908,680 A | 6/1999 | Moren et al. |
| 5,554,239 A | 9/1996 | Datta et al. | 5,945,131 A | 8/1999 | Harvey et al. |
| 5,556,375 A | 9/1996 | Ewall | 5,953,797 A | 9/1999 | Provost et al. |
| 5,565,255 A | 10/1996 | Young et al. | 5,983,467 A | 11/1999 | Duffy |
| 5,569,233 A | 10/1996 | Goulait | 5,984,911 A | 11/1999 | Siebers et al. |
| 5,580,346 A | 12/1996 | Spier | 5,989,204 A | 11/1999 | Lina |
| 5,586,371 A | 12/1996 | Thomas | 5,997,522 A | 12/1999 | Provost et al. |
| 5,595,014 A | 1/1997 | Moore | 6,017,606 A | 1/2000 | Sage et al. |
| 5,595,567 A | 1/1997 | King et al. | 6,035,498 A | 3/2000 | Buzzell et al. |

| | | | | | |
|---|---|---|---|---|---|
| 6,043,408 A | 3/2000 | Geng | JP | 6-123061 | 5/1994 |
| 6,051,094 A | 4/2000 | Melbye et al. | JP | 6-141913 | 5/1994 |
| 6,060,009 A | 5/2000 | Welygan | JP | 7-171011 | 7/1995 |
| 6,080,347 A | 6/2000 | Goulait | JP | 7-231842 | 9/1995 |
| 6,093,160 A | 7/2000 | Augustine et al. | JP | 7-300752 | 11/1995 |
| 6,106,922 A | 8/2000 | Cejka et al. | JP | 8-27657 | 1/1996 |
| 6,115,891 A | 9/2000 | Suenaga et al. | JP | 9-195153 | 7/1997 |
| 6,197,404 B1 * | 3/2001 | Varona | JP | 9-195154 | 7/1997 |
| 6,205,623 B1 | 3/2001 | Shepard et al. | JP | 9-195155 | 7/1997 |
| 6,248,419 B1 | 6/2001 | Kennedy et al. | JP | 9-309168 | 12/1997 |
| 6,406,467 B1 | 6/2002 | Dilnik et al. | JP | 10-146207 | 6/1998 |
| 6,463,635 B1 | 10/2002 | Murasaki | JP | 10-151005 | 6/1998 |
| 6,481,063 B1 | 11/2002 | Shepard | JP | 10-165207 | 6/1998 |
| 6,489,003 B1 | 12/2002 | Levitt et al. | WO | WO 92/01401 | 7/1991 |
| 2001/0016245 A1 * | 8/2001 | Tuman et al. ............... 428/99 | WO | WO 95/05140 | 2/1995 |
| 2001/0018110 A1 | 8/2001 | Tuman et al. | WO | WO 99/17631 | 3/1995 |

FOREIGN PATENT DOCUMENTS

| | | | | | |
|---|---|---|---|---|---|
| EP | 0 324 577 | 7/1989 | WO | WO 95/17111 | 6/1995 |
| EP | 0 341 993 A1 | 11/1989 | WO | WO 95/33390 | 12/1995 |
| EP | 0 482 749 A1 | 4/1992 | WO | WO 96/03101 | 2/1996 |
| EP | 0 604 731 A1 | 7/1994 | WO | WO 96/14459 | 5/1996 |
| EP | 0 766 934 A2 | 9/1996 | WO | WO 96/19960 | 7/1996 |
| EP | 0 749 707 A1 | 12/1996 | WO | WO 97/25892 | 7/1997 |
| EP | 0 780 505 A2 | 12/1996 | WO | WO 97/25893 | 7/1997 |
| EP | 0 765 616 A1 | 4/1997 | WO | WO 98/33410 | 8/1998 |
| EP | 0 826 354 A2 | 8/1997 | WO | WO 99/22619 | 10/1998 |
| EP | 0 937 420 A2 | 9/1999 | WO | WO 9911452 A1 * | 3/1999 |
| EP | 0 605 013 A1 | 7/2004 | WO | WO 99/17630 | 4/1999 |
| GB | 2 285 093 A | 12/1994 | WO | WO 99/48455 | 9/1999 |
| GB | 2 290 052 A | 6/1995 | WO | WO 00/27235 | 5/2000 |
| GB | 2 296 423 B | 12/1995 | | | |
| JP | 2-41156 | 2/1990 | | | |
| JP | 22-191735 | 7/1990 | | | |
| JP | 4-56008 | 2/1992 | | | |
| JP | 6-33359 | 2/1994 | | | |

OTHER PUBLICATIONS

"Elastic Loop Tapes", XP–002091024, Velcro Fastening Systems, Product Information Guide, Aug. 1997.

* cited by examiner

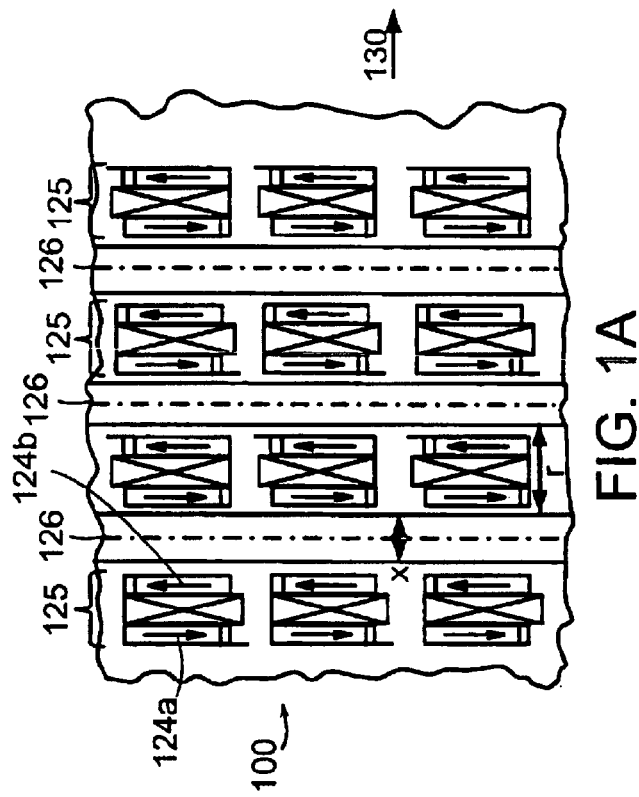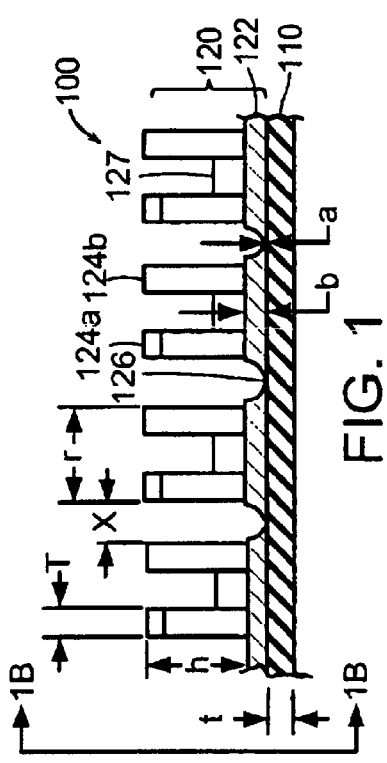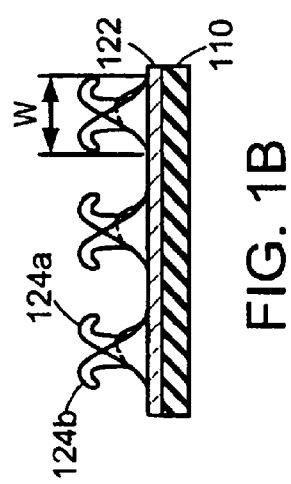

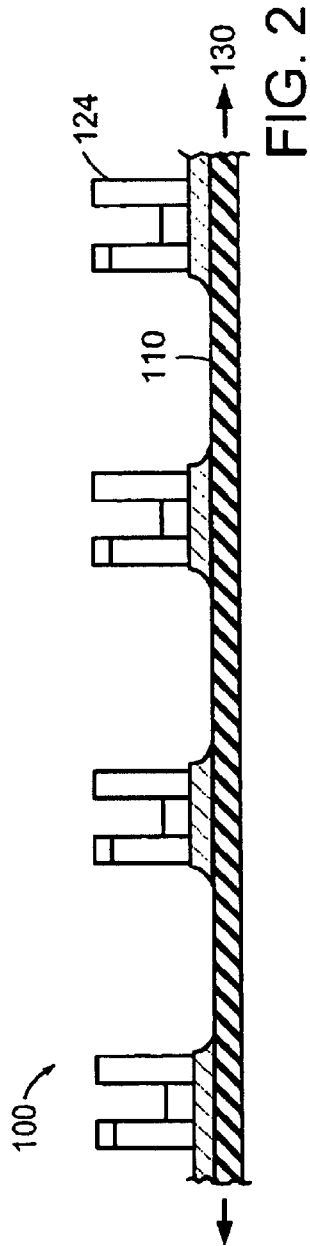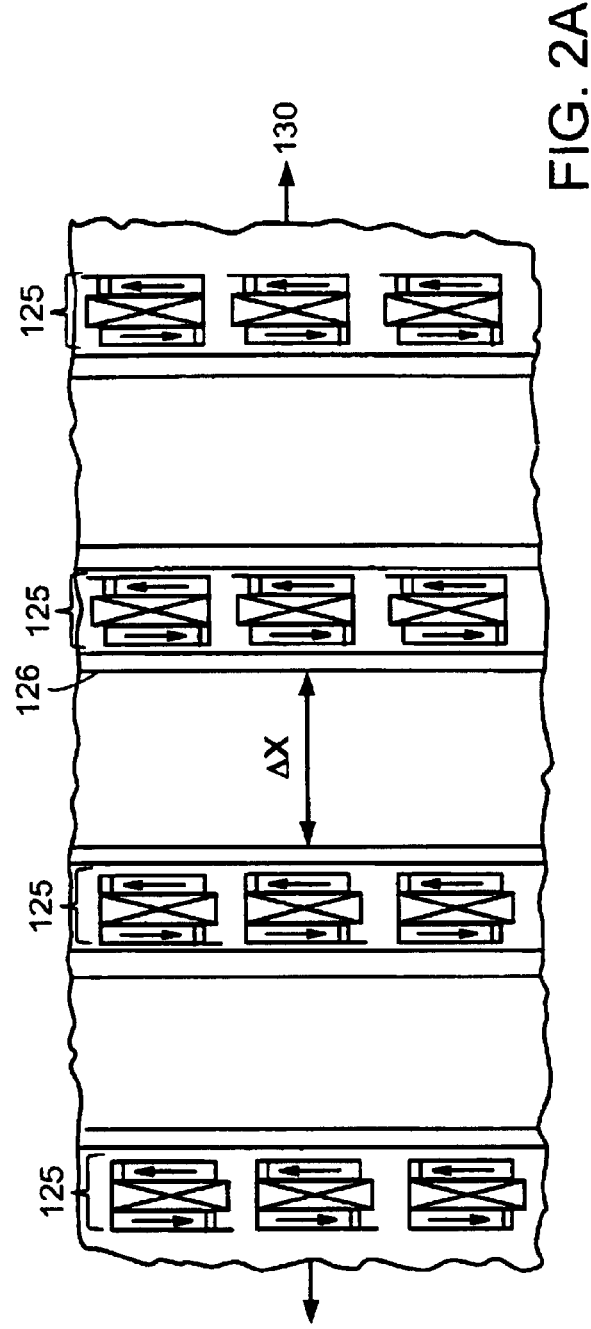

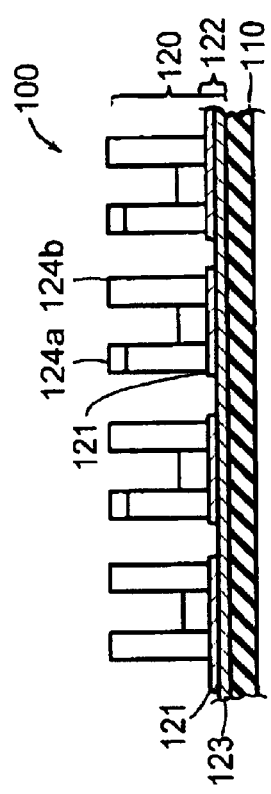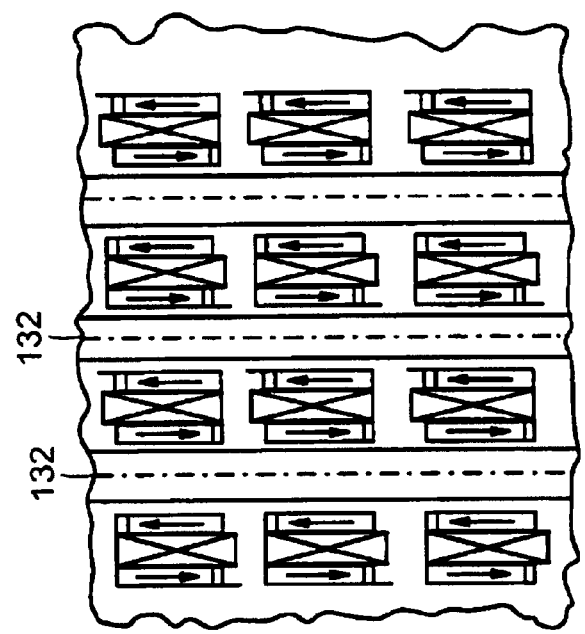
FIG. 3
FIG. 3A

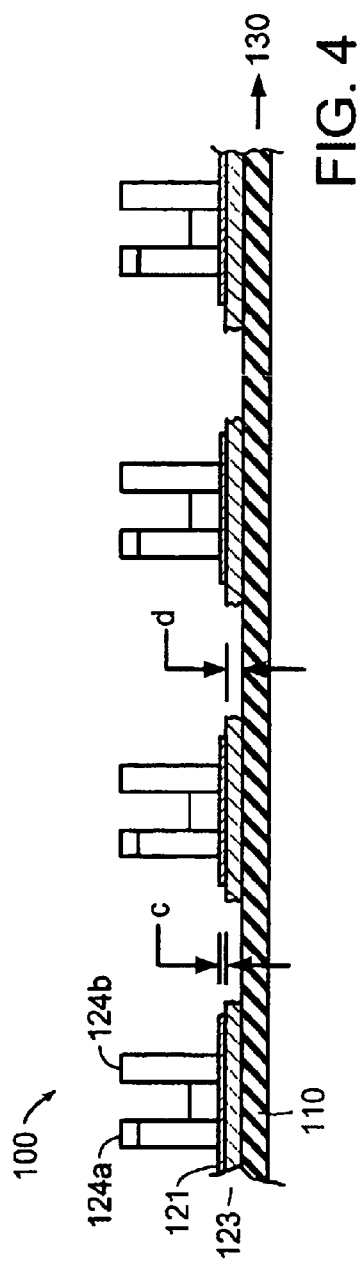
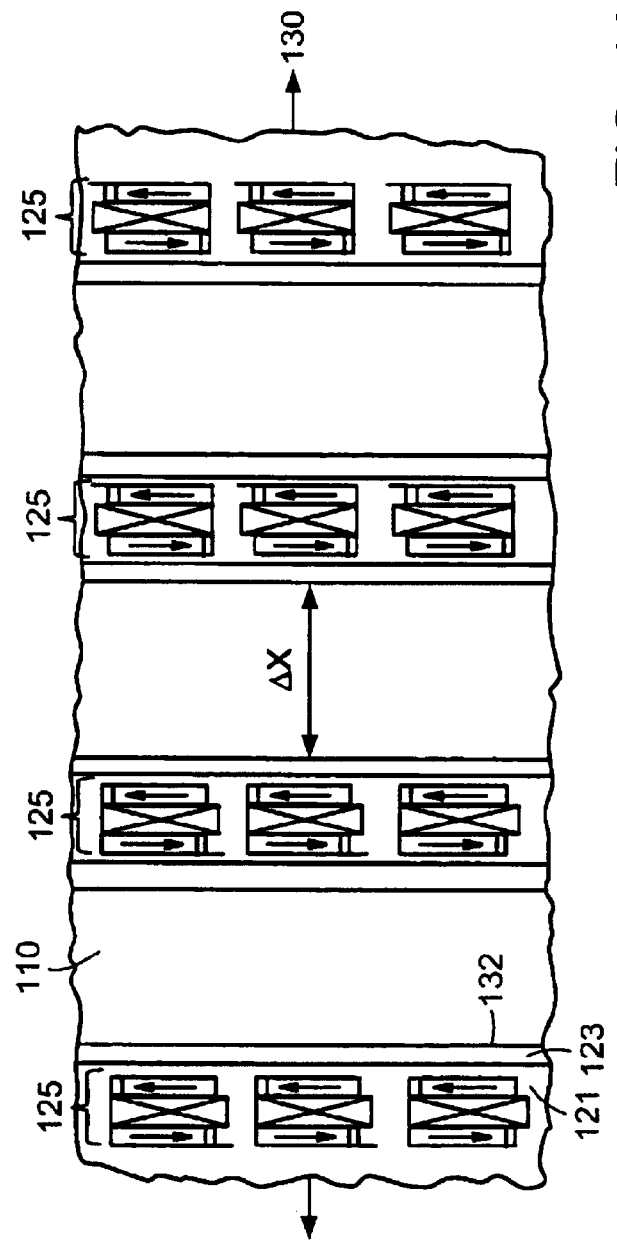

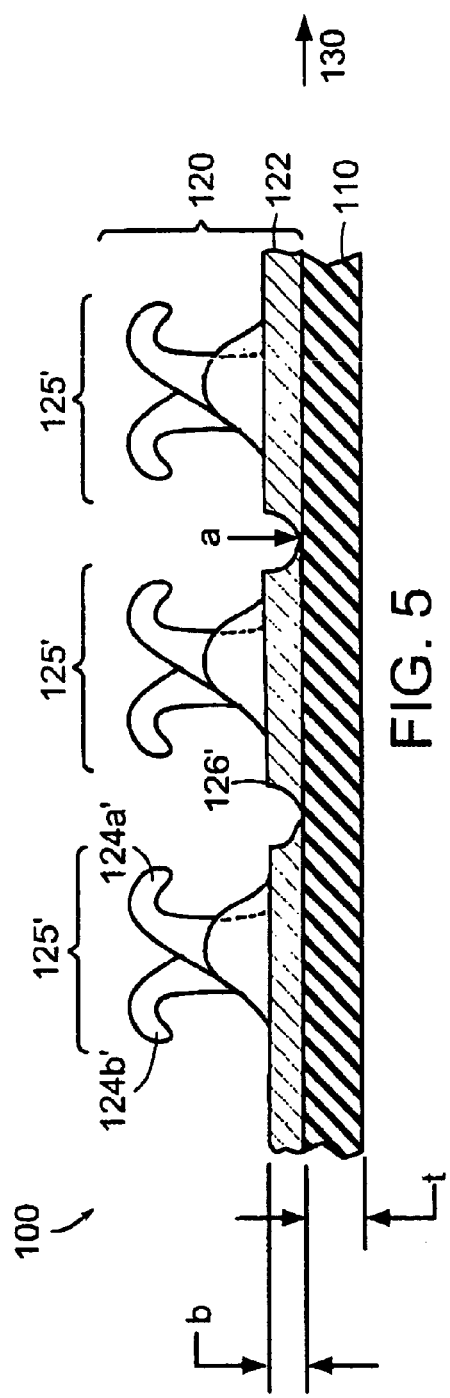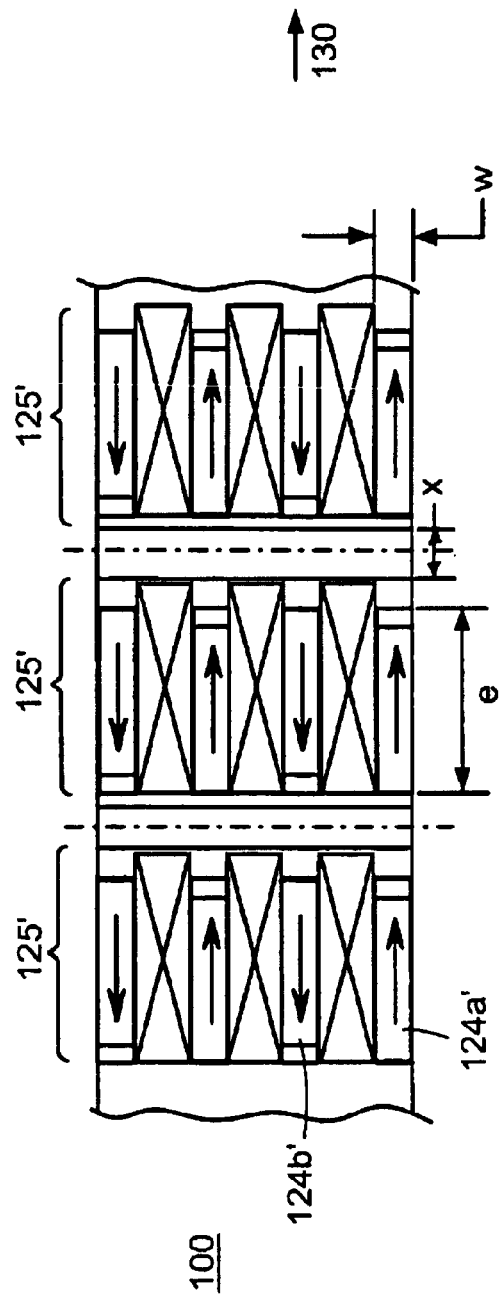
FIG. 5
FIG. 5A

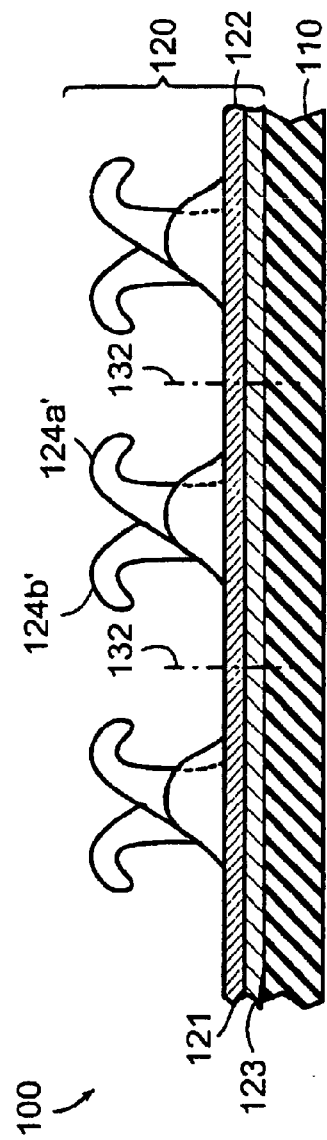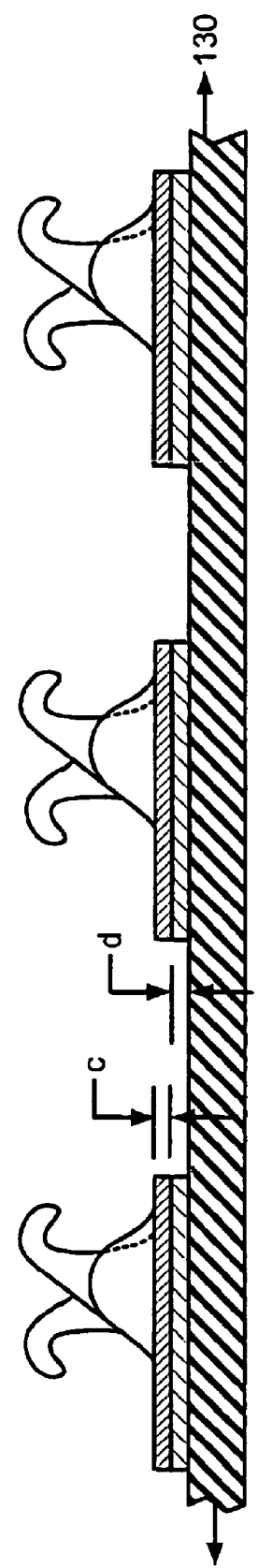

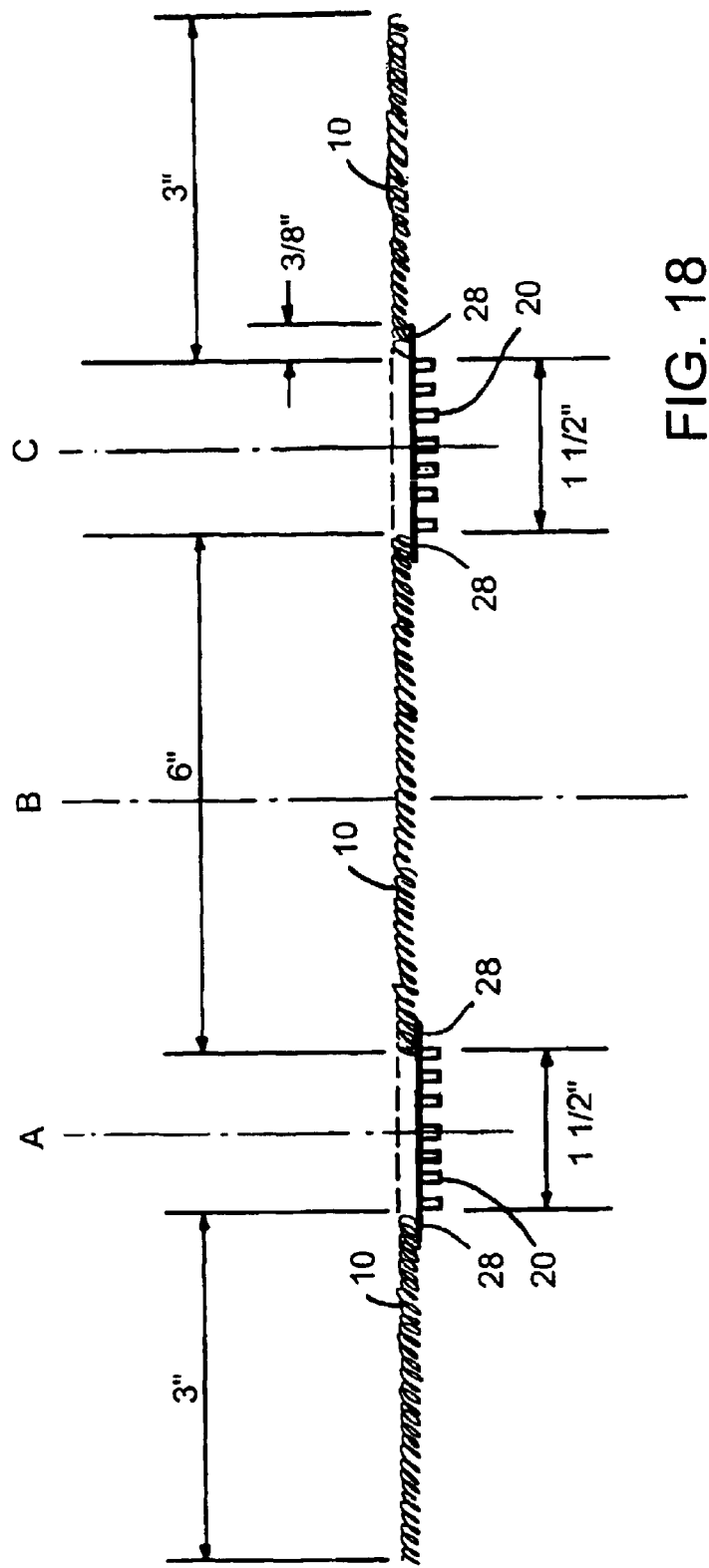

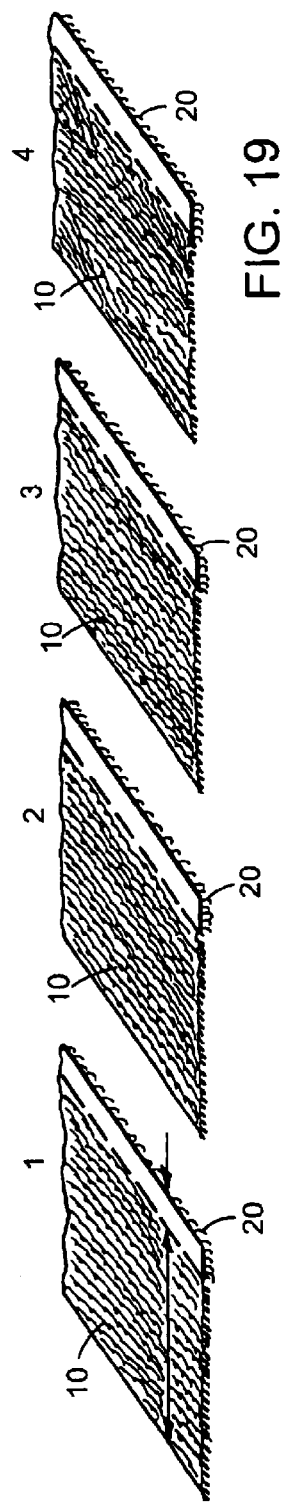
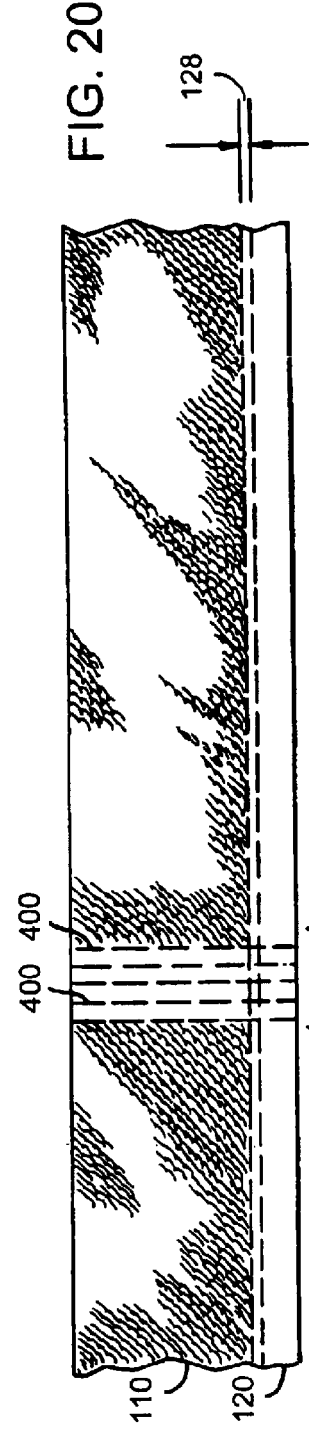
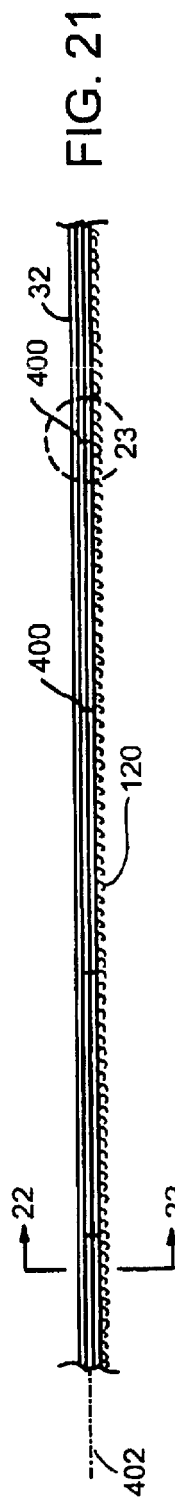
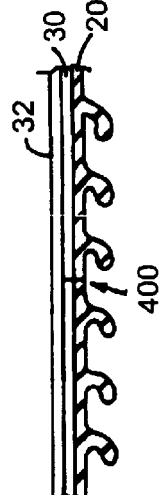
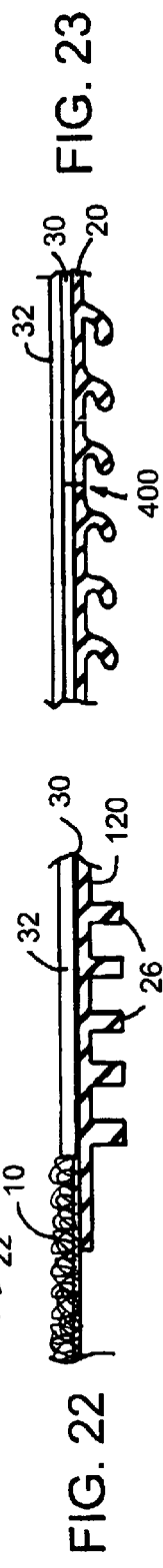

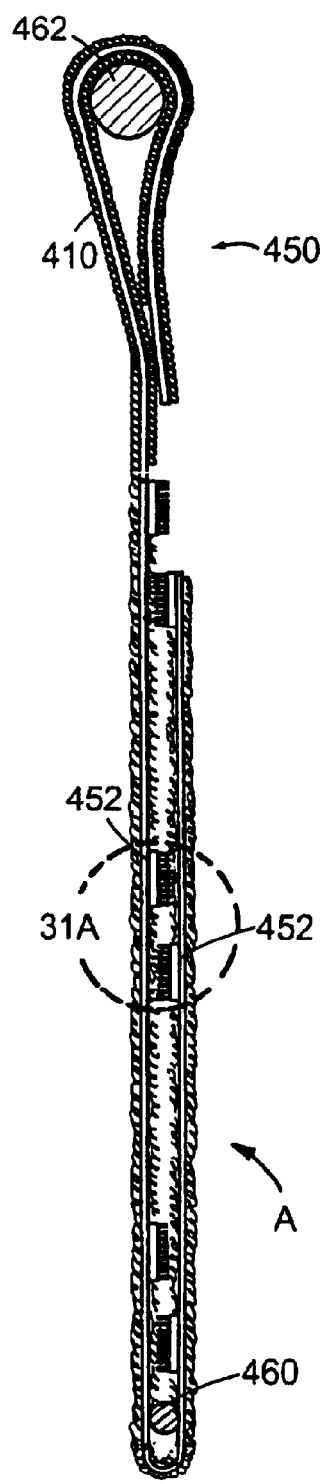
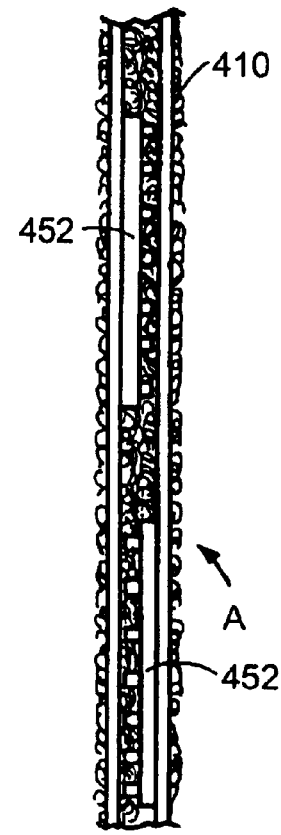
FIG. 31
FIG. 31A

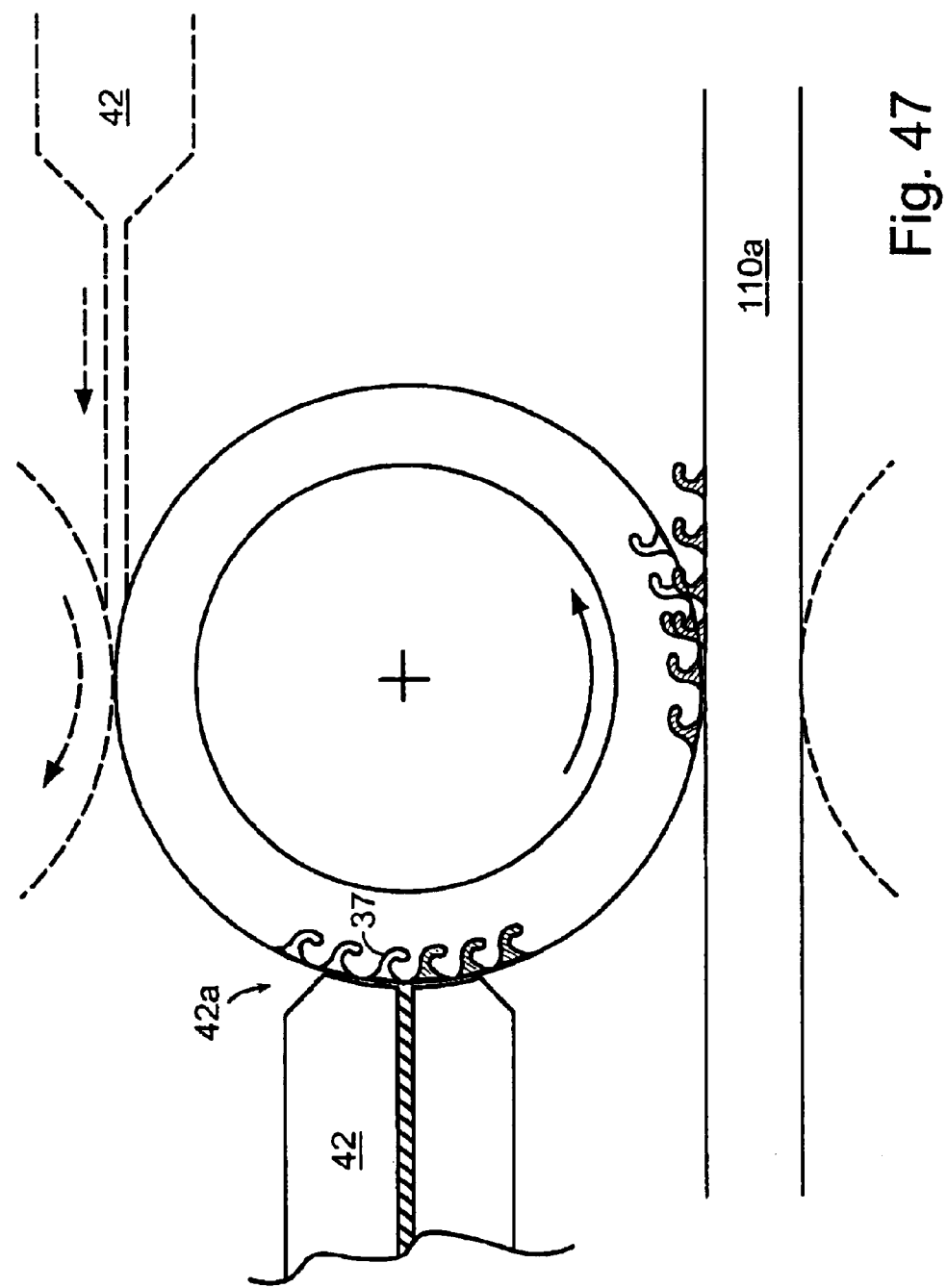

HOOK AND LOOP FASTENING

This application claims priority from U.S. Provisional Application No. 60/242,877, filed Oct. 24, 2000 and U.S. Provisional Application No. 60/189,125, filed Mar. 14, 2000.

TECHNICAL FIELD

This invention relates to hook and loop fastening and especially to stretchy or flexible hook and loop fastenings, tabs, straps, ties, and wrappings that can be practical and cost-effective for fastening applications where elasticity or flexibility are desired. The invention also relates to improved fastener materials, to composite products, and to machines and processes for forming flexible and elastically stretchable products, and other products that involve hook and loop fastening.

BACKGROUND

Stretchy or flexible fastener tabs and fastenings that carry hook and loop closures are desirable, for instance, as parts of infant and adult diapers, surgical gowns, and other garments and wraps. Fastener tabs typically comprise sheet, film or nonwoven web that have embossing or other surface patterns for grasping by the user. To the back of such material, a tape segment of fastener elements is secured, forming a laminate structure. The fastener tape is typically made of a synthetic resin that is not stretchable, and the resulting laminate, in the region of the tape segment, typically is relatively stiff, does not stretch or flex as desired, or does not present the desired degree of cloth-like feel.

It is desirable that the substance of the tab and the associated fastener tape provide an integral component that achieves desired qualities, such as elasticity, flexibility and cloth-like feel. The invention relates to filling such needs with novel fastenings, and to machines and methods of manufacture that enable manufacture of such fastenings, as well as other desirable products.

This invention also relates to composite hook and loop fastenings, straps, ties or wrappings, which include both hook and loop regions and to methods of their manufacture, constituents of such composites, and products employ such fastenings.

A typical composite hook and loop fastener that has been commercially successful is produced by overlapping and attaching pre-formed hook material and pre-formed loop material and overlapping and attaching the two materials together along their edge margins or by totally overlapping one over the other. The attaching has been done by ultrasonic welding, thermal fusing and adhesive bonding, steps which add to the cost of the manufacturing process. Composite hook and loop materials formed by in situ lamination uniformly across an extensive surface of a pre-formed loop web during forming the hook component have also had advantageous uses but have had limitations in other circumstances. Other proposals have involved impregnating a web so that resin of the formed hooks lies on both the hook side and the opposite side of a second material, or have required special materials that are costly or difficult to manufacture, such as separately formed woven and knit loop materials, or have presented other disadvantages, such as difficulty in manufacture and in achieving the optimal balance of desired properties such as hook and loop engageability, stretchiness, flexibility, feel, uniformity and cost.

The following references represent prior proposals directed, in one way or another, to aspects of some of the problems addressed here or to materials useful in stretchable, flexible or composite fastening products. While perhaps effective in some respects, in other respects they have not fully met needs met by the present invention. We refer to U.S. Pat. Nos. 4,058,853; 4,247,967; 4,654,246; 4,672,722; 5,133,112; 5,172,980; 5,318,555; 5,669,120; 6,080,347; and 6,106,922; and to EPO No. 826,354 and WO No. 99/176 31. These references describe applications of stretchy fastening or stretchy loop material, define the ranges of elongation and strength in which elastically stretchable fastening is needed and describe elastic carrier materials that can be useful. Accordingly their full disclosures are incorporated herein by reference.

SUMMARY

In one aspect of the invention, a stretchable fastener tape or fastening article comprises an array of fastening elements for hook and loop fastening, e.g. hooks having molded stems extending from respective bases, the product having parting lines or parting regions at spacings to define bands or islands of elastically separable fastener elements. The array is in situ laminated to the face of an elastically stretchy sheet-form carrier or to the surface of a top layer attached to the stretchy carrier. In important embodiments in which there are multiple linear bands of fastener elements, linear parting lines or parting regions extend transversely to the direction of a user's tension. When the fastening article is pulled by the user, the bands of fastening elements move freely with respective portions of the elastic carrier layer on the surface of which they reside, the overall array of fastener elements expanding with the substance of the elastic carrier. Such parting lines and parting regions also inherently provide lines or regions of flexure, at which the elastic carrier can bend or flex relatively free of constraint. Likewise, when a carrier is chosen which is flexible or highly flexible, though not elastic, such as a highly flexible hook-engageable loop material, the parting lines or parting regions of the construction serve as flexure lines or flexure regions that contribute to the flexibility of the overall product.

In another aspect, the invention provides a fastener having a sheet-form carrier of elastic composition and one or more band or islands of fastener elements of a band synthetic resin secured to at least a portion of the surface of the sheet. The fastener elements each have a base, or extend from a common base layer made at least in part of synthetic resin which is integrally formed with stems of the fastener elements. The base of each of the stems, or the base layer from which the stems extend, is in situ laminated to the carrier sheet and constructed to be dominated by the elasticity or flexibility of the carrier so that the bands or islands of fastener elements move with stretching or flexing of the carrier. For this purpose, a base layer from which hooks extends is preferably discontinuous, and may have a set of spaced parallel parting lines or linear bands or regions that are resin-free, or flexure extending transversely to the direction of tension or flexure applied to the carrier during use. Thus, tension applied during use to a fastener material having an elastic carrier causes bands or islands of hooks to separate further from each other, or to flex freely relative to one another. A two dimensional pattern of resin-free regions in which islands of in situ laminated fasteners are dispersed enables stretching or flexing in all directions.

Closely spaced parting lines cut in a continuous base sheet for the fastener elements or narrow parting regions over an area otherwise fully covered by hooks can maximize the area covered by hooks, which is useful, e.g., for small hook segments of diaper tabs.

Implementation of such aspects of the invention may include one or more of the following features. Where a hook base layer is employed, its thickness at parting regions is reduced or eliminated. The parting regions are defined by a pattern of grooves formed in a base layer. The parting regions comprise cuts in a base layer defining parting lines. The fastener hooks have stems that are molded in rows corresponding to a machine direction in which the fasteners are formed, and a base layer of the hooks has a large multiplicity of straight parting lines or linear resin-free regions that extend either in the machine direction or perpendicular to the machine direction, or form an X,Y, grid. The base of the strip of fastener elements may include a first base layer integral with the fastener elements and a second base layer. The second base layer can be laminated to the first base layer and have yieldable character, thus enabling the spacing of the fastener elements to expand with stretch of the carrier sheet. In one case, the second base maybe made of a substance rupturable under tension applied to the fastener during use or have parting lines that establish preferential rupture lines. In another case, the second base layer may be made of relatively stretchy material compared to synthetic resin that forms the fastener hook elements, which stretches with stretch of the principal carrier sheet. The product is preferably an in situ laminate, in which the synthetic resin of the first layer, during molding of the fastener elements and forming the first base layer, serves to adhere and bond the fastener elements to the surface of a pre-formed second layer. The elastic sheet-form carrier may be made e.g., of thermoplastic elastomer, such as thermoplastic polyurethane or of elastomeric copolymer containing PET, such as Hytrel® of E I Du Pont de Nemours and Company.

According to another aspect of the invention, a method of manufacturing a stretchable or flexible fastener includes the following steps: molding a continuous or discontinuous sheet of a hook component having a base of synthetic resin in the form of rows, bands or islands of stems of loop-engageable hooks, while simultaneously providing a pre-formed carrier sheet of elastic or flexible construction or other work pieces and integrally laminating the base of the hook component at least partially to a surface of the sheet, or work pieces including forming a set of closely spaced parallel parting lines or parting regions, such as resin-free regions between the rows, bands or islands of loop-engageable hooks.

Implementation of such aspects of the invention may include one or more of the following features. The regions may be formed by reducing or eliminating the thickness of the base of the hooks between bands rows or islands of loop-engageable hooks or, parting lines may be formed by cutting a continuous base layer of the hook component between bands or islands of loop-engageable hooks.

In certain preferred embodiments, fastener bands or islands include hooks having crooks aligned in one direction in opposite senses, the bands extending in the direction in which crooks of the hooks point or extending in the direction perpendicular to that direction. In other case the fasteners comprise flat-topped stems or are of so-called mushroom shaped.

For elastically stretchy fastening in one case the base of the hooks is preferably in situ laminated directly to the surface of a main pre-formed elastic carrier sheet. In another case a relatively thin base layer of the hooks is in situ laminated to a first pre-formed sheet, which may be stretchable or define appropriate stretchable regions or may be rupturable in the parting regions, followed by laminating the first sheet to a carrier sheet of elastic construction.

In certain embodiments, as where it is desired to maximize the number of hooks in the array, cuts or very narrow grooves or resin free-regions are employed between bands or islands of hooks to define, respectively, parting lines or narrow parting or flexible regions, and very few rows of hooks comprise each band or island. In other cases, larger width parting or flexible regions may be usefully employed. In certain embodiments the bands or islands of hooks of single crook, palm tree, flat-topped stem or mushroom configuration comprises a relatively large multiplicity of closely adjacent rows of hooks.

According to another aspect of the invention, there is provided a composite hook and loop fastener in the form of an elongated strip or sheet suitable for a fastening, tab, strap, tie or wrapping, which includes at least one stretchy or flexible hook-engageable loop band, and at least one hook band or hook island permanently affixed to a surface of the loop band by in situ lamination. The loop material may be woven or knit, or in many cases, is preferably defined by suitably anchored fibers. In some important cases, the products comprise a large multiplicity of alternating bands of fastener hooks and of loop material, presenting a striped appearance on one side sometimes referred to here as a "zebra-like" appearance. In certain advantageous cases the back of the strip or sheet is free of hook raising, and is important cases actually provides a uniform distribution of hook-engageable loops. One portion of the product is available, for instance, for encircling an object to be wrapped and engaging the fastener elements of the hook band(s) with the loops or fibers of the loop band. In certain embodiments, the one or more loop band(s) each preferably comprises a self-supporting, elastically stretchy or flexible web of entangled fibers, the fibers forming both a sheet-form body and hook-engageable loops extending from at least one surface of the body, and the hook band or each band has fastener elements extending from a common base, which is joined to the stretchy loop material by in situ lamination. In some preferred embodiments, the bands, islands or patterns of loop-engageable hooks are laminated to one side of a wide loop material of uniform construction, which provides loops in those regions of that side not occupied by the hooks. In certain preferred embodiments of this aspect, the back of the product presents a uniform, resin-free appearance, and can uniform a wide field of hook-engageable loops when desired.

In important embodiments, a hook band or island comprises a base of synthetic resin and an array of loop-engageable fastener elements, the stems of which are integrally molded with and extend from the base or a first surface of a base layer, at least a portion of the base being laminated in situ to a surface of the loop material, preferably directly to the loop material.

Implementations of this aspect of the invention may include one or more of the following features. The web of the loop component may be of uniform construction throughout its width and may comprise a nonwoven fabric having exposed fibers that define loops. In certain cases, preferably the web is a needled nonwoven fabric, or a composite fabric. A nonwoven needled web may weigh less than about 4 ounces per square yard (136 grams per square meter), preferably, in many instances, less than 2 ounces per square yard (68 grams per square meter). The nonwoven web may be in a stretched state (due, in the case of forming a stretchy carrier, to pre-stretching predominantly or totally in its lengthwise direction), that is then stabilized by activation or application of a binder, (preferably, for a stretchy carrier, using a binder having elastic qualities), that prevents substantial return of the web to its original unstretched state. In the case of an elastically stretchy carrier, the web is n preferably stretchy mainly in its widthwise, direction. The loops of the loop component may extend from loop structures, and at least some of the loop structures may each have a common, elongated trunk portion extending from the web from an associated knot, with multiple loops extending from the trunk portion. The loop component may have a margin in which surface fibers or loops of the component are encapsulated in resin of the hook component, and a main body free of hook component resin, or may serve as the carrier of multiple spaced apart bands or islands of hooks, while defining effective bands or regions of loops adjacent to the regions of hooks. The loop prior to the in situ lamination of the regions of hooks, the free hooks, the free loops being unavailable component may have two broad, opposite sides, and loops may uniformly extend to be engageable on either side by hooks. The hooks, preferably comprising parallel rows of hooks in bands or spaced-apart island of hooks, may have dimensions less than the regions of loop component, and may be provided on one or both sides of the product. The fastener elements of the hook component may be hooks having single crooks or may be of palm tree, flat topped stem or mushroom shape.

According to another aspect of the invention, a method is provided for manufacturing a fastening or fastener tab, strap, tie or wrapping, including the following steps: providing a longitudinally continuous pre-formed sheet of stretchy or flexible loop material, the loop material having loops extending from at least a first surface; permanently bonding by in situ laminating in a nip formed by a mold roll and a pressure roll at least one band of plastic hook material to a selected region only to a surface structure of the loop material to form a laminate, with the hook material at least partially overlapping the loop material widthwise and in many cases having a width significantly less than the width of the loop material, the stems of the hook material being integrally molded with and extending from their bases or a base layer in situ laminated to the loop material; and cutting the laminate to form a fastening or fastener tab, strap, tie or wrapping that has at least one portion of the loop material and at least one portion of the hook material.

Implementations of this aspect of the invention may have one or more of the following features. The step of bonding may include continuously feeding the pre-formed loop material through a nip defined between a rotating mold roll and a pressure roll, the rotating mold roll defining a multiplicity of fixed cavities about its periphery for molding at least the stems of the fastener elements of the hook material, while introducing molten resin to the mold roll under conditions which cause the resin to fill the cavities of the mold roll via the stem regions of the cavities, in which pressure in the nip defined between the two rolls bonds the hook material to the surface structure of the loop material. The molten resin may be introduced to the mold roll in multiple, discrete regions along the roll, thereby forming multiple, parallel strips of hook at least the base of the stems of the material being laminated to the loop material. The loop material may be uniform, widthwise, and extend the full width of the in situ molding and laminating station or the loop material is fed into the nip in the form of multiple parallel strips, the hook material residing between adjacent strips of hook material in the nip, and have its surface structure in situ laminated to the hook material. After the in situ molding and bonding step, the laminate may be slit longitudinally into multiple, longitudinally continuous strips, each strip including both hook material and loop material, and cut transversely at appropriate widths to form stretchy or flexible tabs, straps, ties or wrappings.

In certain preferred embodiments, a method includes providing the loop material as a web having a nonwoven, exposed surface comprising entangled fibers, the fibers forming both a sheet-form web body and hook-engageable freestanding loops extending from at least one surface of the web body. In certain preferred embodiments, the loop material is the needled, stretched and stabilized web described herein. In other cases the loop material comprises a laminate of a resin film and a nonwoven layer on one side or on both sides, for stretch products the resin film being elastic, such as a thermoplastic electromer.

Fastenings, including stretchy or flexible "zebra-like" and "leopard like" appearing materials, are provided having spaced bands or a distribution of islands of molded loop-engageable hooks or molded pre-forms for hooks, between which are bands or regions of different character. Molding is by rigid molds filled from the base region of the stems. In certain preferred embodiments, linear bands or islands of fastener elements are themselves inextensible in the direction of their extent and comprise multiple rows of fastener elements. For ease of forming a uniform, elastically stretchy or flexible product, the bands or islands of fastener elements extend in the machine direction during manufacture. Embodiments shown employ a widthwise continuous carrier of uniform character to which multiple spaced bands or islands of hooks have their molded stems in situ bonded, and in other embodiments, over-lapping margins of the bases of hook bands are in situ laminated to the surface structure of adjacent bands of carrier using a laminating/molding nip in which one of the rolls is a mold roll, the pressure of the nip being effective to produce laminating bond with the bases of the stems or a common base layer, without having the resin permeate the entire thickness in the case porous substrates carriers. For a preferred mode of manufacture of an elastically stretchy product, stretchy carrier material is provided that it stretchy substantially only in the widthwise, (cross-machine) direction. In composite hook and loop fastener products, the bands or regions of material that is between adjacent bands or islands of hooks comprise loop-engageable material, uniform in construction widthwise the loop-forming material itself being an elastically stretchable or a flexible component. In useful product categories the hook bands or islands and intervening regions of material have importantly different width ranges. In a hook portion of a fastener tab, hook bands are at least as wide as and preferably wider than intervening bands or islands or regions of elastically stretchy or flexible material. For a wide range of straps and wrappings, especially for medical and athletic use, in which the intervening material comprises hook-engageable loops, the width of the bands or regions of loop material ranges between about 1 and 5 times as wide as adjacent bands or regions of hooks. Where the material is to provide a wrapping as in cable wraps or to form the body of envelopes or pouches, the width of the bands or regions of loop material are more than 5 times, and in some cases more than 10 times the width of adjacent fastener element bands or regions. For, e.g. long straps or ties, an extended length of loop material is arranged to engage with a small patch of hooks. Novel elastically stretchable and flexible loop-defining materials and their methods of manufacture and for molding the products are shown. In situ lamination of hook, bands or islands on materials held in a planar orientation or presenting a planar surface, extend in rigid flexible materials is also featured.

Other aspects, features and advantages of the invention will be apparent from the following description of embodiments, and from the claims.

DESCRIPTION OF DRAWINGS

FIG. 1 is a cross-machine direction, cross-sectional view of a stretchy hook fastener.

FIG. 1A is a top view of the fastener of FIG. 1.

FIG. 1B is a machine direction, cross-sectional view of the stretchy fastener of FIG. 1 taken in plane 1B—1B of FIG. 1.

FIG. 2 is a view of the hook fastener similar to that of FIG. 1, in a stretched state.

FIG. 2A is a top view of the stretched hook fastener of FIG. 2.

FIG. 3 is a cross-machine, cross-sectional view similar to FIG. 1, of another embodiment of a stretchy hook fastener according to the invention.

FIG. 3A is a top view of the hook fastener of FIG. 3.

FIG. 4 is a cross-machine, cross-sectional view of the hook fastener of FIG. 3 in a stretched state.

FIG. 4A is a top view of the hook fastener of FIG. 3 in a stretched state.

FIG. 5 is a machine direction, cross-sectional view of another embodiment of a stretchy hook fastener.

FIG. 5A is a top view of the fastener of FIG. 5.

FIG. 7 is a machine direction, cross-sectional view of another embodiment of a stretchy hook fastener according to the invention.

FIG. 7A is a similar view of the hook fastener of FIG. 7 in a stretched state.

FIGS. 9B through 9E are views of other machine arrangements for forming parting or flexural regions in hook material while

FIG. 17A is a perspective view of a portion of the apparatus of FIG. 16 modified for forming a preferred product of FIG. 18, while

FIG. 18 illustrates in magnified, diagrammatic cross-machine, cross-sectional view, a web comprised of in situ attached loop and hook bands formed with the apparatus of FIGS. 17A and 17B.

FIG. 19 is a perspective view of four hook and loop segments formed by slitting the web shown in FIG. 18.

FIG. 20 is a top view of a hook and loop segment that has been perforated cut.

FIG. 21 is an enlarged side view of the hook and loop segment, taken along line 21—21 in FIG. 20.

FIG. 22 is a magnified cross-sectional view of the interface between the hook and loop segments, taken along line 22—22 in FIG. 21.

FIG. 23 is a similarly magnified cross-sectional view of the circled area in FIG. 21.

FIG. 26 is a diagrammatic illustration of a knit loop material in a relaxed state while

FIG. 28A is a transverse cross-sectional view taken on line 28A—28A of FIG. 28, on an enlarged scale, indicating by a circle a section at which FIG. 27A is taken.

FIG. 31 is an illustration of a use of the article of FIG. 30 as a supporting strap.

FIG. 31A is a magnified view of the material within circle 31A of FIG. 30.

FIG. 32 illustrates adaptation of the article of FIG. 30 as a cinching strap while

FIG. 33 illustrates an article cut along lines C of FIG. 28 while

FIG. 35 is a plan view of a further starting material, while

FIG. 47 is a cross-sectional view of the mold roll of FIG. 46 taken along line 47—47 of FIG. 46.

DETAILED DESCRIPTION OF PREFERRED EMBODIMENTS

Figure 6:
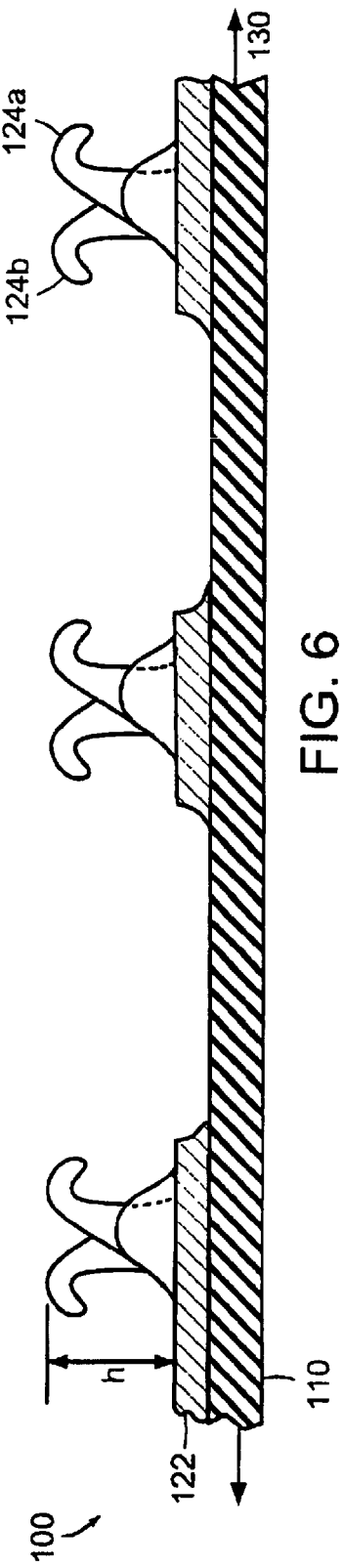
FIG. 6 is a machine direction, cross-sectional view of the hook fastener of FIG. 5 in a stretched state.

Referring to the embodiment of FIGS. 1, 1A, and 1B, a stretchy fastener 100 features an elastic carrier layer 110 laminated to a fastening layer 120. The fastening layer 120 has a base layer 122 and linear bands 125 of rows of hook elements 124a, 124b, the stems of which are integrally molded with the base layer (FIGS. 1A and 1B). Tiny, loop-engageable hooks 124a and 124b have single crooks at the ends of molded stems, in this case, the crooks also being of molded form, employing fixed mold cavities such as described in Fischer U.S. Pat. No. 4,872,243, hereby incorporated by reference. The mold cavities fill by entrance of molten resin via the open base region of the stems of the hook fastener cavities.

In the example shown, the molded crooks of hooks 124a are aligned in the same direction as, but oriented to point in the opposite sense to that of the hooks 124b in the immediately adjacent parallel row of the respective band of hooks, (see the direction of the arrows). The direction of the rows of hooks is perpendicular to stretching direction 130 (FIG. 1A). In one direction, in this case corresponding with the direction in which the crooks of the hooks are aligned, the base layer 122 is continuous in thickness and provides hook bands 125 that are relatively inextensible. Between the bands of hook elements 125 there are discontinuities in the base material that provide parting regions 126. The regions 126 are formed by grooves that make the base very thin, or non-existent between the bands of hooks, as shown.

Other molded forms of loop-engageable hooks may be employed, e.g. of palm tree or tiny molded mushroom configuration. Likewise, fastener stem preforms may be molded, followed by a "flat-topping" or other forming operations for forming loop-engageable heads. An advantage technique of flat-topping the stems thus formed on a carrier, as described here, is described further below in connection with FIG. 12. In one example the fastening layer 120 is of hooks of CFM-29 designation, available from Velcro USA Inc. of Manchester, N.H., U.S.A. The CFM-29 hooks may be only 0.015 inch (0.38 mm) in height h, with a width w of 0.017 inch, and a thickness T of 0.006 inch. The bands of hooks 125 may have width r as small as 0.022 inch up to e.g., 0.125 inch inch and may be spaced at a distance x, as little as 0.010 inch up to e.g. 0.750 inch apart. The thickness t of the elastic carrier layer may be 0.005 inch. The thickness of the base material b may be 0.003 inch underneath the hook rows, while in the area of the parting regions the thickness may be 0.001 inch, less or completely absent. The parting regions are parallel to the direction of orientation of the crooks of the hook elements and as shown, are formed between every other hook row, i.e. each band 125 of hooks, defined between parting regions, comprises two rows of hooks, 124a and 124b, respectively. In other cases there may be more rows of hooks. In the embodiment shown, between individual hooks 24a and 24b in a band are molded low-elevation formations 127 joined to the sides of stems of respective hooks, serving to strengthen them, in accordance with hook products CFM-29 designation available from Velcro USA.

Either before use or at the time of first use of the fastener, tension is applied along the stretching direction 130, perpendicular to the direction of the parting regions 126 (FIG. 2). The applied tension causes an elongation ($\Delta x$) of the elastic layer 110 and will rupture any material of the fastening layer 120 if it exists at the parting regions 126 (FIG. 2A). When the tension is relaxed the fastener 100 returns to its original dimensions, while any material of the fastening layer 120 that was present along the regions 126 is irreversibly ruptured.

In one embodiment, the elastic layer 110 is composed of a thermoplastic elastomer, e.g., SANTOPRENE® supplied by A.E.S. Corporation., and the fastening layer 120 is composed of a suitable synthetic resin for fastener hooks such as, polyethylene, polypropylene or polyethylene terephthalate (PET).

If a flexible, nonelastic carrier sheet is employed, the sheet is capable of flexing at the cut lines or in the regions between the hook bands to achieve a product of enhanced flexibility.

In the embodiment shown in FIG. 3, the base 122 of the fastening layer 120 is a laminate including a first base layer 121 and a second base layer 123. The first base layer 121 is composed of strong synthetic resin suitable for fastener hooks and is integrally molded with and, preferably, is of the same resin material as the stems of hook elements 124$a$, 124$b$. The base layer 121 in this embodiment is continuous in the direction of the band of hooks, extending in the direction of the arrows as shown, but as shown in FIG. 3, is discontinuous in the normal direction, i.e. the direction of eventual tension 130, or the direction of flexing. The second base layer 123, chosen for compatibility with the resin of layer 121, is composed of an elastomeric resin and has a yieldable or rupturable character. When tension is applied in the stretching direction 130 the second base layer 123 between the bands of hooks expands, or ruptures along lines 132, in either case enabling the fastening layer 120, i.e. the bands 125 of hooks, to follow the stretching of the elastic carrier layer 110 (FIGS. 4 and 4A), (or the flexing of a flexible, but non-stretchy carrier). When the tension is relaxed the laminate fastener 100 returns to its original unstressed dimensions.

In one example, the thickness c of the first base layer 121 is 0.001 inch, and the thickness d of the second base layer 123 is 0.001 inch. The first base layer is composed of polyethylene, polypropylene or PET, the same as that of the stems of the hooks, and the second base layer is composed of a thermoplastic elastomer, such as a thermoplastic polyurethane or an elastomeric copolymer containing PET such as HYTREL® supplied by E.I. du Pont de Nemours and Company, or SANTOPRENE® supplied by A.E.S. Corporation. The second layer 123 may be formed by coextrusion with the resin of base layer 121, and laminated in situ with the elastic carrier material 110. In another case, the second layer 123 may be preformed and introduced into the nip for in situ lamination with base layer 121 as the latter is formed, and the carrier material may be laminated after the hook stems are molded.

Whereas in accordance with the embodiment of FIG. 1, the hook bands due to continuity of the base layer of the hooks, resists elongation of the composite in the direction of the hooks, other embodiments are also possible. In one case, the bases of the molded hook stems are directly laminated to the loop material at the time of being molded, without there being a continuous base layer, or in other cases larger discretely separate islands of hooks can be formed while having limited dimension in both length and width, separated from each other in both, (X and Y) orthogonal directions on the carrier. Thus can be economically formed a composite which has parting or flexing regions arranged in two orthogonal directions, enabling elastic stretching or simple flexing in both of those directions, and hooking capability in strategically selected locations, with economical use of the hook-forming resin. The carrier may be of material much less costly than the resin of which the molded stems or molded hooks are formed.

Referring to the embodiment of FIG. 5, as in FIG. 1, a stretchy fastener 100 features an elastic carrier layer 110 laminated to a fastening layer 120. The fastening layer 120 has a base layer 122 and linear bands 125' of hook elements 124$a'$, 124$b'$, integrally molded with the base layer (FIG. 5A). However, in this embodiment, hook elements 124$a'$, 124$b'$ are oriented, as shown by arrows, to be parallel to the stretching direction 130 (FIG. 5A). In this case, the base layer 122 is continuous in thickness in the direction perpendicular to the direction in which the crooks of the hooks point, to define linear bands 125' of hooks that are relatively inextensible in that direction. Between the hook element bands 125' there are parting regions 126'. The parting regions 126' are formed by grooves leaving the base very thin or nonexistent in those regions, as shown in FIG. 5.

Figure 6A:
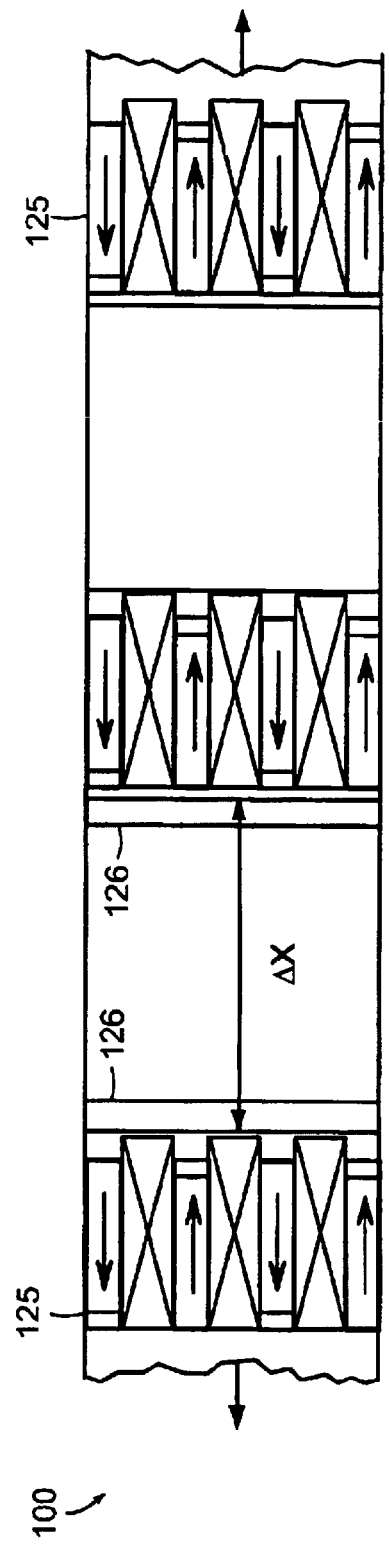
FIG. 6A is a top view of the stretched hook fastener of FIG. 5.

Tension applied along the stretching direction 130 (FIGS. 6 and 6A) and perpendicular to the direction of the parting regions 126' causes an elongation ($\Delta x$) of the elastic layer 110 and rupture of any material of the fastening layer 120 existing at the parting regions 126'. When the tension is relaxed, the fastener 100 returns to its original dimensions, while any material of the fastening layer 120 in the parting regions 126' is irreversibly ruptured.

As in FIG. 5, in the embodiment shown in FIG. 7, the rows of hook elements 124$a'$, 124$b'$ are oriented in opposite sense and parallel to the stretching direction 130, and the relatively inextensible bands 125' of hooks extend in the direction perpendicular to the direction in which the hooks point. The base 122 of the fastening layer 120 is a laminate including a first base layer 121 and a second base layer 123, similar to the construction of FIG. 3. The first base layer 121 is made of strong synthetic resin suitable for fastener hooks and is integrally molded with the stems of hook elements 124$a'$, 124$b'$. The second base layer 123 is made of a less strong material and has yieldable or rupturable character. Tension applied in the stretching direction 130 (FIG. 7A) causes the second base layer 123 to expand or rupture along lines 132, in either case enabling the fastening layer 120, i.e. the bands 125' of hooks, to follow the stretching of the portion of the elastic carrier layer 110. When the tension is relaxed the laminate fastener 100 returns to its original unstressed state dimensions.

Other embodiments include parting lines that are either cut (or perforated) at spaced intervals (FIG. 8) to form weakened lines 126" or in some instances are fully cut through the base 122 of strong forming material.

Figure 8:
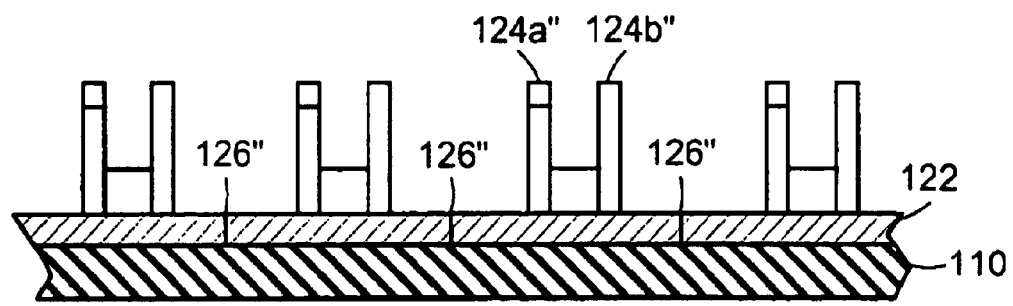
FIG. 8 is a cross-machine direction, cross-sectional view of another embodiment of a stretchy hook fastener according to the invention.
Figure 9A:
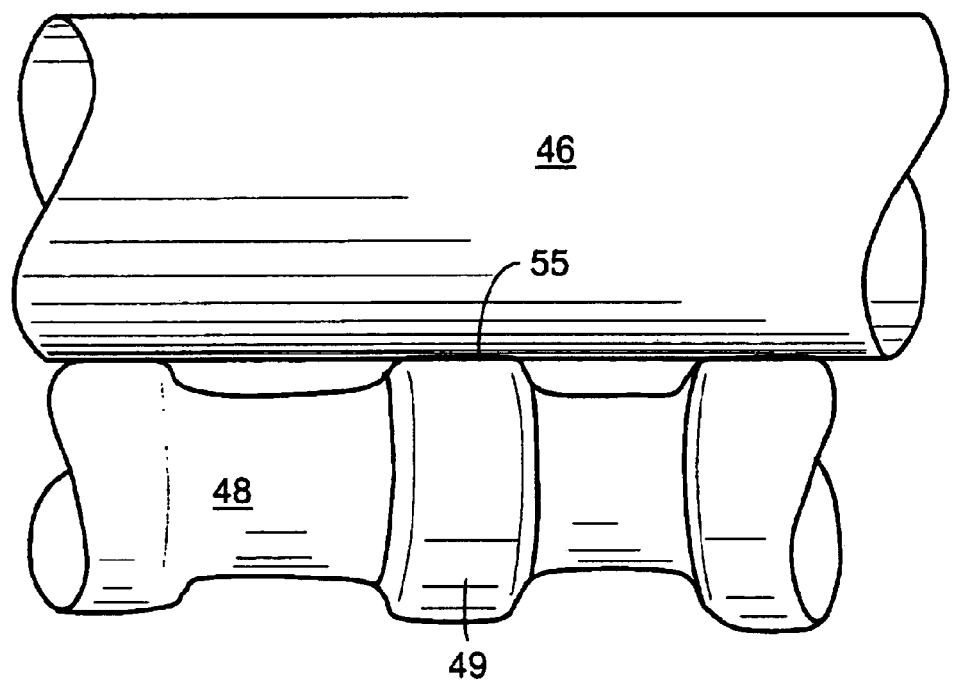
FIG. 9A is a view of the apparatus of FIG. 9, taken in plane 9A—9A.
Figure 9:
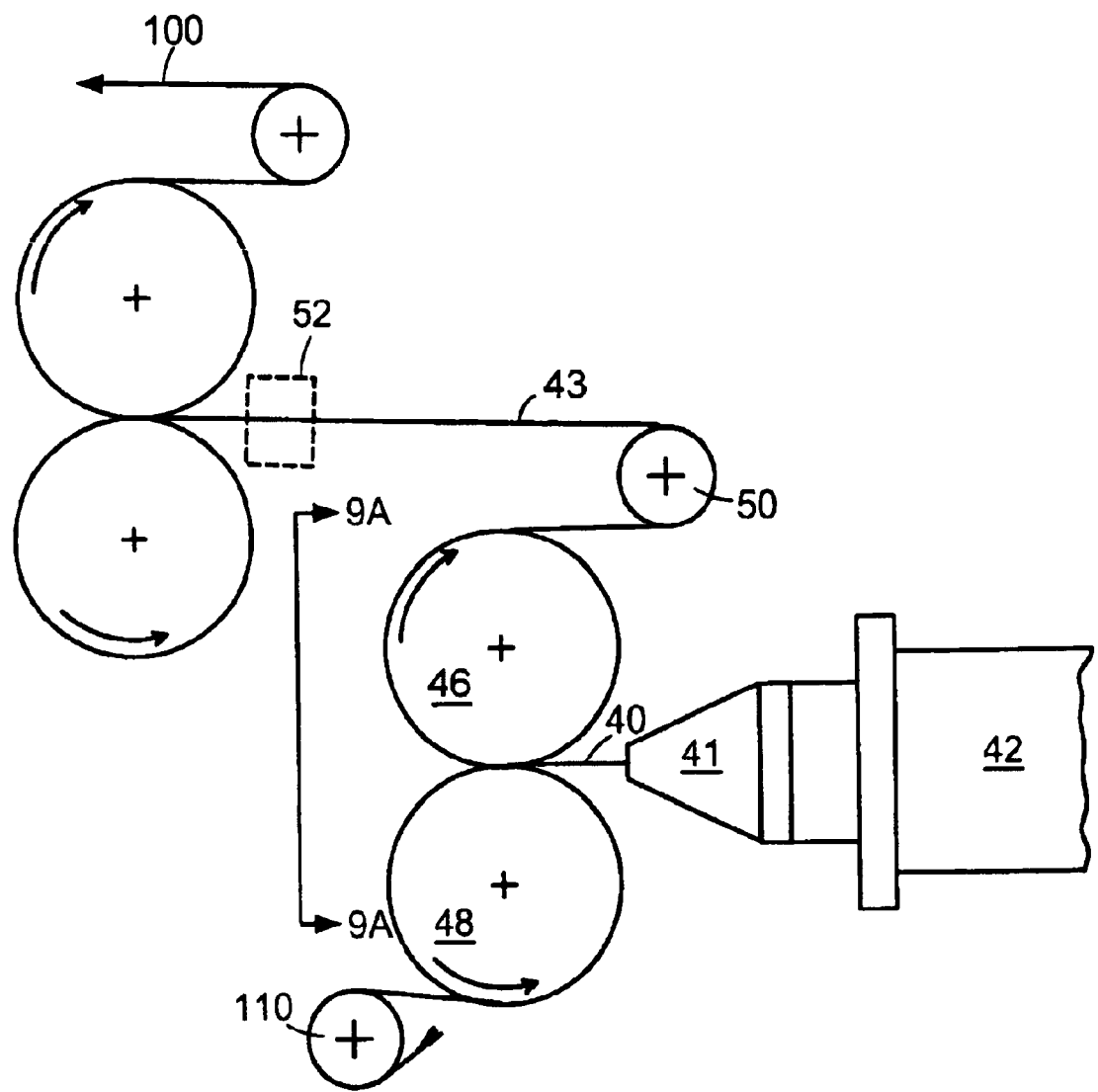
FIG. 9 is a machine direction side diagrammatic view of an apparatus for forming the hook fasteners of FIGS. 1, 5, and 8.
Figure 9C:
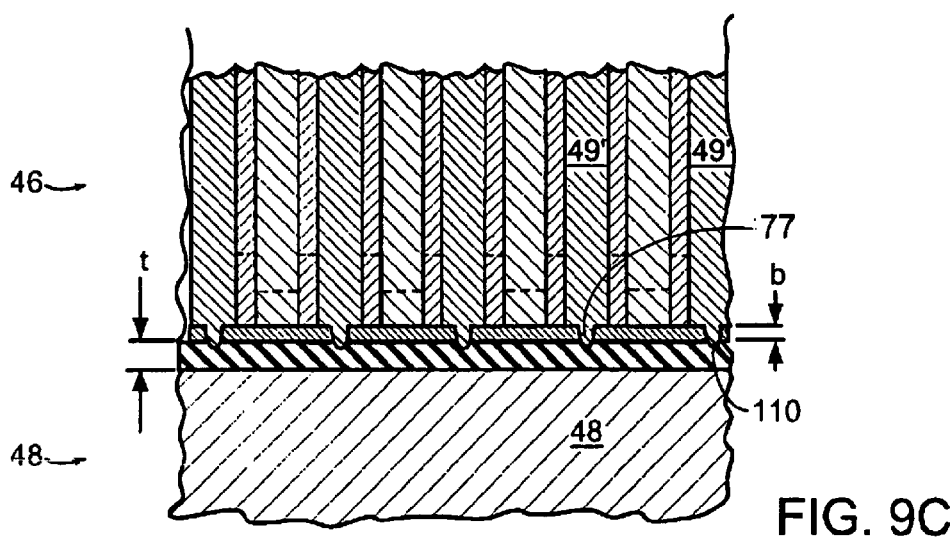

The products of FIGS. 1, 5 and 8 may be economically formed by the process and apparatus illustrated in FIG. 9. Extruder barrel 42 melts and forces the molten plastic 40 through a slot-form die 41. The extruded plastic enters the nip 44 between base roll 48 and mold roll 46, the latter containing mold cavities shaped to form the hooks of a strip-form hook fastener component of the well known hook and loop type (or fastener stems, only, for later forming of loop-engageable features, e.g. by flame heating the distal ends of molded stems followed by engagement with a forming surface such as a cooled bar or a cooled forming roll. Simultaneously with introduction of the molten plastic 40, a pre-formed carrier web 110, which for FIGS. 5 and 8 is at least elastically stretchy in the cross-machine direction, enters the nip 44 and is in situ laminated to the back surface of the hook fastener material, opposite the side on which loop-engageable hooks or stems for such hooks, are being molded. (By "in situ" is meant that bonding action or laminating pressure is applied while the resin is in the mold cavities of the mold roll.) Grooves or interruptions in the base layer of book material are formed between the hook bands during the molding of the hook layer by oversized rings 49 located at spaced apart intervals on the pressure roll (FIG. 9A, or e.g. for forming the product of FIG. 1, by oversized spacer rings 49 between the mold rings 76 which are stacked together along the axis in the conventional way to form the mold roll 46). "Oversize" here refers to rings having larger outer diameter than the outer diameter of the mold rings. The oversize of rings 49' reduces the spacing (in limited regions 55) between the mold roll 46 surface and the pressure roll 48 and causes the plastic resin 40 to form a very thin base layer or a groove in the respective regions of base layer 122. In some cases (see FIG. 9C), according to the invention the oversized rings 49' are adjusted in position closer to the base roll 48 than the thickness t of the preformed elastic carrier such that peripheral portions 77 of the over-size rings indent resiliently the substance of the carrier sheet and prevent entry of molten resin in the corresponding regions. In the alternative of FIG. 9D, the oversized rings 49' themselves are formed of resilient material such as a hard elastomer, and in their peripheral regions 77 the mating portions of the rings and the carrier 110' engage with pressure further limiting or fully eliminating resin from these regions. The carrier 110' in this case need not be elastomeric, and may for instance be a nonwoven loop material or other flexible sheet.

Figure 9B:
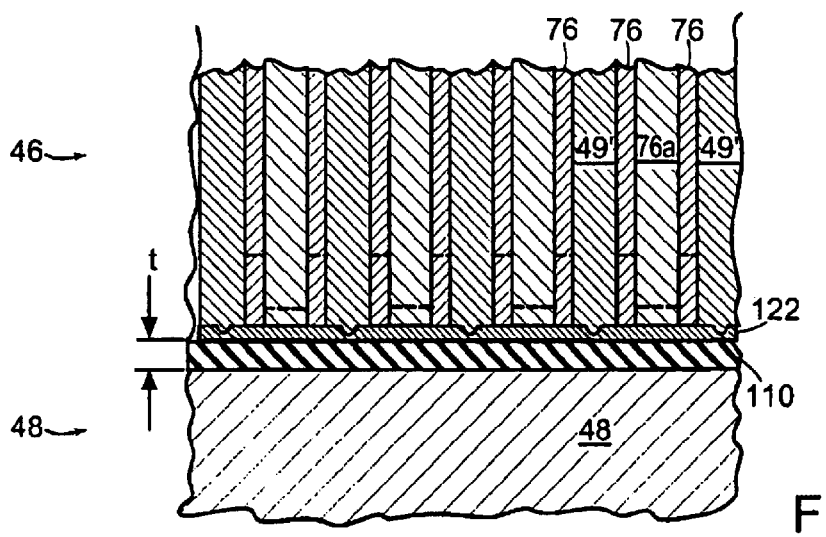
Figure 9D:
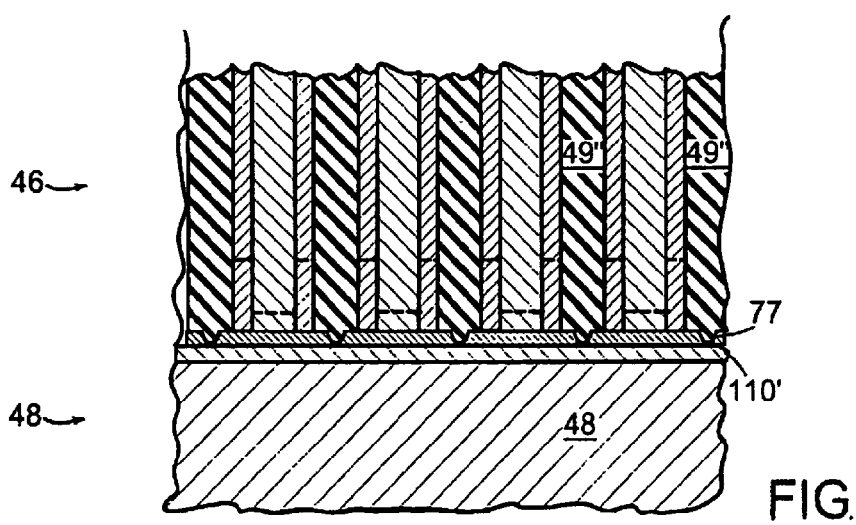
Figure 9G:
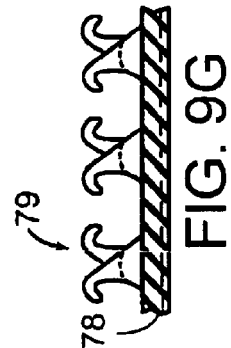
FIGS. 9F and 9G are transverse and longitudinal cross-section views, respectively, of a product formed with the apparatus of FIG. 9E.
Figure 9F:
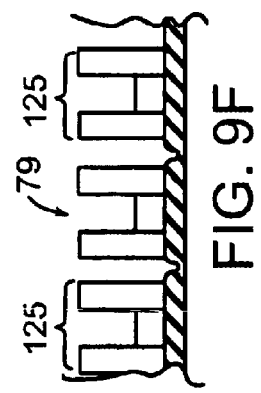
Figure 9E:
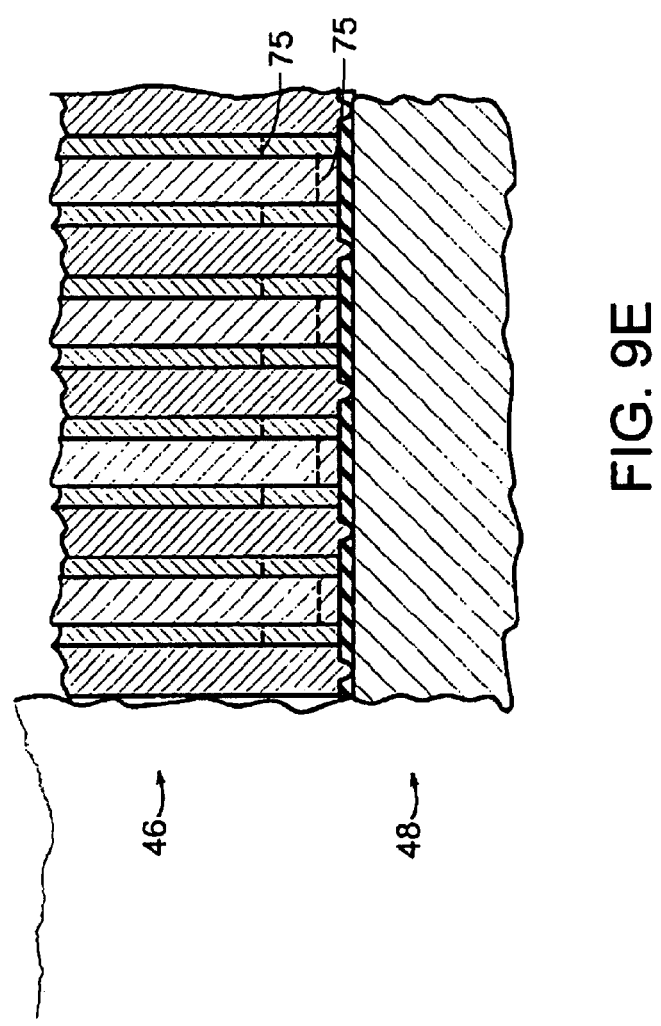
Figure 9H:
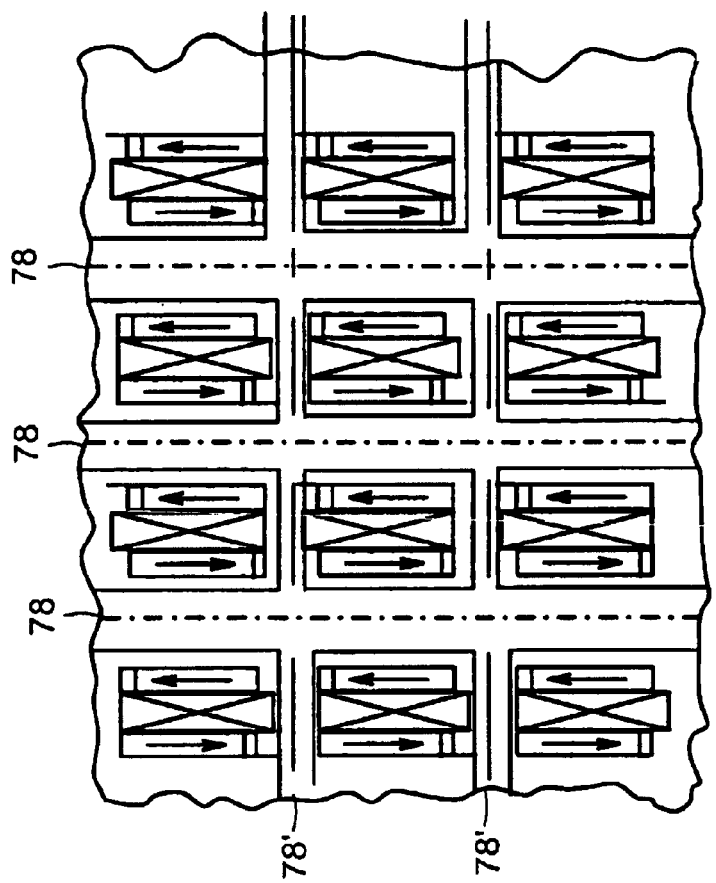
FIG. 9H is a plan view of a hook sheet, which is flexible in orthogonal directions.

As illustrated in FIG. 9E, the apparatus of FIG. 9B can be used to advantage in forming a one-component hook sheet 79 which has thinned flexure regions 78 between bands 125 of hooks. In this case, resin 40 (e.g. in this case, polypropylene for forming "living hinges") from extruder 42 fills hook mold cavities 75 and the entire gap between the mold roll 46 and the pressure roll 48, no pre-formed sheet being introduced to the mold gap. The resulting product can have enhanced flexibility in the cross machine direction by the cooperation of the many living hinges alternating with the bands of hooks. Similar flexure regions 78' can also be formed extending cross machine by suitable cross machine protrusions from the mold roll, see FIG. 9H, resulting in islands of molded hooks connected to each other by thin flexures of the hook-forming resin, the size of the island depending on the spacing and width of the oversize forming rings and axially extending forming protruding ridges or other features employed to define the islands.

Figure 9I:
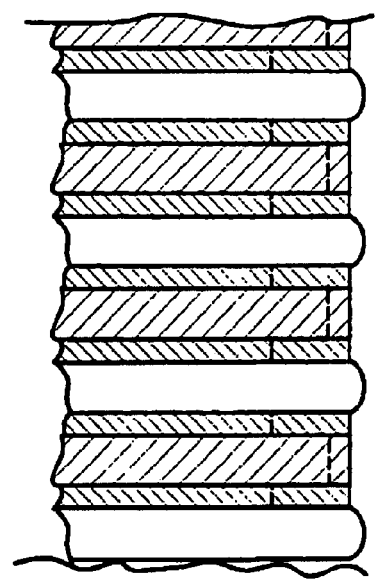
FIG. 9I is a cross-section of part of another mold roll configuration.

FIG. 9I shows an alternate form of the peripheral edges of the "oversize" spacer rings, adapted to form larger parting or flexural regions.

Referring again to FIG. 9, to form the cut parting lines 126" of the embodiment in FIG. 8, the hook fastener with the laminated elastic web 43 travels around the periphery of mold roll 46 to stripping roll 50, and into a slitter 52 (shown in dashed lines), which in this case, is provided. The slitter 52 has multiple spaced apart blades to slit the laminate hook strip 43 in-between every hook band. The finished product 100 goes from there to a windup device, not shown.

Figure 10:
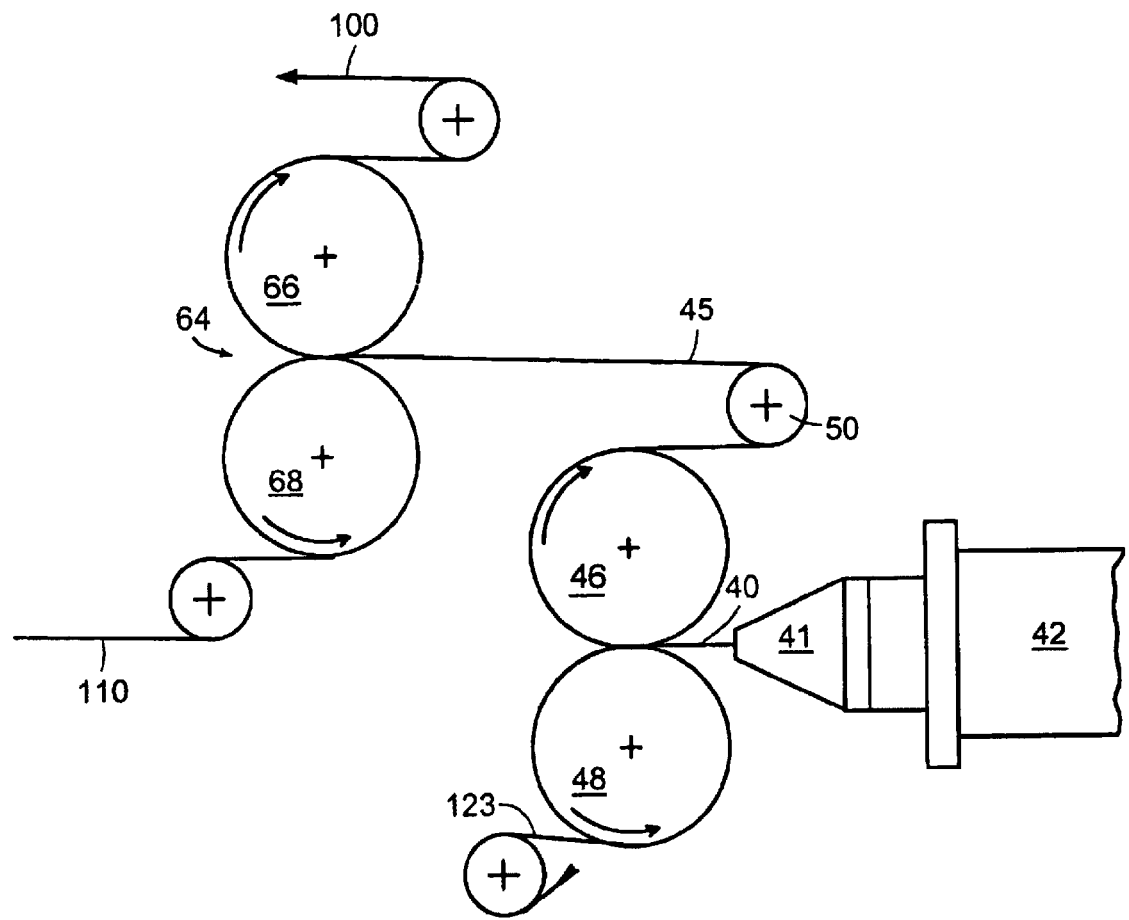
FIG. 10 illustrates an apparatus for forming the hook fasteners of FIGS. 3 and 7.

Referring to FIG. 10, to form the double base layer for the products of FIGS. 3 and 7, a preformed web for the second base layer 123 is led into the nip 44 between the mold roll 46 and base roll 48 and is in situ laminated to the back of the formed first base layer 121 with the integral hooks 124 (FIG. 10). The formed hook fastener with the two base layers 45 is then fed into a nip 64 between two heated rolls, 66 and 68, together with the elastic carrier web 110. The elastic carrier web 110 is thermally fused or otherwise adhered to the back of the second base layer 123, so that layer 123 effectively forms part of the sheet-form carrier. Alternatively, this second lamination occurs in situ, i.e. in the region between nip 44 and take-off roll 50 while the molded hooks remain in their mold cavities. This can be accomplished either by applying a layer fresh from a second extruder, or by flame, adhesive or other lamination of a pre-formed sheet led from a supply roll.

For more detail about the operation in general, of an in situ lamination apparatus the reader is referred to U.S. Pat. No. 5,260,015 to Kennedy, et al., which discloses laminates of various materials, and to U.S. Pat. No. 5,441,687, to Murasaki et al., which discloses another form of in situ lamination, i.e. lamination which occurs while hooks being formed are still in their mold cavities.

Figure 11B:
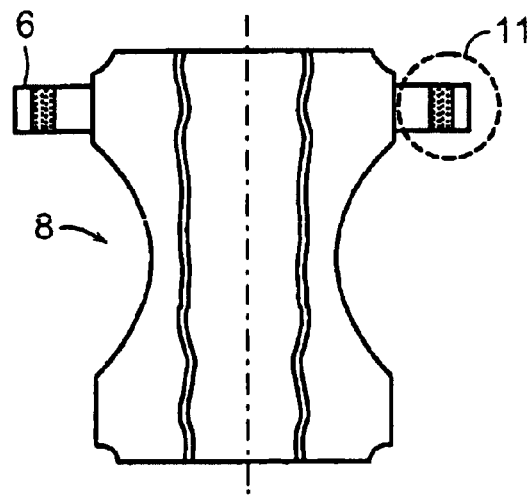
FIG. 11B is a top view on a larger scale of a diaper with a stretchy diaper tab, indicating, by a circle, the place of the view of FIG. 11.
Figure 11:
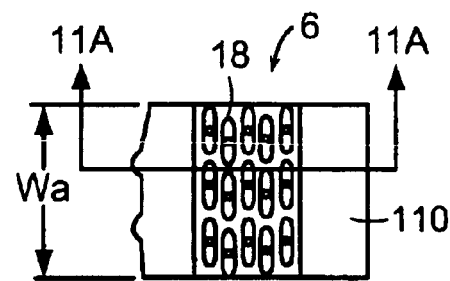
FIG. 11 is a top view of a stretchy diaper tab.
Figure 11A:
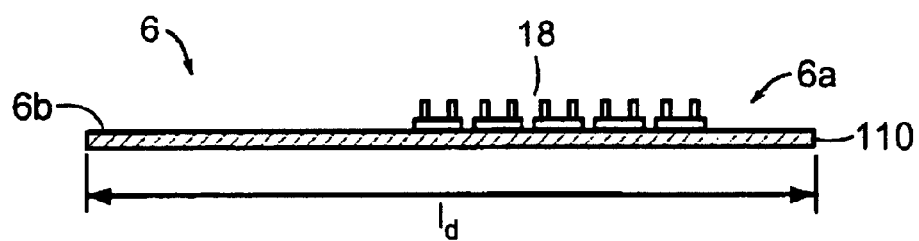
FIG. 11A is a cross-sectional view of the diaper tab of FIG. 11 taken in plane 11A—11A.

One of the many applications of a stretchy or flexible fastener as disclosed is as a stretchy or flexible diaper tab. Referring to FIGS. 11, 11A and 11B, a stretchy diaper tab 6, for instance, has a stretchy fastener 18 and an elongated elastic layer 110 extending beyond the stretchy fastener area 18. One end 6b of the diaper tab 6 is attached to a diaper 8 to form part of a hook and loop type closure. A second end 6a is used for grasping the diaper tab. The stretchy diaper tab has a width ($W_d$) 1 inch, and a length ($l_d$) of 2 inch.

Other features and advantages of this aspect of the invention may include one or more of the following. The elastic or flexible carrier web 110 may be post-laminated by thermal fusion or ultrasonic welding to a pre-formed fastener hook layer. In the embodiment of FIG. 3 the second base layer 123 may include weakened lines (not shown) and the weakened lines may be cuts. The elastic or flexible carrier layer 110 may also be a nonwoven material.

Since the bands of hooks are relatively inextensible, and lie normal to the direction of tension, the width of these bands relative to the width of the parting region determines how much of the elasticity or flexibility of the carrier is neutralized by the laminated hook resin. Accordingly, various degrees of extensibility or flexibility of tabs, straps, ties or wrappings formed by the process described can be achieved even by using the identical thickness and properties of the resin for the carrier. It is simply necessary to change the relative widths of hook bands and intervening resin-free bands for a given length of carrier material.

An important further aspect of the invention is the introduction of hook-forming molten resin to a mold roll in multiple, discrete bands along the roll spaced further apart than illustrated, e.g., in FIG. 1 or FIG. 3 to register with corresponding bands of hook mold cavities in the mold roll, thereby forming multiple, parallel but further separated bands of hook material laminated to a stretchy or flexible carrier, which may be the material, e.g., from which a diaper tab is formed. This material may be slit in various ways to form useful stretchy or flexible fastener products.

Aspects of the invention are further illustrated in application to a so-called wrap tie in which a stretchy material is an elastically stretchy hook-engageable loop material.

Figure 12:
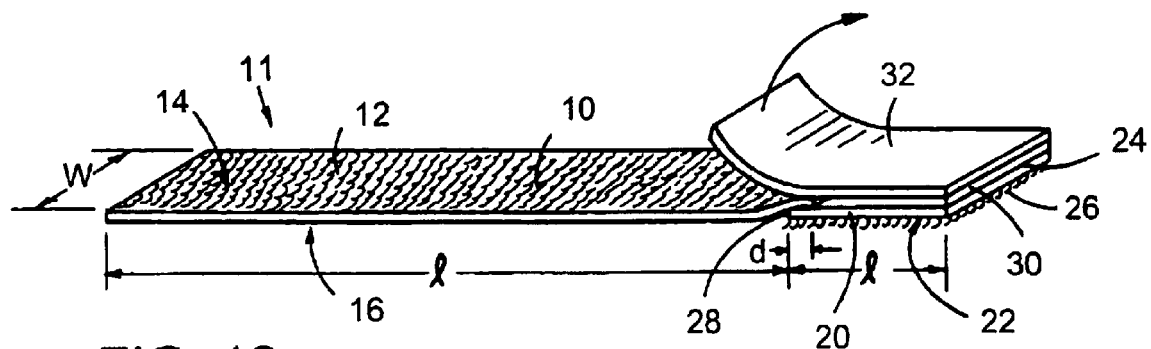
FIG. 12 is a perspective view of a wrap tie having an elongated loop component overlapping and in situ laminated to a short hook component and adapted for permanent union with a bag or similar article.

Referring to FIG. 12, a wrap tie 11 features an elongated strip of stretchy nonwoven loop material 10, attached to a short strip of hook material 20.

The strip of nonwoven loop material has a first surface 14 with hook-engageable loops 12 and a second relatively smooth surface 16. The strip of hook material 20 has a first surface 22 with integrally molded fastener elements 26 and a second smooth surface 24. The fastener elements may be, e.g., single crook hooks, palm tree-shaped hooks, or hooks of mushroom shape. The strip of hook material 20 can be initially formed with integral molded stems only, the loop engaging head shaped formed subsequently. An example is by flat-topping the stem to form a mushroom shape, e.g. by the advantageous use of a flame of burning gas jets to rapidly soften the extreme ends of the stems, followed by engagement by a cooled forming bar or a forming roll, such as is described in PCT EP 00/00329, the entire contents of which is hereby incorporated by reference. The smooth surfaces of the hook and loop strips overlap distance d and are attached at joint 28 so that the loops and hooks extend in opposite directions of the wrap tie. A pressure sensitive adhesive layer 30 covers the remainder of the smooth surface 24 of the hook strip 20. For a face-to-face attachment of the hook and loop strips (FIG. 1F), i.e., attaching the surface of the loop strip having the loops to the surface of the hook strip having the hooks, the base portion of the hook strip 20 has an integral extension 29 without hooks for overlapping the loops of the loop strip 10. The pressure sensitive adhesive layer 30 is covered with a release liner 32, such as silicon-coated paper. The release liner 32 overlaps longitudinally the loop component such that a portion of the release liner is exposed for grasping. In one example, the tie is 0.5 inch wide, dimension w, the loop strip is 3 inch long, dimension I, the hook strip is 0.75 inch long, dimension 11, and the overlap area 128 is 0.4 inch long, dimension d, all components having the same width w. The thickness of the loop material may vary between about 0.150 inch and 0.0100 inch, and the thickness of the hook material may vary between about 0.100 inch and 0.010 inch. For further description of such products, reference is made to U.S. Pat. No. 6,205,623 filed Nov. 6, 1998 (of which this application is a continuation in part), which is incorporated by reference.

Figure 12A:
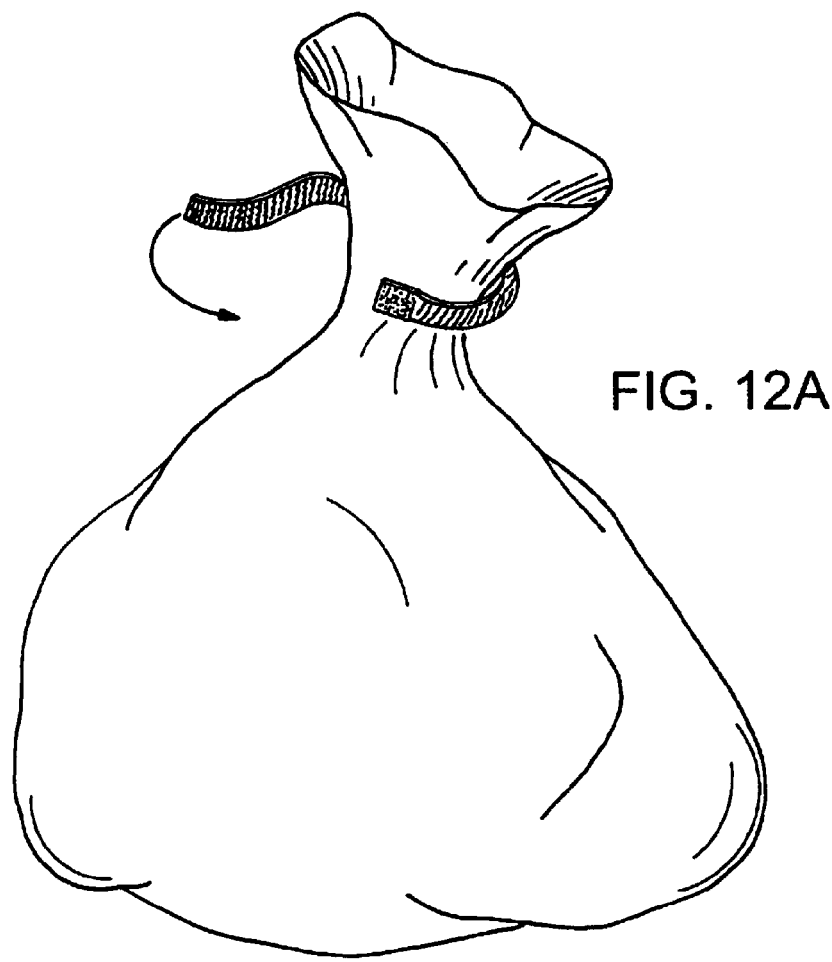
FIG. 12A is a perspective view of a bag having the wrap tie of FIG. 12 attached to its surface.

Referring to FIG. 12A, the wrap tie of FIG. 12 is attached to an open end of a bag by the adhesive layer. The elongated nonwoven loop strip is wrapped around the bag opening and the free end of the loop strip is secured to the hook strip by engaging the loops with the hooks. The wrap tie may be pre-fastened and integrated with the bag, e.g., during manufacture of the bag, or it may be applied to the bag at the time of its use, by removing the release layer and pressing the adhesive component against the material of the bag. The bag may be made of synthetic resin or paper. In some instances the wrap tie may have, instead of the pressure sensitive adhesive layer, a synthetic resin layer which can be thermally fused to the bag surface.

In such applications in which the products are considered disposable after single use, the loop material only need withstand a relatively small number of hooking cycles (e.g., 3 to 5) over the product's useful life. We refer to these as "low cycle" applications. Loop products in this category may be fabricated to advantage with needled fabric that has needle-formed loops on one or both sides. In certain cases, the material is in a permanently stretched and stabilized state, having been stretched to increase its area at least 20%, preferably in excess of 100%, as much as 150% or more from its as-needled condition. A preferred needled and stretched material is formed of staple polyester yarns of between about 18 and 4 denier, preferably 6 denier. Where it is desired that the loop material be stretchy, the needled material is rendered stretchy by confining the stretching to one direction, for instance the machine direction (while the web in the orthogonal direction is relaxed and permitted to neck in), and stabilizing the thus-stretched fabric with a binder that has sufficient elastomeric properties which, while stabilizing the product in the direction it has been stretched, substantially preventing elastic return in that direction, still permits elastic stretching of the material in the direction perpendicular to the direction in which it has been stretched and stabilized. An example of such a binder is the class of binders available from BF Goodrich Co. under the mark HYSTRETCH®, e.g., grade V-43.

A more complete description of the process employed (except details of the one-direction feature of forming stretchy products is not described) may be found in U.S. Pat. No. 6,329,016, entitled Loop Material For Touch Fastening, filed Mar. 3, 1999, disclosure of which is hereby incorporated by reference.

Other applications, such as strapping or bundling, may require the hook-engageable loops to withstand a higher number of cycles and higher stress. These relatively "high cycle", high strength applications generally are preferably achieved by using suitably elastic woven or knitted material, or in a needled nonwoven as above, by forming loops with higher denier (or higher tenacity) fibers than those suitable for lower performance conditions, or by using a heavier weight of material or needling the material at greater intensity, all according to known techniques, selected in accordance with the properties required for the particular application at hand. Loop products in this category may be prepared by stretching an appropriate needled loop fabric in the range of 50 percent to 100 percent stretch, for example, followed by stabilization. In certain cases, advantageous effects of the invention can be obtained by stretching down to a lower limit of about 20%.

For certain applications, specially treated loop material may be used in a wrap tie. For example, on a bag that holds an electronic device and needs to dissipate static electricity, nonwoven loop impregnated with carbon or stainless steel or other conductive material may be used. Carbon or stainless steel fibers may also be blended with staple fiber to form a static electricity dissipative nonwoven loop material. A two-sided nonwoven loop material may be used on a wrap tie so that, no matter if twisted to any orientation, can be fastened to the hook.

Figure 12B:
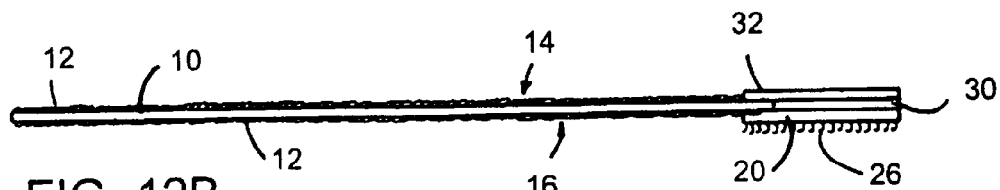
FIG. 12B is a side view similar to FIG. 12 of a wrap-tie having loops on both sides of an elongated loop component.
Figure 12C:
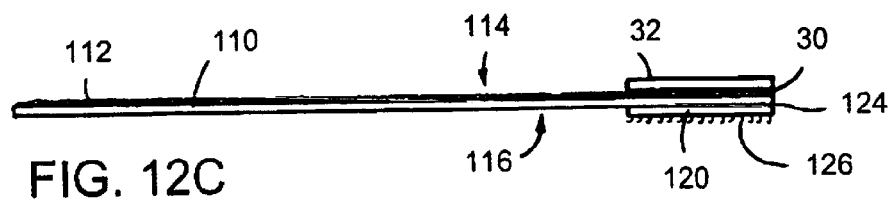
FIG. 12C is a side view similar to FIG. 12B, of a wrap-tie having an elongated loop component, an end portion of which overlaps and is in situ laminated to the entire back surface of a hook component.
Figure 12D:
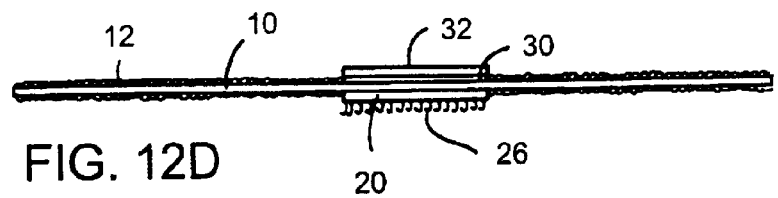
FIG. 12D is a side view of a wrap-tie in which a hook component is in situ laminated to the middle of an elongated loop component.
Figure 12E:
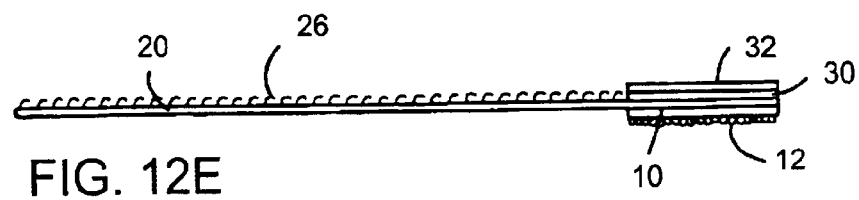
FIG. 12E is a side view of a wrap-tie in which an elongated stretched hook component overlaps and is in situ laminated to a short loop component.
Figure 12F:
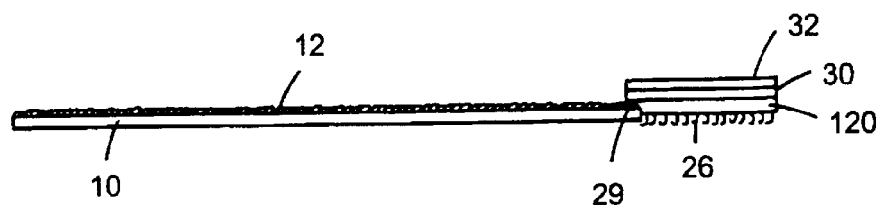
FIG. 12F is a side view of a wrap-tie in which a hook strip is attached face-to-face to the loop strip.

Additional configurations of a wrap tie include among others the following: the stretchy loop strip 10 has loops on both surfaces 14 and 16 (FIG. 12B), the loop strip 10 overlaps and attaches to the entire back surface 24 of the hook strip 20, with the adhesive layer 30 being intimately bonded to the loop side 14 of the strip (FIG. 12C), the hook strip 20 attaches across its entire back to the middle of the loop strip 10 (FIG. 12D), and an elongated hook strip 20,which may be of formed and stretched material is attached to a short loop strip 10 (FIG. 12E).

In preferred embodiments, the nonwoven loop material 10 (FIG. 12) is very thin, but still self-supporting, and has relatively free fibers forming loops extending from one side or both sides of a continuous, tangled mat of fibers. In preferred embodiments the nonwoven loop material 10 comprises a needled fabric of staple fibers which has been stretched longitudinally and stabilized, to form a stretchy fabric of the form depicted in FIGS. 13A and 13B, see U.S. Pat. No. 6,329,016 referenced in the preceding description. In such a fabric the individual fibers of the mat follow no definite pattern as in a woven product, but extend in various directions within the plane of the fabric mat, albeit because of the predominance of stretching in one direction, the fibers are predominantly aligned in that direction and offer little resistance to stretching in the perpendicular direction. The loops that extend from the loop product are of the same fibers that comprise the mat but extend beyond the general mass of the mat, out of the plane of the mat, generally from associated knots 180, in the form of well anchored loop trees 250 (FIG. 13C).

Figure 13A:
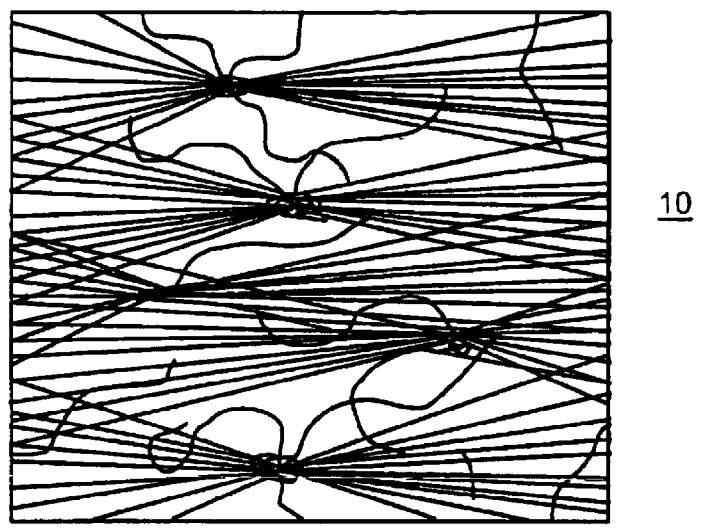
FIG. 13A is a diagram of the face of a preferred nonwoven loop material for use as a loop component, enlarged 50×.
Figure 13B:
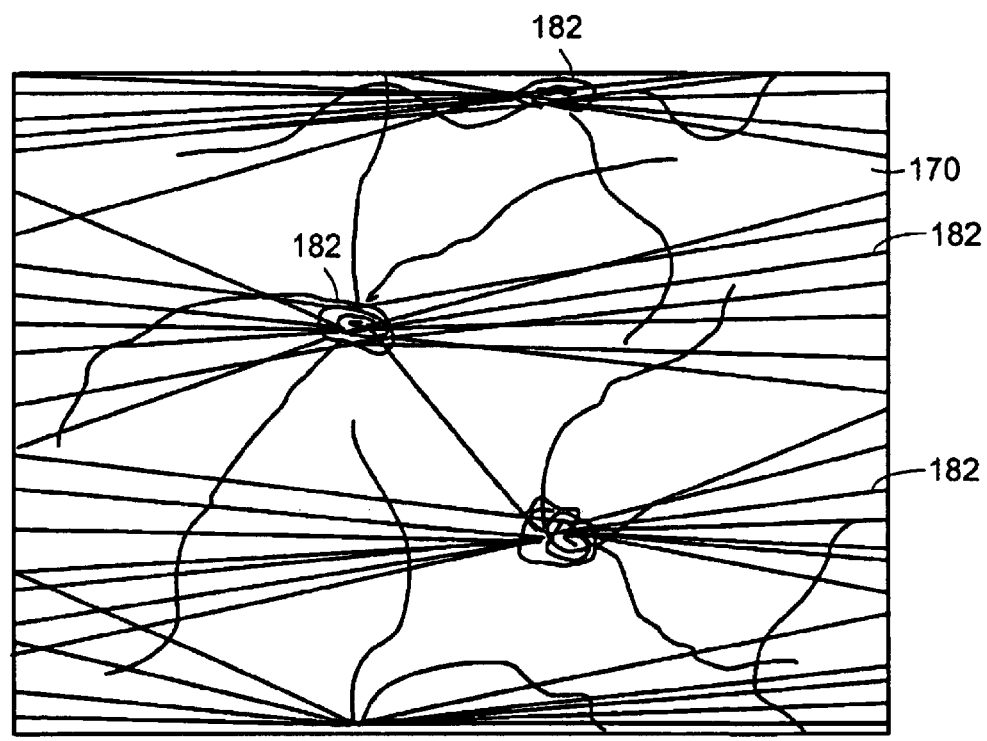
FIG. 13B is a still further enlarged schematic view of the face of the nonwoven loop material shown in FIG. 13A.
Figure 13C:
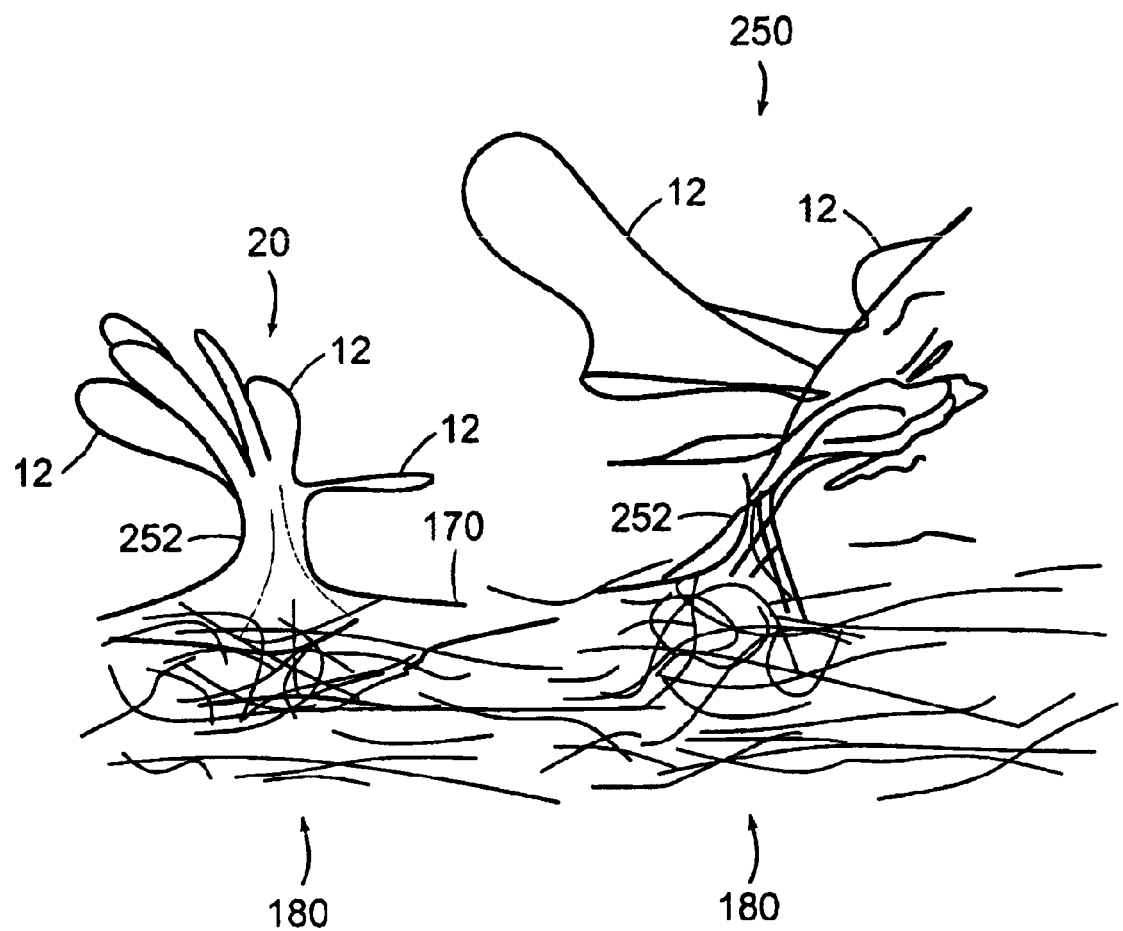
FIG. 13C is a sketch sideview, on a still further enlarged scale of the nonwoven material of FIGS. 13A and 13B illustrating clusters of loop fibers extending from a fibrous mat.

As shown in FIG. 13A, and the magnified illustration of FIG. 13B, in relatively low density fiber regions of a preferred mat a substantial number of the fibers of the mat of loop material 10 are taut (i.e., not slack, regionally straight), and extend between knots 180 of the loop material fabric in the direction of the pre-stretching. The taut fibers 182 have been straightened by tension applied in one direction in the plane of the fabric mat 170, while the knots have been produced by slippage and agglomeration caused during the application of stretching forces to the needled nonwoven fabric.

The knot density of the sample may be 180 knots per square inch. The knots themselves may be fairly tight, made up of several monofilament fibers, and are interconnected by the taut fibers seen running between them. Between knots, the thin fiber mat may not be very dense and may be sheer enough to permit images to be readily seen through it. For low cost applications, the fabric preferably weighs less than about 2 ounces per square yard (68 grams per square meter).

In particular embodiments in which the loop material is to serve as a stretchy or flexible carrier, the fibers of the mat are held in their taut, straightened condition by an elastomeric binder (not shown) applied as a fluid to the side of the mat opposite the loops to bind the mat fibers in their straight condition to stabilize the lengthwise dimension of the fabric, and to secure the loops at their associated knots. The binder generally ranges between 20 and 40% of the total weight of the fabric and in the presently preferred embodiments accounts for about one third of the total weight of the loop component. The resulting fabric is dimensionally stable and strong enough to be suitable for further processing by standard fabric-handling techniques. If, depending on choice of binder and other parameters, the fabric has a slight stiffness, like a starched felt, the stiffness can be mitigated where desired by additional softeners or mechanical working of the formed fabric as by microcroping using machines from Micrex, Inc. of Walpole, Mass.

As seen in FIG. 13C, loops 12 extend from freestanding clusters of loop fibers extending from the fibrous mat 170. The clusters 250 which have several monofilament loops 12 extending from a common elongated, substantially vertical trunk 252 we call "loop trees". Each loop tree 250 extends from a corresponding knot 180 in which the loops of the cluster are anchored. Interstices between individual filaments in the trunk portion 252 of each tree or at the base of each bush, and in each knot 180 provide paths for the wicking of liquid binder, under the influence of surface tension of the liquid binder, to provide additional localized stiffness and strength. Importantly, the density of clusters in the plan view is very low, leaving sufficient room between the "branches" of neighboring trees to accommodate hooks and deflected loop material during engagement.

Figure 43:
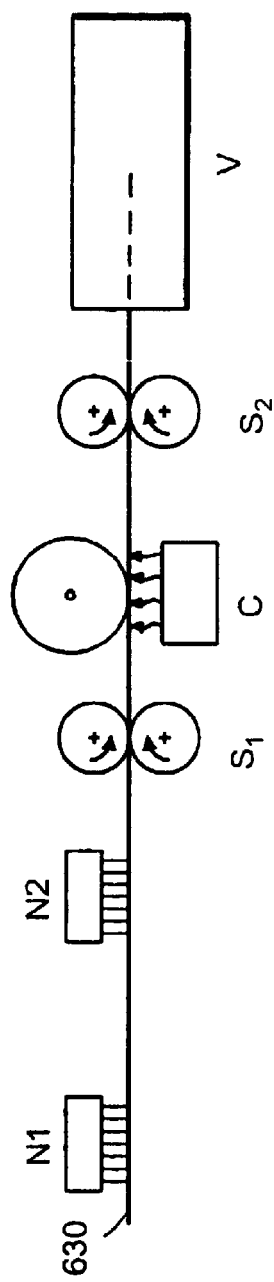
FIGS. 43 and 44, illustrate in side and plan views, respectively, a method and apparatus for forming a novel needled stretchy loop material.
Figure 44:
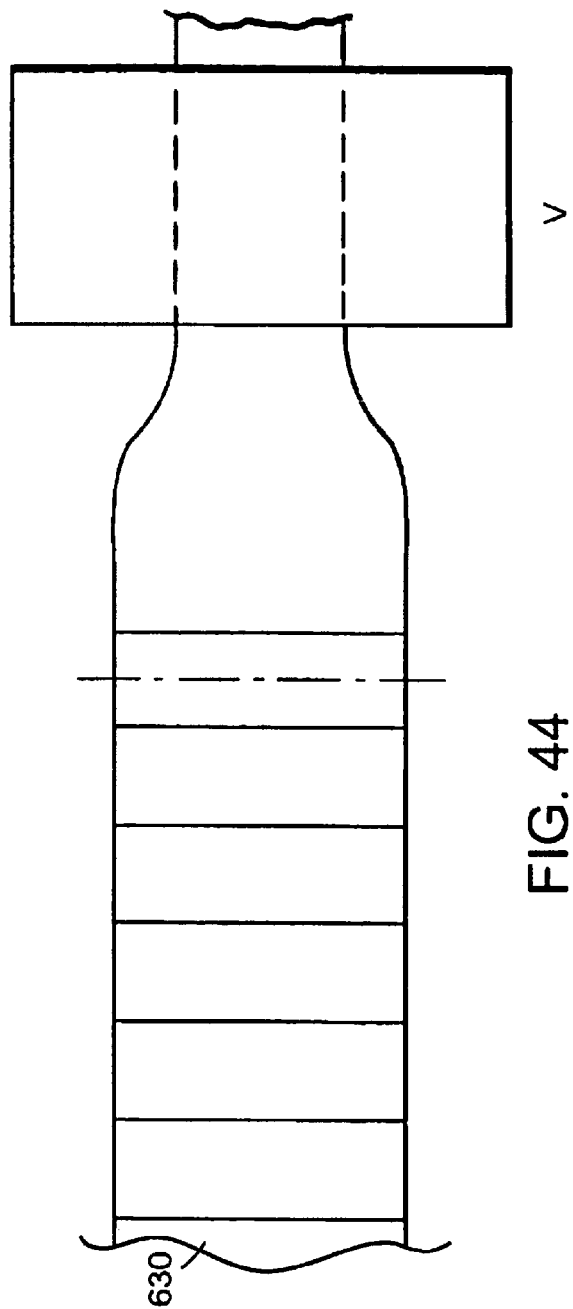

See FIGS. 43 and 44 and related text for a description of the method of forming.

Figure 14:
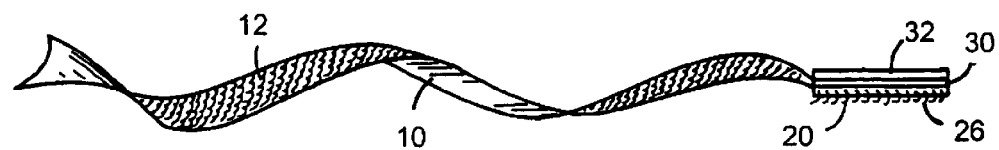
FIG. 14 is a side view of a twisted wrap tie according to the invention.

Referring to FIG. 14, the flexibility of the nonwoven material 10 allows it to be twisted several times and fastened on the hook fastener strip 20. Even if there are loops on only one face of the strip, hook-engageable loops occur at all quadrants of the twist, to ensure engagement with the hook component. Further the loops around the slit edges of the loop strip are oriented in line with the fibrous mat 170, making the edges hook-engageable.

Figure 15A:
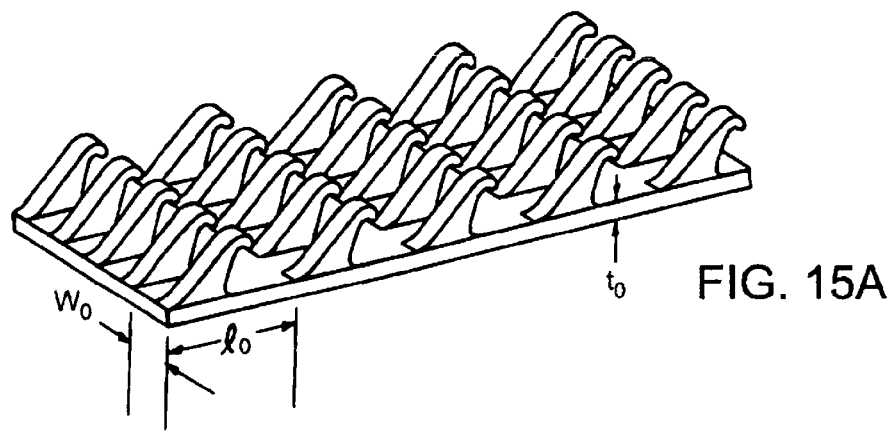
FIGS. 15A and 15B are perspective magnified views of portions of a hook fastener and a stretched hook fastener, respectively.
Figure 15B:
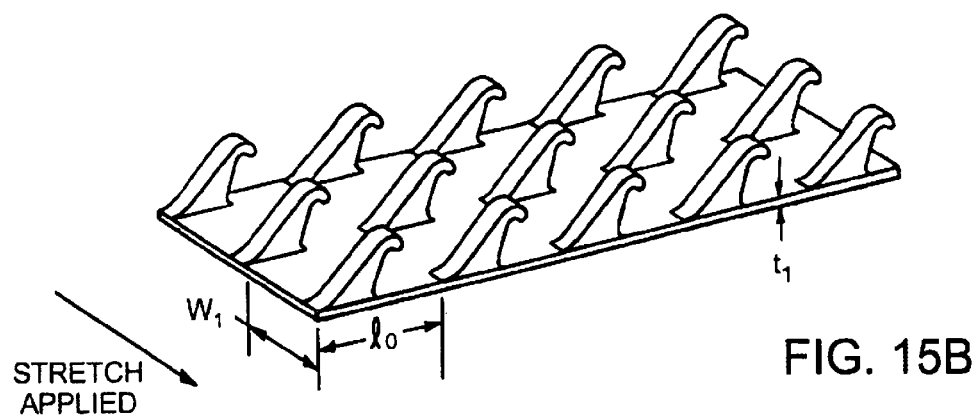

A hook strip 20 compatible with the loop material is used. For a nonwoven loop material made from staple polyester fibers having a denier of 6, a hook may be of the CFM-29 designation, available from Velcro USA Inc. of Manchester, N.H., U.S.A., described above. The CFM-29 hook strip has hooks of only 0.015 inch (0.38 mm) height. Especially when the hook component is the elongated component as depicted in FIG. 12E, the hook strip may be a pre-stretched and stabilized hook product. Referring to FIGS. 15A and 15B, when a hook product is subjected to lateral pre-stretching, the material of the base web decreases in thickness, from the original thickness $t_0$ of FIG. 15A to the reduced thickness $t_1$ of FIG. 15B. The areal density of the fastener elements is accordingly reduced. For example, with hook-form elements of a type having a conventional height of about 0.035 inch and a spacing of about 0.050 inch along the rows, starting with a spacing of the rows of about 0.025 inch and ending with a spacing $w_1$ of FIG. 15B of about 0.100 inch, the areal density changes by a factor of 4, from about 800 fastener elements 11 per square inch to about 200 fastener elements per square inch. Starting with higher hook densities, higher final densities can be achieved to match the hooking needs of particular applications, while still of low cost.

Figure 16:
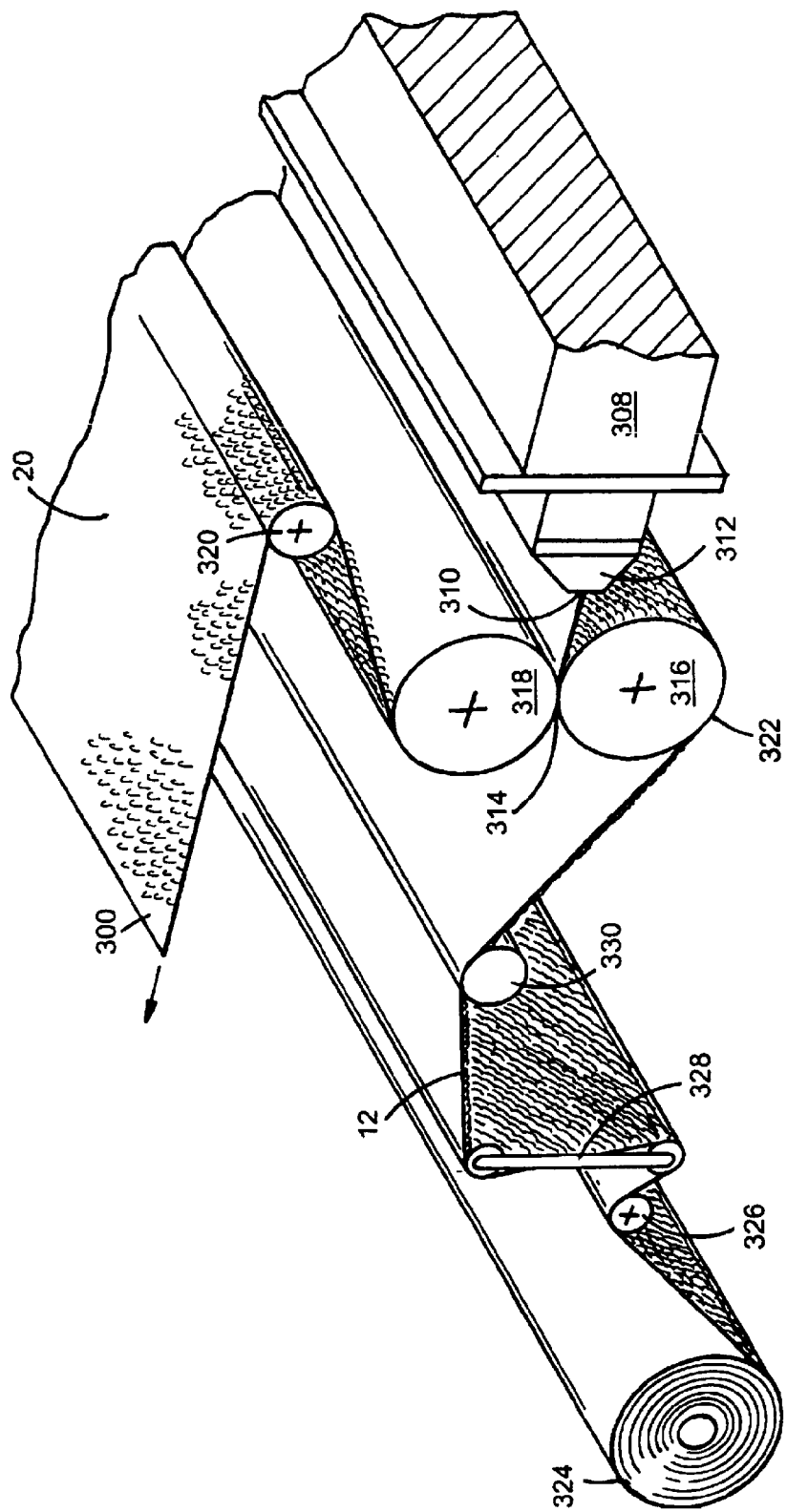
FIG. 16 illustrates an apparatus for forming and uniting components of a wrap tie or other product of the invention.

The product of FIG. 12 is economically formed by the process and apparatus illustrated in FIG. 16. Extruder barrel 308 melts and forces the molten plastic 310 through a slot-form die 312. The extruded plastic enters the nip 314 between base roll 316 and mold roll 318 containing mold cavities shaped to form the hooks of a strip-form hook fastener component of the well known hook and loop type. The strip fastener material formed in nip 314 travels about the periphery of mold roll 318 to stripping roll 320, which assists in pulling the finished product 300 from the mold roll, and from there to a windup device, not shown.

For more detail about the general operation of apparatus such as that of FIG. 16, the reader is referred to U.S. Pat. No. 6,174,476, entitled, Molding Fastener Products Having Backings, filed Sep. 11, 1998, which discloses full width laminates made with loop materials.

An alternative process and apparatus for forming products such as that of FIG. 12 employs an extruder barrel having a contoured injection head arranged adjacent a mold roll to provide a forming nip without the use of a pressure roll. For more detail about the general application of such an apparatus, the reader is referred to U.S. Pat. No. 5,441,687 issued to Murasaki, et al., mentioned above, the entire contents of which are hereby incorporated by reference.

There are many possible methods of feeding the nonwoven sheet material to the forming section of the hook forming device or otherwise combining it with the hook elements. According to another aspect of the present invention, it has been realized that a special relationship of the nature and orientation of a stretchy carrier or loop material to the machine, can lead to simple and reliable production of high quality stretchy products at relatively low cost. It is realized to be highly advantageous to provide, as the stretchy material, a material that is stretchy in only one orthogonal direction, with the direction in which the material is stretchable lying in the cross-machine direction. Under these conditions, suitable machine direction tension can be maintained on the material to ensure that it tracks well to the machine, and that it can be removed from the machine without undue concern as to the complete solidification of the resin, or risk that the web will wander from its desired track or wrinkle or otherwise distort. This can enable high speed, efficient production of high grade products. Accordingly, the stretchy needled loop product described above, and other materials described herein which are stretchy width-wise but resistant to elongation lengthwise, can be used to advantage.

Figure 17A:
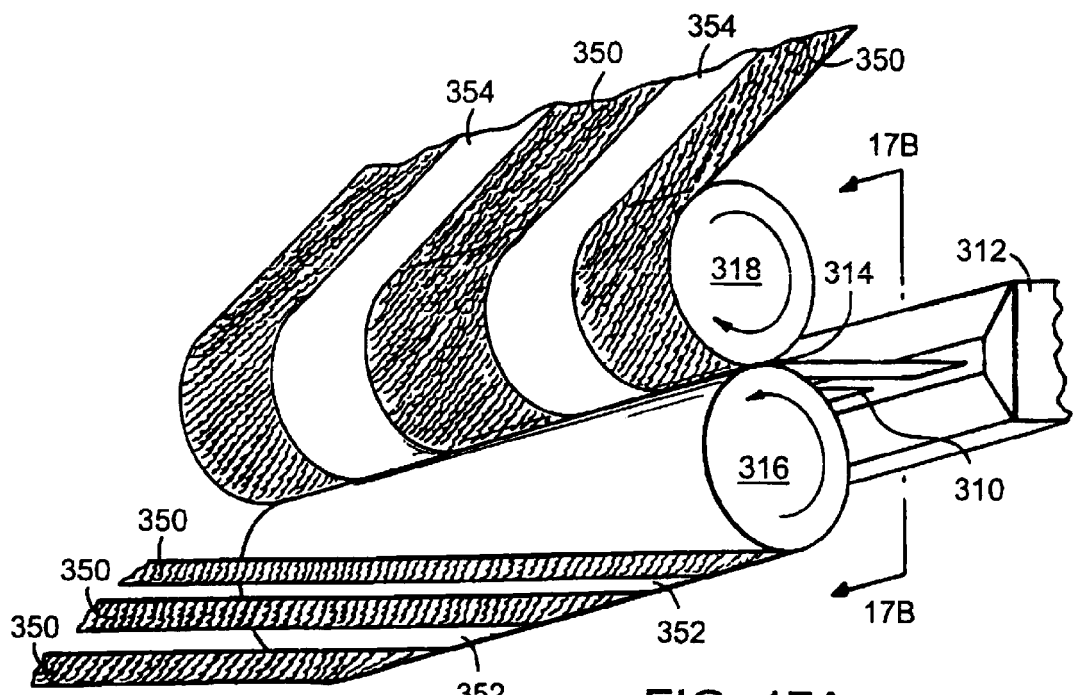
Figure 17B:
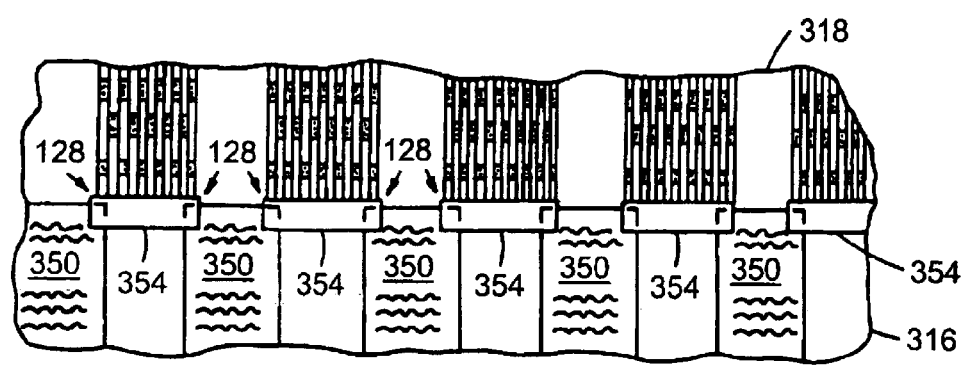
FIG. 17B is a view taken in plane 17B—17B of FIG. 17A.

For forming, e.g. the product of FIG. 12, in one example, shown in FIGS. 17A and 17B, several transversely spaced apart bands of nonwoven material 350 are introduced about the periphery of the base roll 316 and enter nip 314 at the same time molten plastic 310 enters the nip at regions between the bands of loop material. The slot-form die has alternating plugs and open die spaces, the spaces arranged to provide molten resin that fills the spaces 352 between the bands of the nonwoven loop material and produce limited overlap of the resin and the bands of nonwoven (FIG. 17B), for forming joints 28 by in situ lamination techniques. The edge margins of the bands of nonwoven material bond intimately with the edge margins of the molten resin with which bands of hook fasteners 354 are integrally formed. The bond is formed by encapsulating fibers of the surface structure of the loop material with the molten resin of the hook material. Thereby a composite structure of alternating bands of loop component and hook component are formed by in situ lamination.

In another case, a widthwise continuous single web of loop material, such as shown in FIG. 16 is fed to the machine, while a slot-form die with alternating plugs and open die spaces, FIG. 17A, is employed to lay down separated, parallel bands of hooks directly upon the web, e.g. to form the in situ laminated product of FIGS. 12C and 12D as further discussed below.

In one example, a web includes (FIG. 18), starting from the left, a 3 inch wide strip of unsupported nonwoven loop, an inch and a half wide strip of hook material, in situ bonded at its margin to surface structure of the nonwoven, a 6 inch wide strip of unsupported nonwoven loop, an inch and a half wide strip of hook material, in situ bonded at the margins to the surface structure of the nonwoven material and a 3 inch wide strip of unsupported nonwoven loop. The alternating bands of nonwoven and hook material thus overlap partially, being in situ bonded at joints 28. The overlap areas are, for instance, ⅜ inch wide. The construction of the nonwoven strip can advantageously be uniformly the same in the in situ bonding regions behind the hook material and in the resin-free, unsupported regions. After formation, the web may pass through a slitter where it is longitudinally slit at the midpoints A and C of the hook segments, and at the midpoint B of the 6 inch loop segment. This results in four continuous length composite flexible webs, each comprising a narrow band of hook material joined to a relatively wide band of nonwoven loop material (FIG. 19).

Alternatively, e.g., to form the products of FIGS. 12C and 12D, the loop material, which may be one of the stretchy loop materials or flexible materials described herein or in the references, extends continuously, across the full width (as suggested by the dashed lines in FIG. 18) and the hook bands are laminated in situ to the loop material across their entire back surfaces, following which slitting is done as before.

In the next step each of the four flexible webs passes through a coating line where a pressure-sensitive adhesive is applied to the back of the hook strip material (or the loop material in the example of FIG. 12C), this followed by a step in which a release liner 32 is placed on the adhesive layer, see FIG. 19.

At that point each of the four continuous webs is perforated-cut (kiss-cut) along lines 400 through the loop and hook side but not through the release liner 32, as shown in FIGS. 20, 21, and 23, to form a series of elongated bag ties. The direction of the kiss-cuts 400 is perpendicular to the longitudinal axis 402 of the composite web, i.e. perpendicular to the machine direction. A cross section of the web along the indicated direction 22—22 in FIG. 21 is shown in FIG. 22.

Various types of resins may be used to form the hook and the nonwoven material. In certain preferred cases, as mentioned, the nonwoven material is made from polyester fibers and the hook material from polyethylene. The hook and loop material preferably differ in their heat properties. For example, the polyethylene melts sooner than the polyester and thereby allows, during in situ lamination, the thermal fusing of the hook resin around the polyester fiber of the loop material, to form a strong mechanical bond with dimensional stability.

The adhesive for layer 30 is preferably a pressure sensitive type adhesive. In some instances, layer 30 may be a synthetic resin suitable for thermal fusion onto a substrate.

Figure 24:
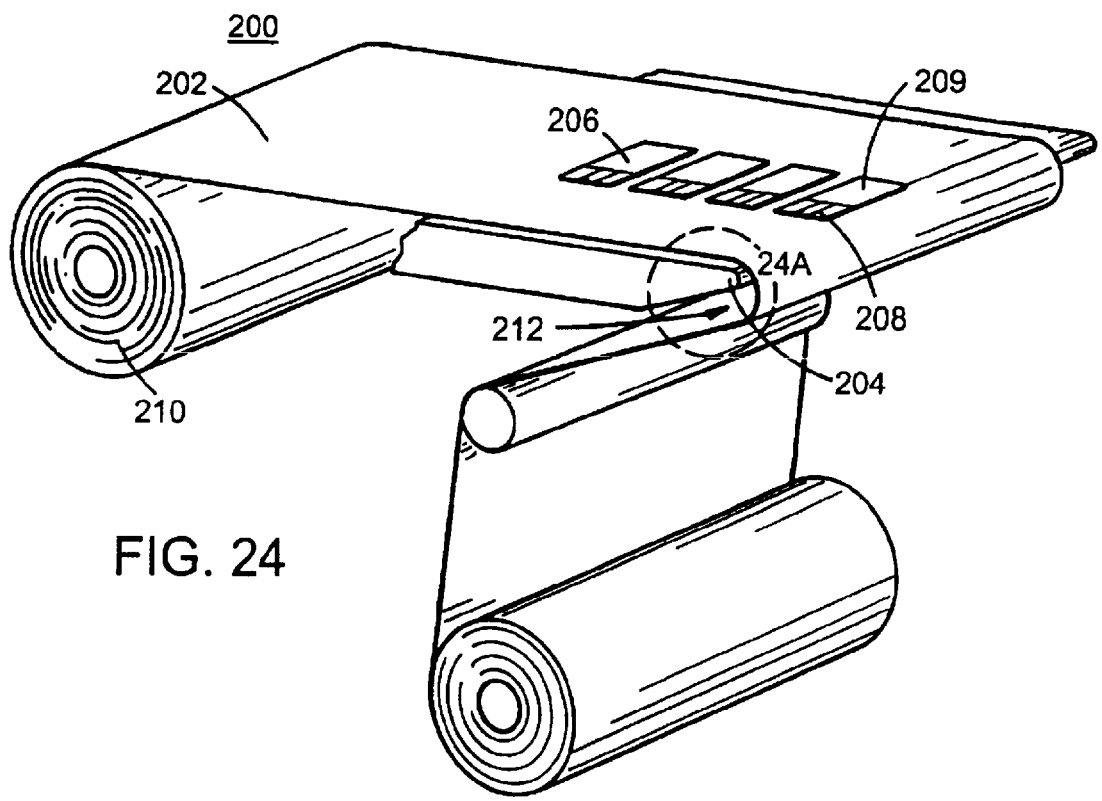
FIGS. 24 and 24A depict delivery of discrete fastener tabs.
Figure 24A:
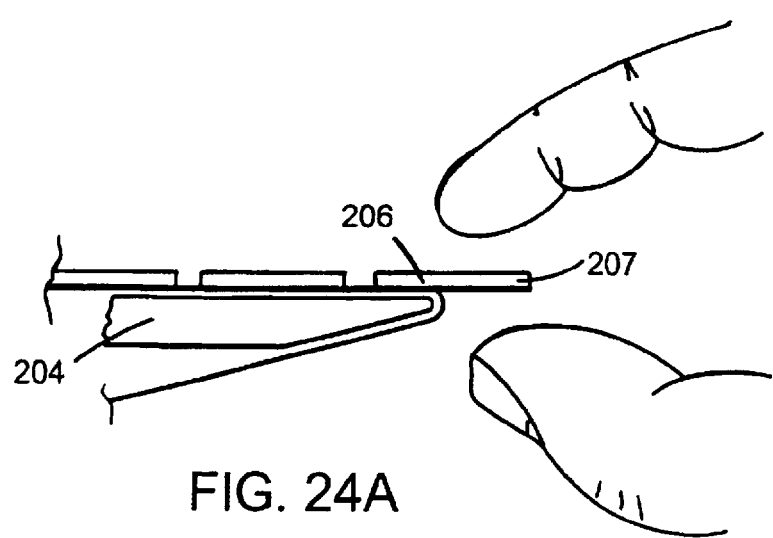

Referring now to FIGS. 24 and 24A, wrap ties carried by a common release liner 202 may be wound into a roll 210. The wrap ties 206 have one end 208 attached to the release liner with the pressure sensitive adhesive and a free end 209. The roll 210 may be fed to a standard labeler 200, shown diagrammatically in FIG. 24. The release liner is arranged to pass under a sharp angle 212 around a peel plate 204, where it reverses direction. The release liner is flexible and can change direction easily. However, the wrap tie has a certain amount of stiffness that causes the edge of the wrap tie 207 not to follow the release liner 202 around the peel plate 204, and to protrude at the point where the release liner reverses its direction (FIG. 24A). In this way the peel plate automatically separates the wrap tie from the release liner.

Other features and advantages of this invention may include one or more of the following. The web in FIG. 18 maybe first coated in appropriate locations with the pressure sensitive adhesive and then passed through the slitter where it is longitudinally slit to form the hook and loop segments. The very low thickness of both the nonwoven loop material and the hook material, along with its low cost and good closure performance, make the wrap tie a particularly useful component of many products. The wrap ties may be employed, for instance to close a plastic bag as described above (FIG. 12A), to secure pipes or other building materials, to bundle cables and secure bundled cables, to serve as diaper tabs, and for other straps and wrappings about the body, to secure medical devices, etc.

While so far we have chosen to illustrate the invention with respect to stretchy tabs useful for infant and adult diapers; surgical gowns and other garments and wraps and with respect to stretchy ties and straps useful in packaging, bundling and securing building material, cables and other devices, it will be understood that the techniques disclosed have general applicability and may be used in a wide range of applications.

For these purposes, various stretchy loop materials and flexible materials, can be employed.

Figure 25:
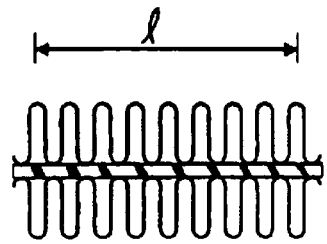
FIG. 25 is a diagrammatic illustration of a double-sided loop material formed on an elastomeric base while FIG. 25A illustrate the loop material of FIG. 25 in an elastically stretched condition resulting from application of tension.
Figure 25A:
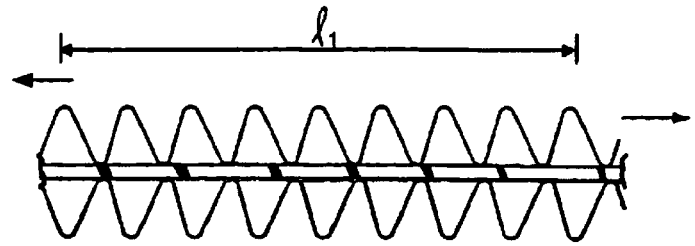
Figure 26:
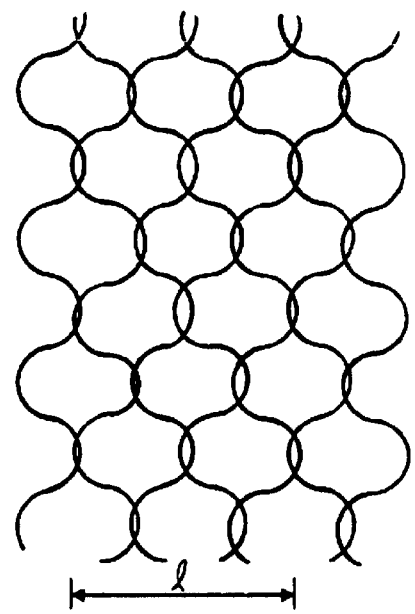
Figure 26A:
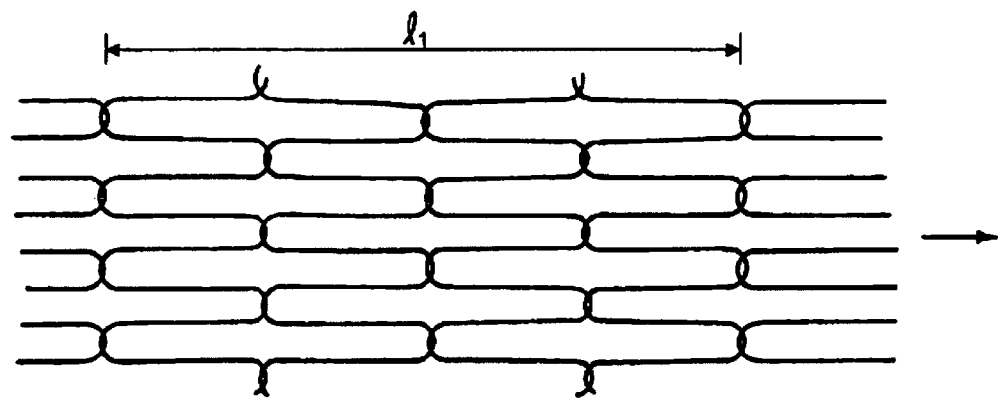
FIG. 26A illustrates the loop material of FIG. 26 in a lengthwise tensioned, widthwise relaxed state in which it can be stabilized, e.g. by a binder, to impart widthwise stretchiness.

FIG. 25 generally illustrates in relaxed condition and FIG. 25a illustrates in stretched condition during use, a composite, elastically stretchable loop material. It has a base comprised of elastically stretchable material and hook-engageable loops, in this case formed on both sides. This represents, diagrammatically, a wide variety of known materials useful for hook and loop fastening. For instance, the material may be a laminate of an elastomeric central layer between two outer layers of nonwoven material configured to define hookengageable loops. By suitably laying the fibers of the nonwoven material to lie predominantly in the machine direction, or by pre-stretching the material in the machine direction while relaxed in the cross-machine direction and allowing the material to neck and stabilizing it in such condition, the composite may be substantially non-extensible in the machine direction while elastically stretchy in the cross machine direction for the advantages described earlier concerning machine direction tension. FIG. 26 generally illustrates in relaxed condition and FIG. 26a illustrates in stretched and stabilized condition, a knit fabric, also having single direction stretchiness properties. The fabric has hook-engageable loops not shown. In this case, as with the needled nonwoven product described earlier, an elastomeric fluid binder is applied and cured to stabilize the fabric in the distended condition of FIG. 26a, such that the fabric does not have significant elastic stretchiness in the direction of the arrow in the figure, while having elastic stretchability in the orthogonal direction.

Stretchy nonwoven materials may be made in other known ways which provide hook-engageable loops and are elastically stretchable. Useful materials are webs which themselves or their components are originally extensible in both machine and cross-machine directions, but which during manufacture are treated or have components added that eliminate extensibility in the machine direction.

A general class of such useful stretchy hook-engageable webs for the purposes being described, comprises webs which have an elastic or an elastomeric layer such as a film or thin layer of thermoplastic elastomer or synthetic or natural rubber, which by itself would be elastic in both orthogonal directions during manufacture. Such layer is elastically pre-stretched widthwise only and combined with longitudinally dimensionally stable constituents. These, thereafter, prevent extension in the machine (lengthwise) direction. Following such assembly, the web is relaxed widthwise and allowed to elastically contract. It is capable thereafter of extending elastically in the widthwise direction. One example is a very thin elastic film, e.g. of less than 0.001 inch thick or, in sturdier fabrics, less than a few thousandths inch thickness which, while being stretched widthwise, has combined with it on one or preferably on both sides, non-extensible thin nonwoven fabrics which have the effect of preventing lengthwise stretch, but which, upon relaxation of the widthwise stress and contraction of the elastic layer, gather to form longitudinally-extending loop-covered ridges or ribs, which define hook-engageable loops that can thereafter be distended under widthwise stress that stretches the elastomeric foundation layer.

Another example of useful webs is the general class of needled, uni-directionally pre-stretched and stabilized, hook-engageable, nonwoven, stretchy or flexible webs that have been described in detail above, preferred embodiments of which are formed from highly crimped polyester staple fibers which have been needled to form loops on the face of the fabric and then stretched at least 20% (only in the machine direction for elastically stretchy fabric while the needled fabric is relaxed and allowed to neck in, in the cross-machine direction), and stabilized with a binder (preferably for elastically stretchy fabric, an elastomeric binder such as nitrile rubber binders, the Hystretch® binder referred to above or other binders available from B. F. Goodrich Company).

A useful guide to the degree of elastic extensibility or stretchability suitable for elastically stretchy products according to the invention is given by others in the field who have sought to address some of the same needs that are successfully addressed in the present application. Thus, in respect of products such as sanitary napkins, diapers and extensible wraps used for athletic purposes, i.e. to support joints and muscles, U.S. Pat. No. 6,080,347 considers a substrate to be suitably elastically extensible if it exhibits a relaxation-extension area ratio greater than or equal to about 0.6, and preferably greater than or equal to about 0.75 when tested as described in that patent. See also U.S. Pat. Nos. 5,318,555 and 6,106,922 and the elastomeric nonwoven laminates disclosed in U.S. Pat. Nos. 4,789,699; 4,863,779; 4,939,016; 5,536,563 and 5,681,645. The full disclosures of all references cited here are incorporated by reference. These standards can apply to the present invention as well.

A superior product, produced according to the present invention, employing an elastically extensible, hook-engageable web similar to as that described in U.S. Pat. No. 6,080,347, but the product having very superior attributes over the products described in that patent, will be described with references to FIGS. 27 et. seq. The particular stretchy loop web to be employed in the following example is elastically extensible in the cross-machine direction, but substantially inextensible in the machine direction.

Figure 27:
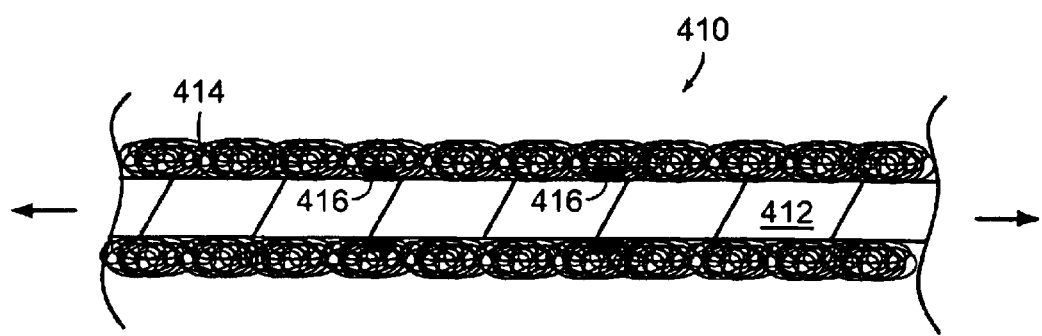
FIG. 27 is a transverse cross section (cross-machine direction) of a composite loop material during its manufacture.

FIG. 27 illustrates a transverse (cross-machine direction) cross-section of a composite loop material web 410 during its manufacture. Elastic central layer 412, is extended uni-directionally, in the cross-machine direction, under tension (as indicated by arrows in FIG. 27) and thin upper and lower dimensionally stable nonwoven layers 414 are applied to opposite major surfaces, formed as by melt blown or spun bonded nonwoven forming techniques. The nonwoven layers are bonded to the elastic foundation layer by a series of close-together relatively narrow machine-direction thermo-bonding lines 416 extending lengthwise so that when the widthwise stretching is relaxed, the relatively free non-woven segments between the weld lines pucker or form corrugations while the elastic core layer contracts width-wise. The completed material (FIG. 27A) has pillowed regions 418 of hook-engageable fibers of the nonwoven layers formed by bulging of the nonwoven material between adjacent thermobonding lines, presenting hook-engageable fiber loops.

Figure 28:
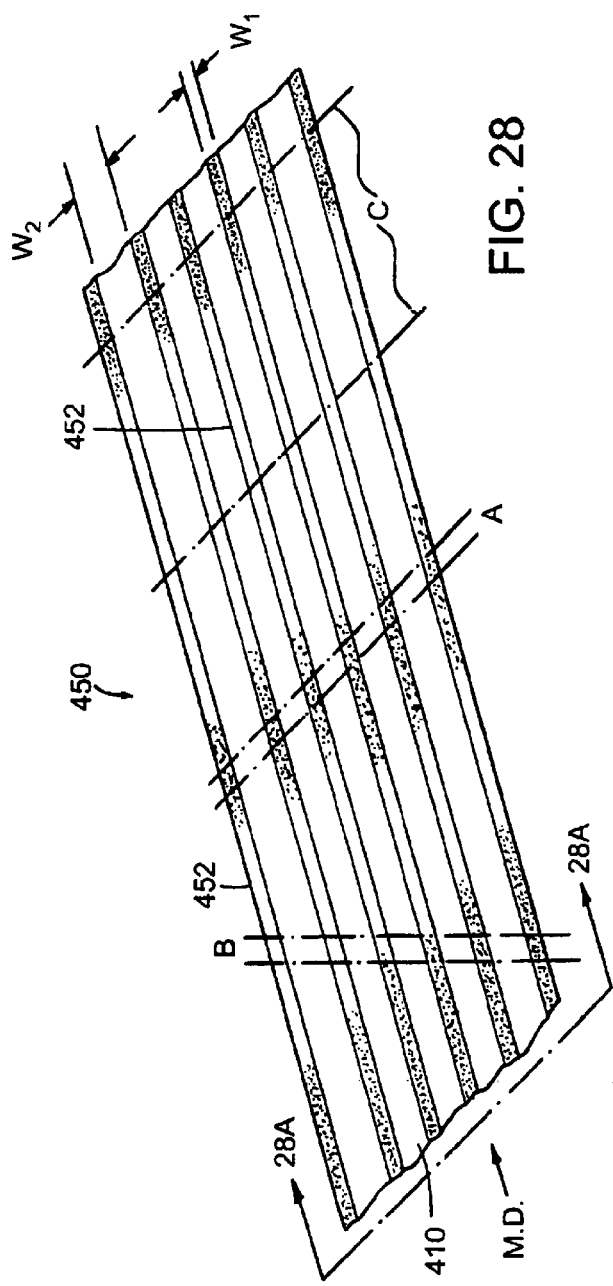
FIG. 28 is a diagrammatic perspective view of a "zebra-like" composite stretchy hook and loop material.
Figure 28A:
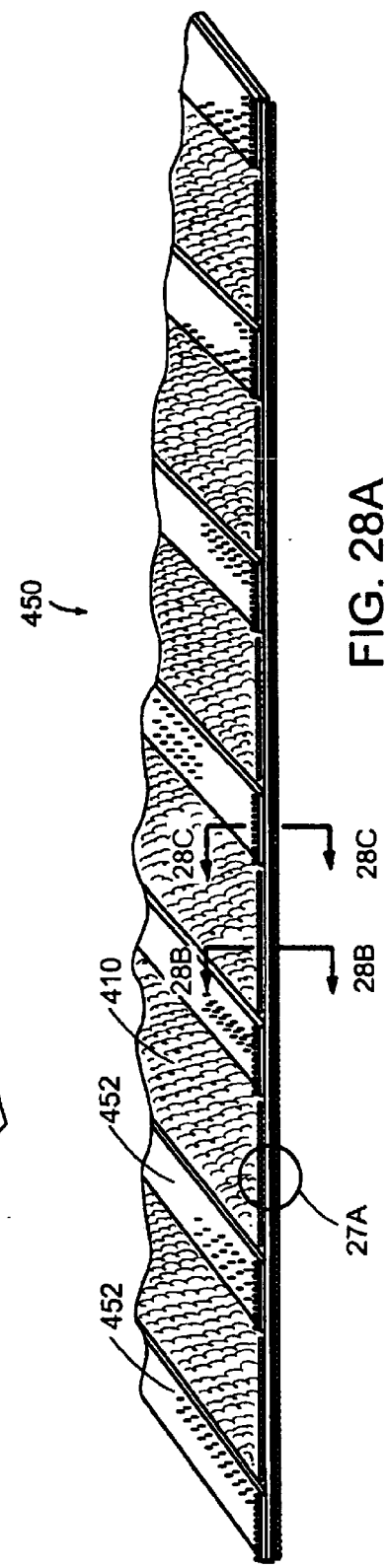
Figure 28B:
FIGS. 28B and 28C are longitudinal (machine direction) cross-sectional views taken respectively on lines 28B—28B and 28C—28C of FIG. 28A, on an even more enlarged scale.
Figure 28F:
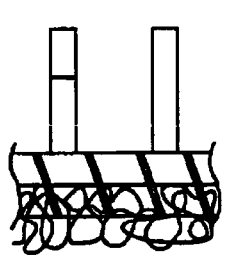
FIG. 28F is a cross-sectional view taken on line 28F—28F of FIG. 28D.
Figure 28D:
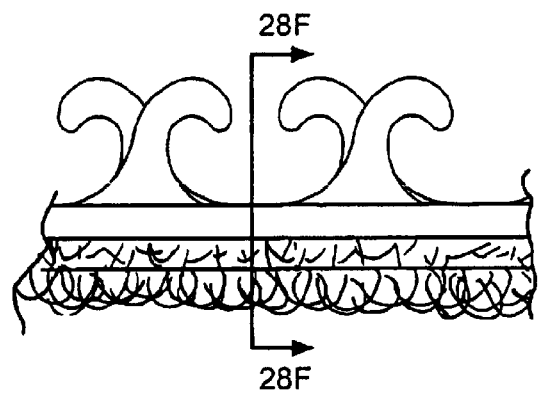
FIGS. 28D and 28E are cross-sectional views on still a more enlarged scale of the circled portions of FIGS. 28B and 28C, respectively.
Figure 28C:
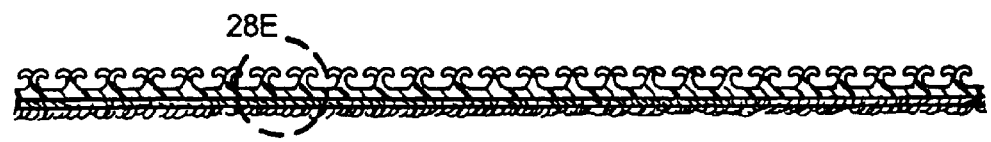
Figure 28E:
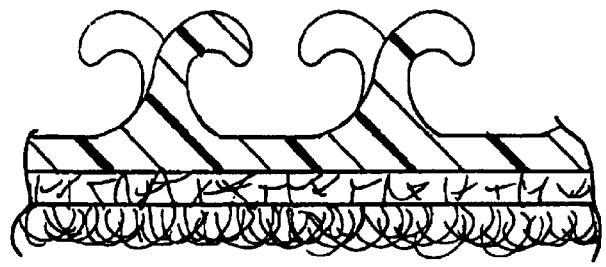

Such a loop material can be used to form the product 450 illustrated in FIGS. 28–28E, i.e., a "zebra-like" composite stretchy hook and loop material formed with separated bands 452 of loop-engageable hook on the widthwise stretchy loop material 410. Between the bands of hooks, the material 410 appears as bands of hook-engageable loop material. (A similarly appearing product of non-stretchy material can advantageously be formed by employing a non-stretchy loop material). In either case, by choice of a highly flexible loop materials, the regions of unconstrained loop material (free of the resin from which the hooks are formed) that lie between the bands of loop-engageable hooks provide flexural regions that contribute considerably to the overall flexibility and conformability of the composite product.

Figure 29:
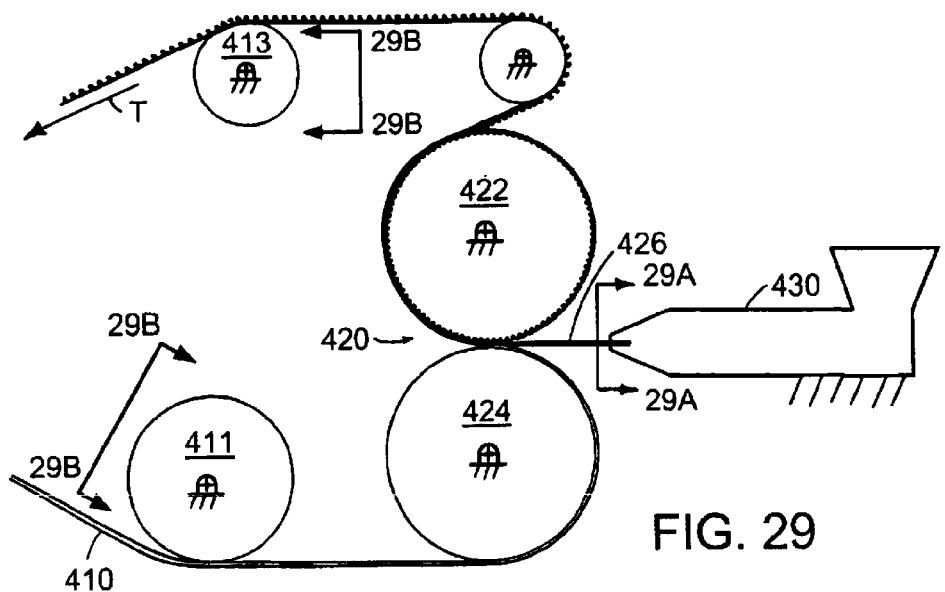
FIG. 29 is a diagrammatic side view of a machine for forming the product of FIG. 28.
Figure 29A:
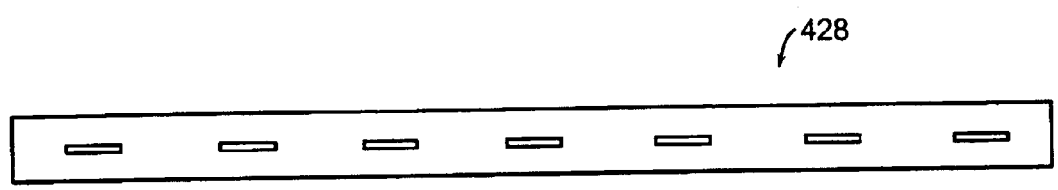
FIGS. 29A and 29B are transverse views taken on lines 29A—29A and 29B—29B of FIG. 29.
Figure 29B:
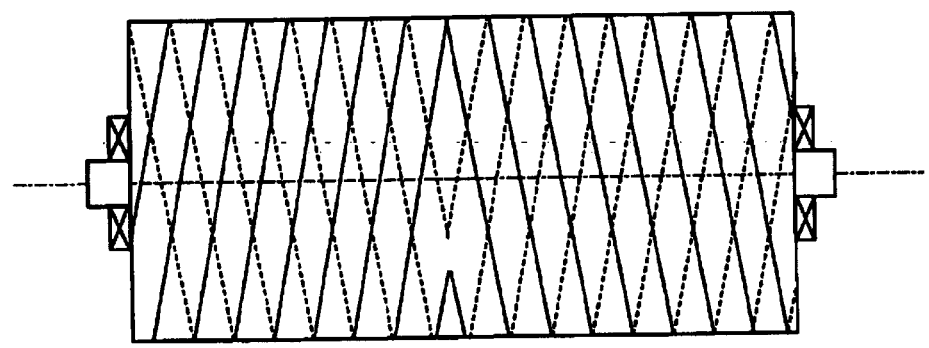

Referring now to FIGS. 29–29B, a process and apparatus similar to those described above with reference to FIGS. 9–10 is illustrated for forming the product of FIG. 28. The loop material 410 is fed into a nip 420. If it is elastic in one direction, it has its elastic dimension perpendicular to machine-direction tension (indicated by arrow T). Nip 420 is formed by a mold roll 422 and pressure roll 424 similar to those previously described. Simultaneously with feeding in the loop material 410, thermoplastic resin 426 is fed into nip 420 by extruder 430 through the spaced narrow width, slot die orifices of deckled die 428 (FIG. 29A) so that the resin is provided as narrow, separated bands conforming to a common plane. As these bands of molten resin pass into nip 420 they are, on one side, in situ laminated fully across their back to surface structure of loop material 410 while on the other side, the resin is molded into the form of loop-engaging fastener elements (or molded stems which are later treated to form loop-engageable features, as previously described). This produces spaced apart, parallel hook bands 452 (FIGS. 28–28E), or bands of stems that are later treated to form hooks on one side of the carrier sheet, while the opposite side of the loop material can remain pristine, free of hook resin, and, if defining hook-engageable loops on that side, the loops remain unimpaired and effective. Spreader rolls 411, 413 having parallel ribs and grooves slightly angled away from their center (FIG. 29B) guide the material and maintain it wrinkle free, widthwise during processing.

CFM-29 hook forms may be employed. The hook bands may for instance, have width of ⅛ inch to ¼ inch, and provide, in each band, many rows of hooks, e.g., 10 to 50 closely spaced rows of tiny hooks.

Figure 30C:
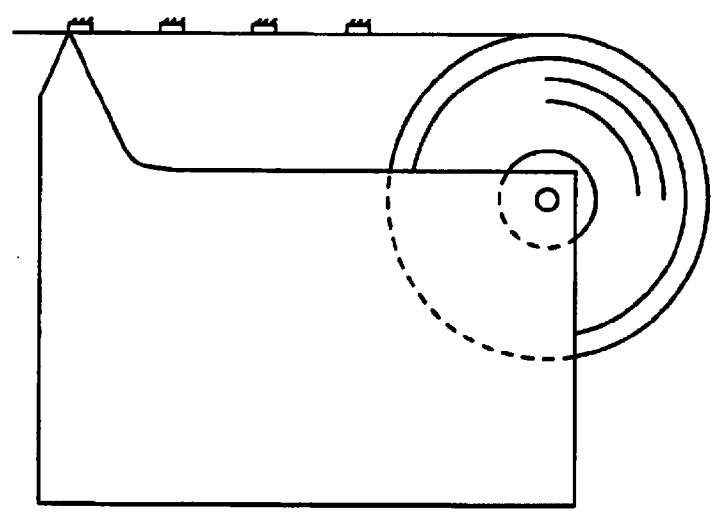
FIG. 30C illustrates a dispenser for a roll of strapping or wrapping material formed according to FIG. 28 in widths such as illustrated in FIG. 30 or FIG. 33.
Figure 30:
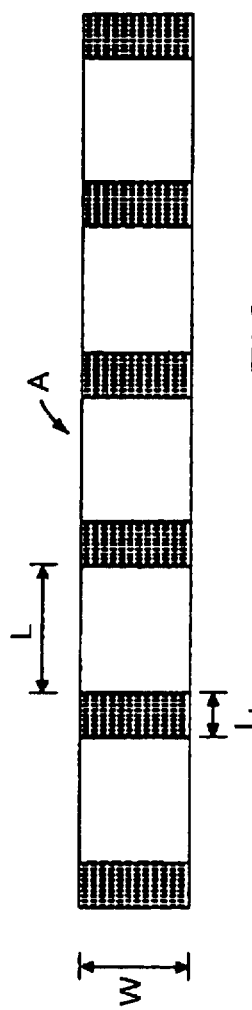
FIG. 30 is a plan view of an article produced from the material of FIG. 28, by cutting on lines A of FIG. 28.
Figure 30A:
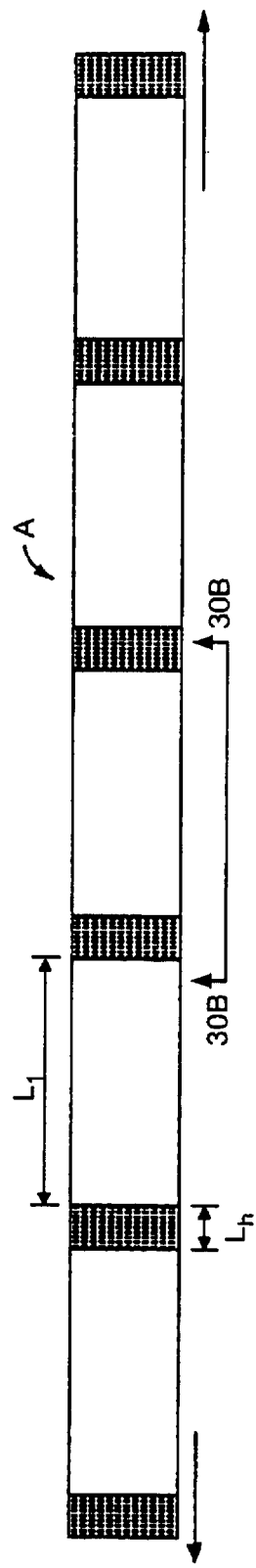
FIGS. 30A and 30B are plan and cross-machine direction elevation views of the material of FIG. 30 under tension during use.
Figure 30B:

As illustrated in FIG. 30 a self-engaging article formed by cutting a stretchy composite material 450 along lines A (FIG. 28), in relaxed state, has width (w) and in its stretchable direction has a multiplicity of alternating loop and hook bands, the loop bands of dimension (l) at least equal to the dimension ($l_h$) of the hook bands and preferably between 2 to 5 times larger, for self-engageable products that engage upon themselves regardless of location. Under tension during use, the material of FIG. 30 is stretched as illustrated in FIGS. 30A and 30B so that the loop bands have increased dimension ($l_1$). The material of FIG. 30, arranged in a roll of strapping, can be dispensed from a roll as illustrated in FIG. 30C.

Figure 32A:
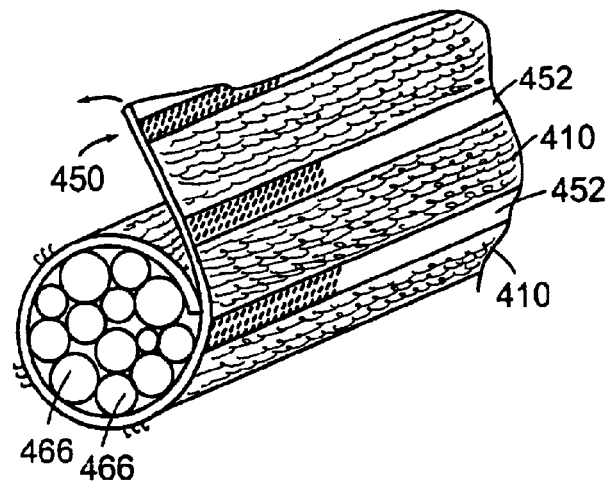
FIG. 32A illustrates the application of a wider width wrapping such as that of FIG. 33.
Figure 32:
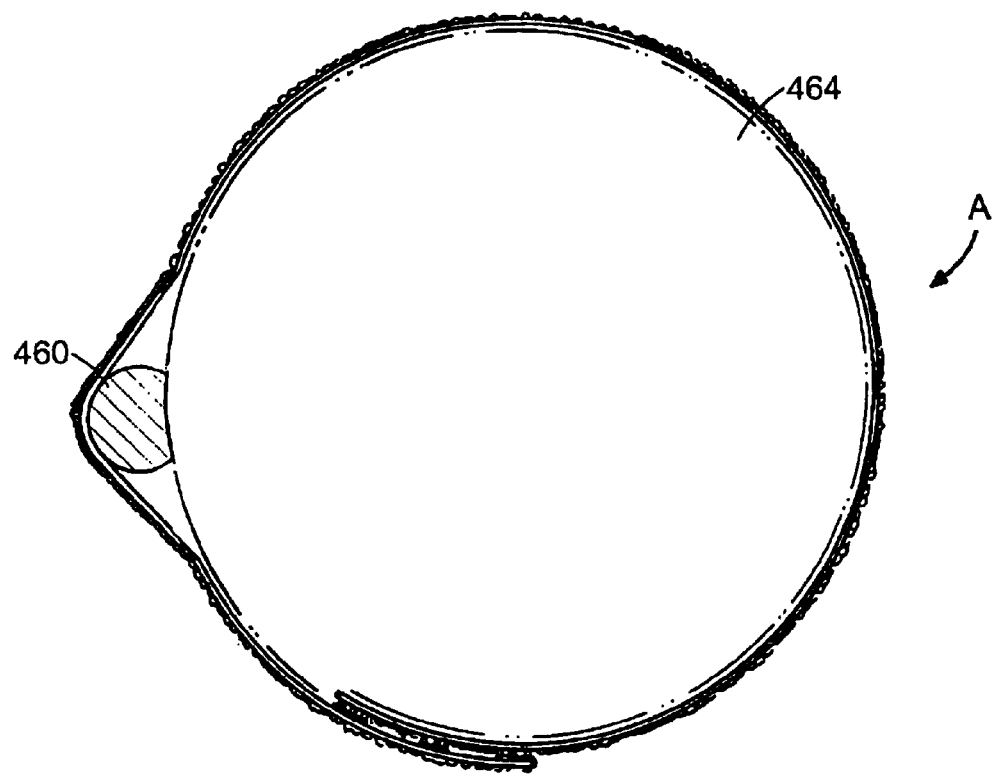

There are many uses for such self-engaging straps and wrappings. For example, FIG. 31 is an illustration of use of the article of FIG. 30 as a strap to yieldably support a medical IV drip catheter 460 from a support rod 462. As diagrammatically illustrated in FIG. 31A the inter-engagement of the bands of hooks 452 with the bands of loop material on the same side of the material accomplishes securement. FIG. 32 illustrates adaptation of the article of FIG. 30 as a cinching strap, in this case, for instance securing the IV catheter 460 to a solid support 464, with bands of hooks which overlap the back of the material engaging hookengageable loops on the back surface. FIG. 32A similarly illustrates the cinching strap 450 being wrapped (as indicated by the arrow) a number of times about a bundle of elongated members 466, e.g. as a bundle tie for a number of medical tubes or electric cables or as a tie for a bundle of asparagus or flower stems.

Figure 33:
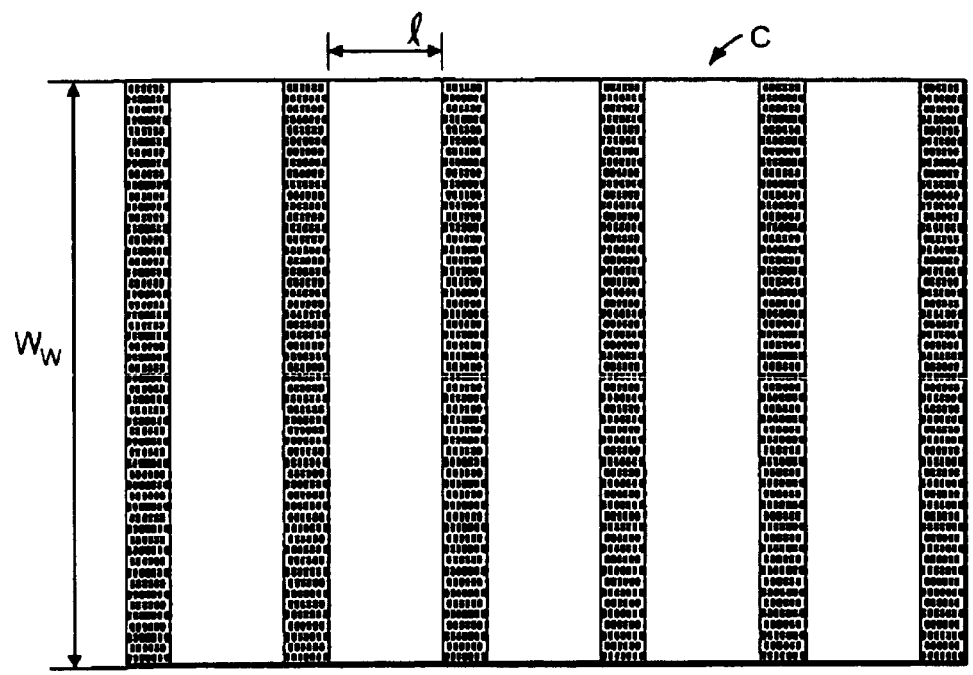
Figure 33A:
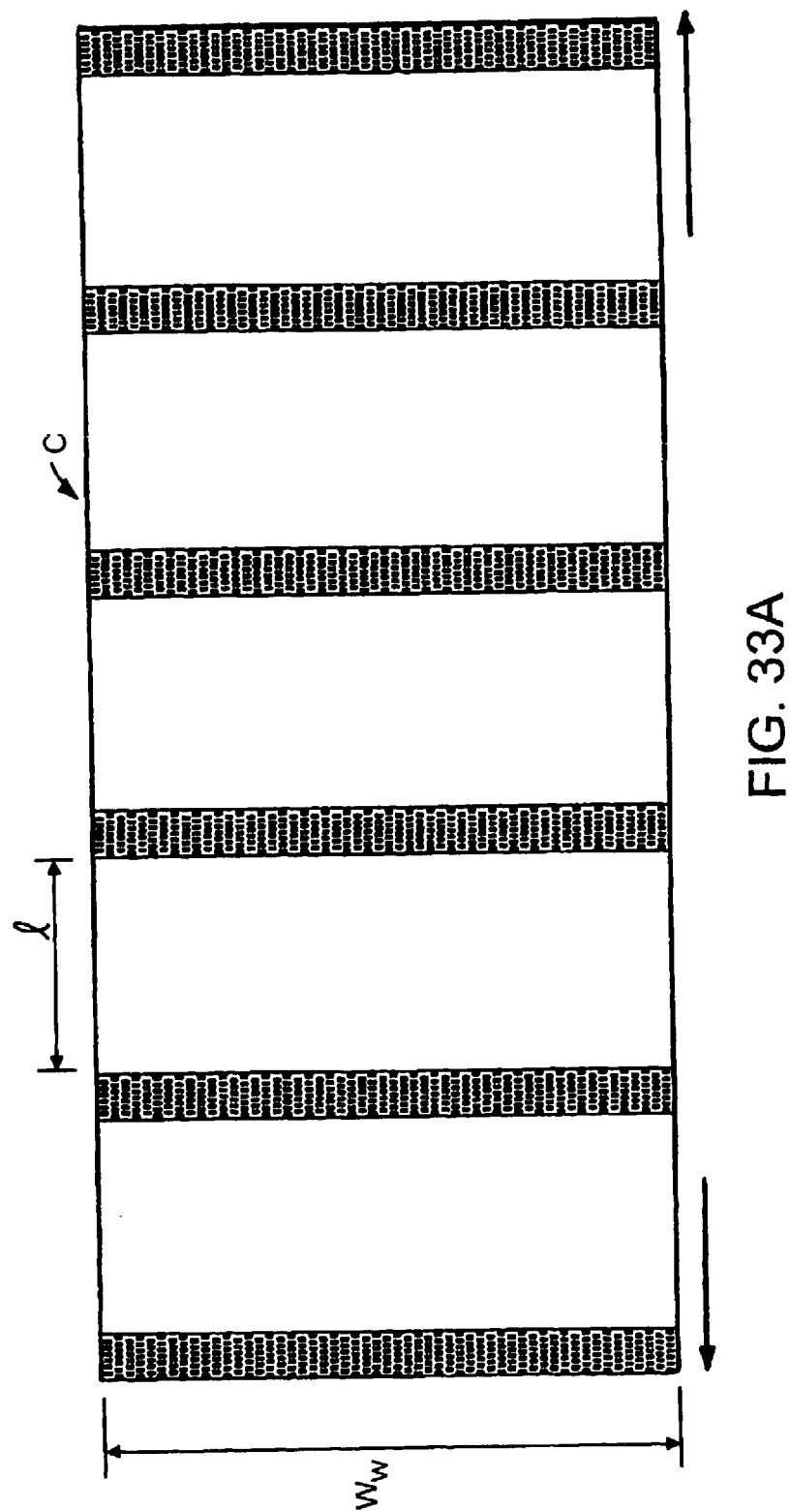
FIG. 33A illustrates the article of FIG. 33 in stretched condition.
Figure 33B:
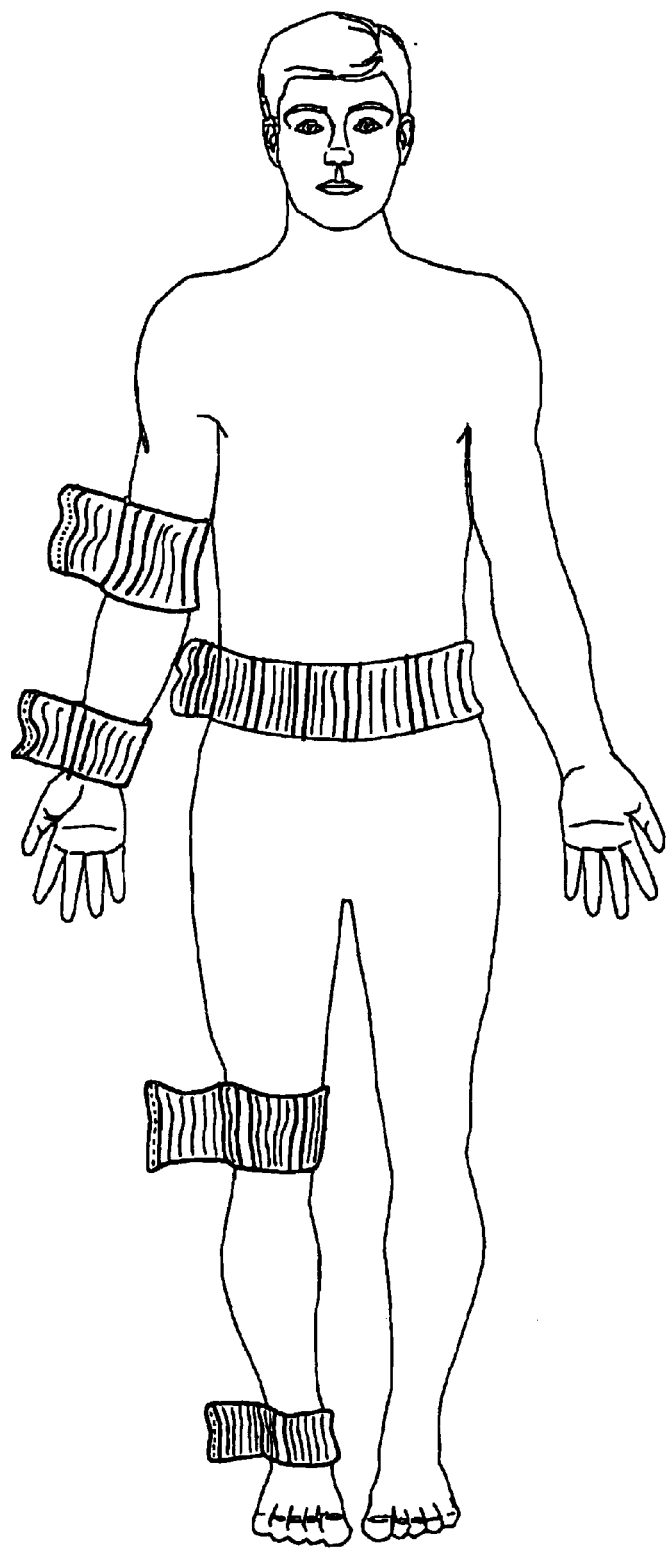
FIG. 33B illustrates a use of the article of FIG. 33 as a wrapping for human joints, limbs and torso.
Figure 35:
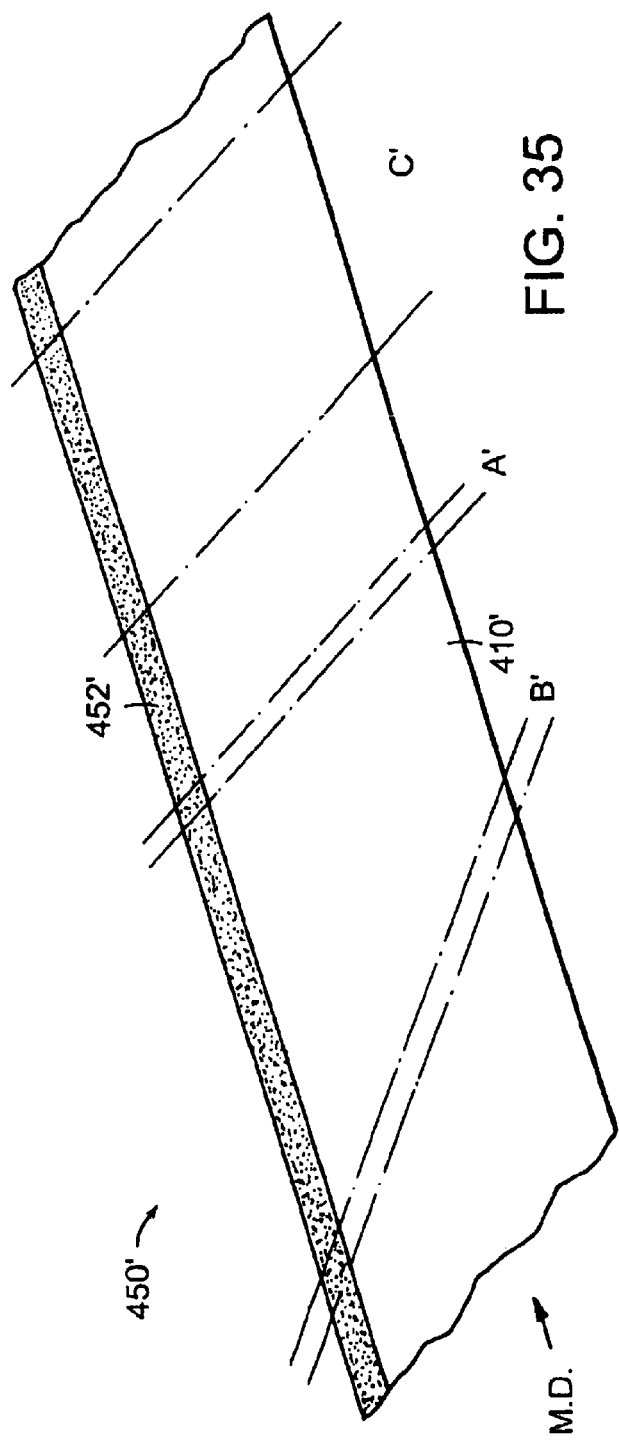
Figure 36:
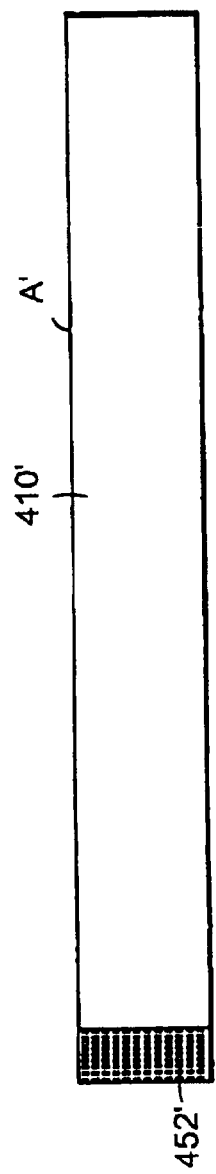
FIGS. 36–38 are plan views of further articles according to the invention, formed e.g. from the material of FIG. 35.
Figure 37:
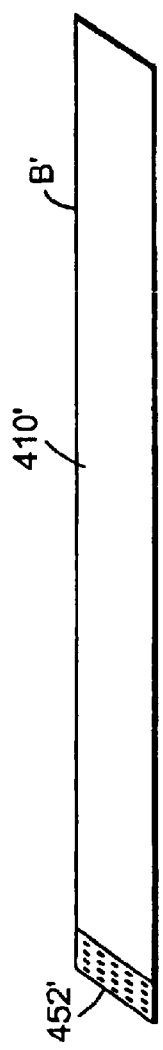
Figure 38:
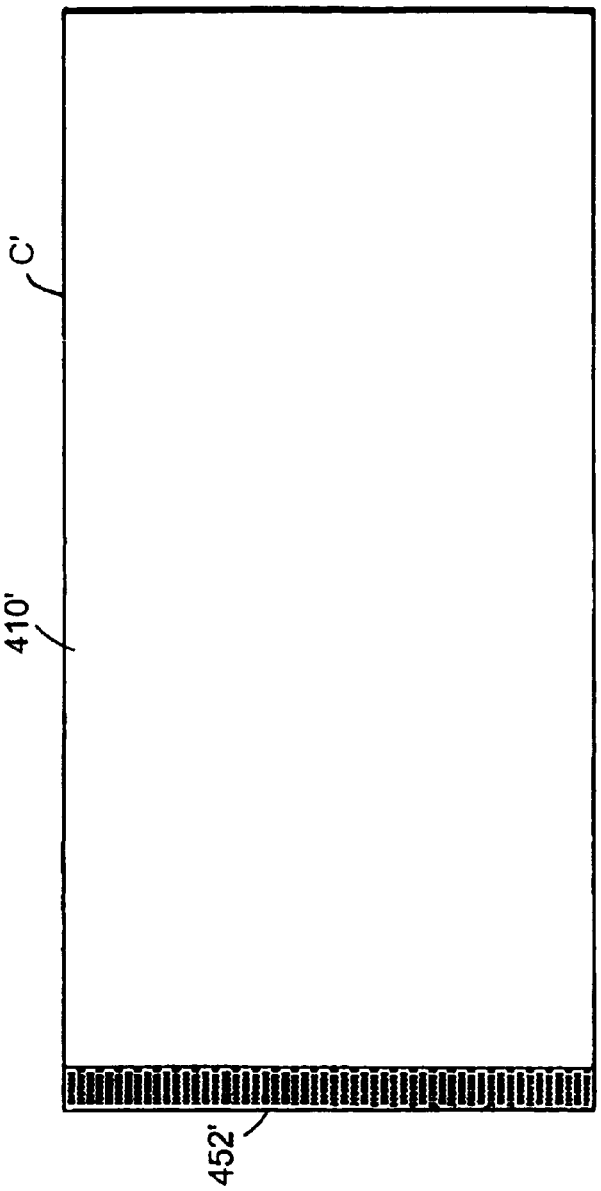

As illustrated in FIG. 33, a wrapping of extended width ($w_w$) is cut from material 450 in the direction of cutting lines C (FIG. 28). FIGS. 33 and 33A illustrate the wrapping in relaxed and stretched conditions, respectively. Such a wrapping can be used as a medical therapeutic wrapping or athletic protection and strengthening wrapping applied to a part of the body such as in locations suggested in FIG. 33B. The free-ends of the wrapping shown in FIG. 33B are intended to suggest that the material can be wrapped around itself a number of times, engaging itself continuously. When wrapping is completed, the free end likewise engages the material of the previous turn, to lie neatly flat. The thickness of the resin of the base layer of the hook bands can be selected and the base layer of the hook bands can be made continuous in their extent and of selected width to provide a desired degree of stiffening support or even an immobilizing splint effect, especially when wrapped in multiple turns about a joint of the body or a cracked or broken bone or other injured region of the body that requires stabilization. The material is therefore useful in EMT and emergency medicine as well as in conventional clinic and athletic use.

This wide material can also be made available in a roll and dispensed at chosen lengths from a dispenser as depicted in side view in FIG. 30C.

For further discussion of use of the material in medical products and for novel product configurations, the reader is referred to co-pending U.S. patent application No. 60/242,823, to Joy, et al., entitled "Wound Covering," filed simultaneously herewith, the entire contents of which are hereby incorporated by reference.

Figure 34:
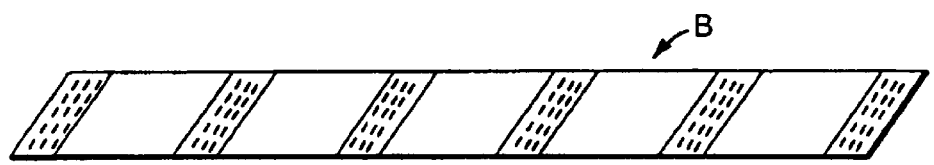
FIG. 34 illustrates an article cut at a bias angle along lines B of FIG. 28.

FIG. 34 illustrates an article cut from an elastically stretchy composite at acute angle along lines B in FIG. 28 to impart a degree of elastic extensibility both widthwise and lengthwise of the strap.

Referring now to FIGS. 35–38, another product 450' similar to that of FIG. 28 but arranged to have an extended single band of loop material 410' and a short single band of hook material 452', is useful, e.g., as a stretchy bag tie as described earlier, which otherwise is formed according to the above techniques. Lines A', B' and C' of FIG. 35 indicate examples of directions and the manner in which the material may be cut to form the articles of FIGS. 36–38, respectively. When wrapped about a limb, the only hook and loop fastening occurs where the single band of hook 452' lands upon the loop material. This produces a softer wrapping, useful for instance on regions of the body intended to remain active and capable of flexing.

Figure 40:
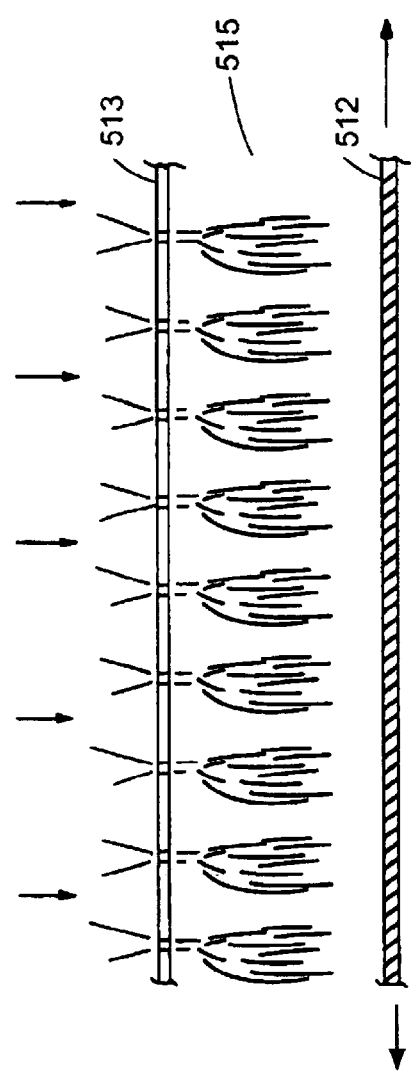
FIG. 40 is a diagrammatic cross-section taken along lines 40—40 of FIG. 39.
Figure 39:
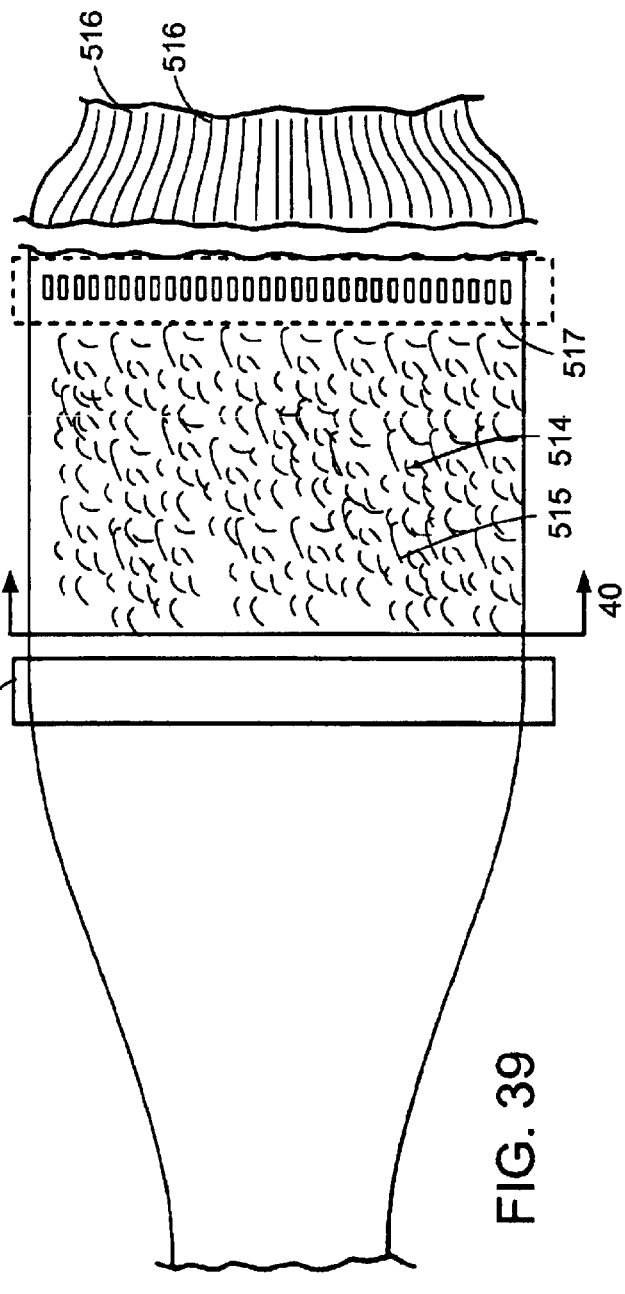
FIG. 39 diagrammatically illustrates, in plan view, a method and apparatus for forming a stretchy loop material similar to that depicted in FIG. 27A.

FIGS. 39 and 40 illustrate a method and apparatus for forming a stretchy loop product having characteristics similar to that described above with reference to FIGS. 27 and 27A. In this case, the uni-directionally stretchy loop material 510 is formed by application of widthwise tension to an elastic carrier 512 while a non-extensible, nonwoven fabric 514 is formed on its surface comprising fibers 515. Fibers 515 are laid directly on the layer 512 as with nonwoven textile manufacturing techniques, e.g., by airlaying or melt blowing techniques, the fibers adhered to each other either by the inherent adhesiveness of the laid fibers, or by a minor percentage of adhesive fibers mixed with the main fibers, or otherwise by adhesive additives and heating. In the illustrated embodiment, melt blower 513 applies fibers 515 to elastic layer 512 while the elastic layer is spread in a widthwise direction (e.g., by a tenter frame not shown) to form nonwoven layer 514. the fibers may have a principal orientation in the lengthwise direction such that the layer they form is not readily extensible in that direction. In one technique (not shown), thin upper and lower dimensionally stable nonwoven fiber layers are combined on respective sides with stretched elastomeric plastic film (see FIG. 27). In another embodiment, the nonwoven layers are separately formed, then introduced respectively to opposite sides of the width of the stretched central elastic layer.

Figure 27A:
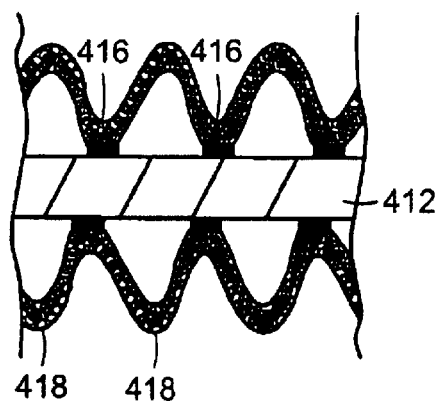
FIG. 27A is a similar view of the composite loop material of FIG. 27 after manufacturing has been completed.

In either case, following application of nonwoven web(s) 514, a series of close-together thermobonding lines 516 extending in the machine direction are formed at bonding station 517 to bond the nonwoven web(s) 514 to the faces of elastic film 512. After solidification of the bonds, the widthwise tension is released. As the elastic film contracts, the nonwoven material on opposite sides gathers into ridges or corrugations between the bonding lines, as illustrated in FIG. 27a referred to above. This forms a uniform set of closely adjacent parallel hook-engageable ribs 516 extending in the machine direction, the material being elastically stretchy widthwise and relatively inextensible in the machine direction.

In another case, a hook-engageable textile such as a knit material, is formed, which incorporates a suitable percentage of elastic yarns, such as SPANDEX® yarns (principally comprised of urethane), which are incorporated under light tension during formation of the web. Other elastomeric yarns may be of GLOSPUN® or CLEARSPUN® available from Globe Co., or DORLASTAN®, available from Bayer Inc., or other yarns formed of filaments of long chain elastic material such as segmented polyurethane. Where less stretch is required, texturized yarns comprised of crimped fibers or crimped yarns are employed, such as those produced by stuffer-crimpers, gear crimpers, or other known crimping techniques or by microcroping. Crimped or texturized polyester filaments and yarns are particularly preferred for strength in achieving hook and loop engagement.

Figures 41, 42:
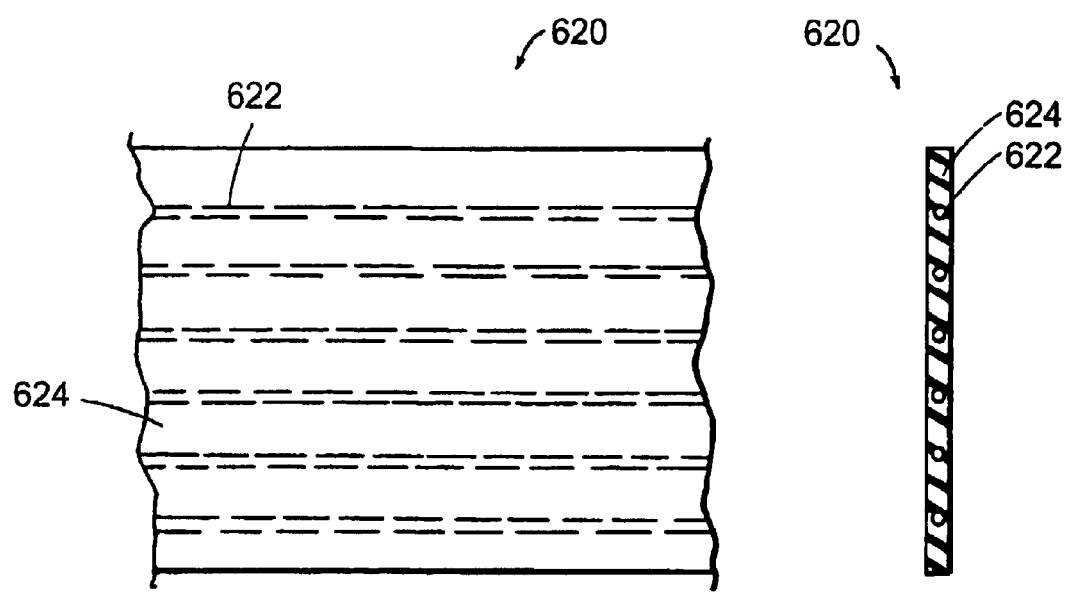
FIGS. 41 and 42 diagrammatically illustrate, in transverse cross-section and plan views, respectively, another stretchy material useful according to the invention.

Upon initially being formed, the textile web may be stretchy in the machine as well as cross machine directions. Subsequently, or during manufacture of the web, stretch-resistant elements, such as polyester monofilaments extending lengthwise may be added to the web, such that the resulting composite is not substantially elastically extensible in the machine direction, but is elastically extensible in the cross-machine direction, for the advantages mentioned above. For example, as illustrated in FIGS. 41 and 42, relatively inextensible monofilaments 622 are added to otherwise elastic web 624, so that the resulting composite web 620 is relatively inextensible in the direction of the aligned monofilaments, but remains stretchable in an orthogonal direction, e.g., the cross-machine direction.

In another case, the formed web, formed e.g., of SPANDEX® yarns, is pre-stretched in the machine direction to its limit while relaxed widthwise, and then heat set, thus removing extensibility in the machine direction.

In the example, as described above, and now illustrated in FIGS. 43 and 44, nonwoven batt 630 (formed e.g., as described in the above-incorporated U.S. Pat. No. 6,329,016), relatively stretchable in all directions, is passed through needling stations N1 and N2, where it is needled to form a nonwoven mat having hook-engageable loops. Subsequently, the needled web passes through tension control nip rolls, S1 prior to application of a binder (as discussed above) at coating station C and then through tension applying nip S2. The speed of the rolls at station S2 is greater than those at S1 so that the web is stretched in the machine direction, while it is maintained in a relaxed state cross-wise, enabling the necked down condition illustrated in FIG. 44. The web, fully elongated in the machine direction, and having fluid elastomeric binder applied to its back surface, is then passed through curing oven V, where the material is stabilized to provide a hook-engageable material which is elastically stretchy in its cross-machine direction only.

Other examples of webs having one-direction stretchiness have been described earlier herein, such as pre-stretched, and stabilized knit fabric and still others are readily formed according to various patents cited above, or by modification of such fabrics and forming techniques following principles and techniques given here.

While a principal thrust of this disclosure has been the effective and easy production of elastically extensible hook and loop fastening materials, and composites which comprise bands of loop-engageable hooks and hook-engageable loop, various aspects of the invention can be employed to form advantageous flexible articles which are not substantially extensible. An example is a "zebra-like" material, of alternating bands of loop-engageable hooks and hook-engageable loops, the loop component, on which the bands of hooks are in situ laminated, being a conventional widthwise uniform inextensible loop product, for instance knit hook-engageable loop material 3905 available from Velcro, USA. One example of the use for such material is to wrap articles which themselves have a degree of resiliency, such as a bundle of electrical cables, which by the tendency of the bundle to expand, maintains the fasteners under sheer loading when wrapped about the cables as a strap or wrapping. The material, of suitably long dimension, may be folded over to form a long enclosing sleeve to provide an easily applied protective sheathe to cables, limbs, tubes, vegetables or the like. Such a sheath can also serve as a sound deadening cushion to prevent rattles, e.g. when electric cables shrouded with the material, are installed in the structure of an automobile or other vehicle. Likewise the sheathe may provide thermal insulation or abrasion protection to objects wrapped.

In the foregoing embodiments the surface upon which bands or islands of molded fastener stems have been in situ bonded has been defined by a flexible or elastically stretchy carrier sheet which has conformed to the cylindrical surface of the mold roll. This has numerous advantages, among which are protracted dwell time even when the mold roll turns rapidly. This enables the tiny molds to fill with resin and the resin to flow to form the base that bonds to the carrier, and to cool, before the point is reached at which the molded stems (and crooks, if integrally molded with the stems) are pulled from the molds. Certain broad aspects of the invention, however, are not limited to such arrangements.

Figure 45:
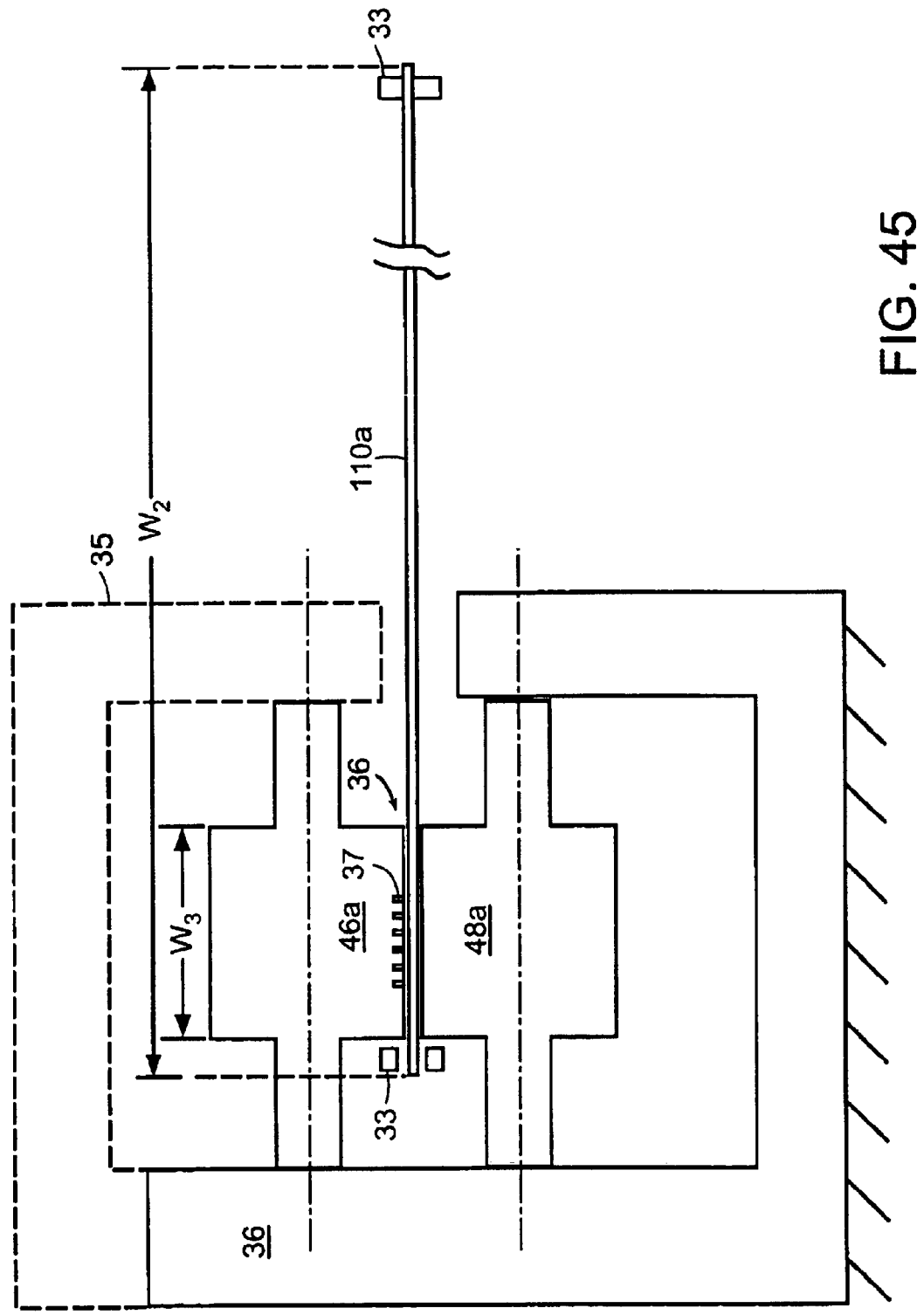
FIG. 45 is a front view of a fastener element molding apparatus of the present invention applying fastener elements to a planar sheet or work piece.
Figure 46:
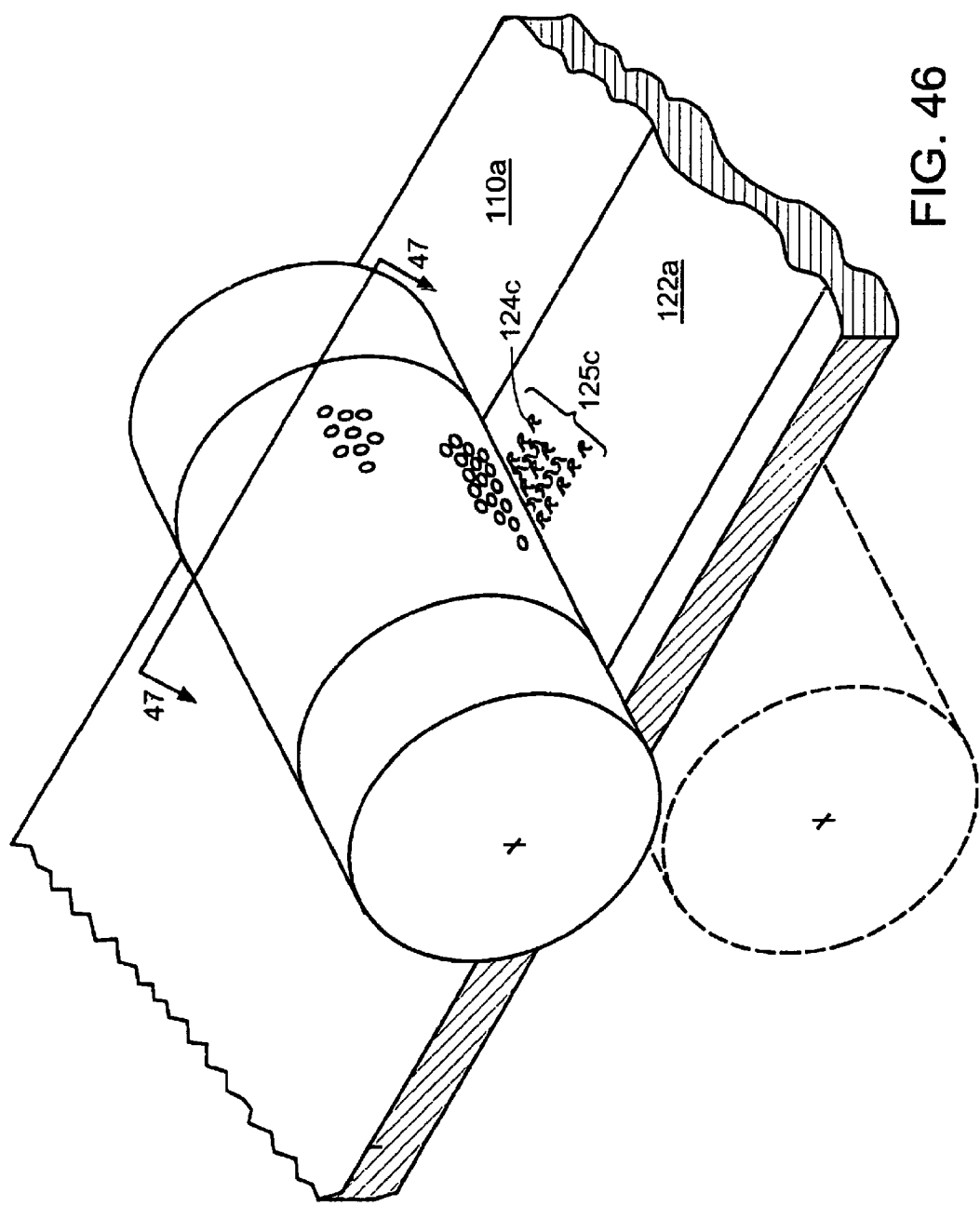
FIG. 46 is an isometric view of the apparatus of FIG. 45 illustrating only the fastener element mold roll portion of the apparatus applying engageable fastener elements to a sheet or work piece.

Referring to FIGS. 45, 46 and 47 a preformed carrier 110*a* is of planar form as it proceeds through the mold station. For instance the carrier may be a widthwise stretchable or flexible web such as a knit loop fabric, or an elastically stretchable carrier or loop material of any of the examples given above. In such cases, a tenter frame 33 maintains the carrier sheet in a width-wise flat condition or, when desired, stretched with as much as 50% or even 100% widthwise elastic extension depending upon the material of the carrier.

Under such conditions, as shown in FIG. 45, a cantilever-mounted mold roll extends inwardly form the edge of the carrier sheet or work piece to the position where a band or bands of molded fastener stems or, as shown, fully formed molded fastener hooks, are desired.

Where the band or bands of fastener stems or fully formed hooks are to be applied near the edge of the carrier, the required nip forces are sufficiently low that the rolls may be supported from one end using suitably spaced bearings of a cantilever mounting. That arrangement is suggested in the solid line diagram of the mounting of mold roll 46*a* in FIG. 45. Where the nip pressure is greater, a cantilever support 35 for the second bearing is employed, as suggested in dashed lines in the figure.

Referring to FIGS. 45 and 46, the operation of molding apparatus is illustrated with workpiece 110*a* being fed through nip 36 formed by mold roll 46*a* and pressure roll 48*a*. Mold roll 46*a* extends from frame 36 in a cantilevered fashion, e.g., supported from one side only, so that workpiece 110*a* of width, $W_2$, greater than the width, $W_3$, of mold roll 46*a* can be processed through nip 36 without interfering with frame 36. Typically mold roll 46 has width $W_3$ of less than approximately 2 ft. The cantilevered support of one or the rolls leaves an open end of nip 36 to allow workpiece of substantially greater than either roll 46*a* or 48*a* to pass through nip 36 without interfering with support frame 36. As workpiece 110*a* moves through nip 36, cavities 37 of mold roll 46 *a* are filled, as described below, with molten thermoplastic resin, e.g., polypropylene, to form engageable elements, e.g., hooks which are deposited in a relatively narrow band onto a portion of workpiece 110*a*. The initially molten thermoplastic resin adheres the base of each hook stem to workpiece 110a as the thermoplastic resin solidifies, in a in situ bonding action.

The amount of molten thermoplastic resin delivered to the mold roll determines whether the hooks will form an integral array of thermoplastic resin joined together by a thin base layer which is adhered to the surface of the preformed carrier sheet or workpiece 110a or whether the hooks will be separate from one anther, individually adhered to the carrier. For example, as shown in FIG. 4, a thin layer of thermoplastic resin forms a base layer 122a integral with the array 125c of hooks 124c.

However, by reducing the amount of thermoplastic resin delivered to the mold roll, joining base layer 122a can be eliminated so that the base of each molded fastener stem is in situ bounded carrier 110a without thermoplastic resin joining the hooks together.

Referring now to FIG. 47, an example of delivery of molten thermoplastic resin to the mold roll to form fastener elements on the workpiece will be described. Molten thermoplastic resin is delivered to mold roll 46a by extruder 42. Delivery head 42a of extruder 42 is shaped to conform with a portion of the periphery of mold roll 46a to form base layer 122a and to prevent extruded thermoplastic resin from escaping as it is forced into hook cavities 37 of rotating (counterclockwise) mold roll 46a. Rotation of mold roll 46a brings base portions of thermoplastic resin-filled cavities 37 into contact with workpiece 110a and the thermoplastic resin is forced (by pressure roll 48a (FIG. 45)) to bond to the surface of workpiece 110a. In the case of porous or fibrous carrier sheets or workpieces, the thermoplastic resin solidifies, portions which have partially penetrated the surface adhere to workpiece 110a with further rotation of mold roll 46a partially solidified molded hooks or stems are extracted from mold cavities 37 leaving a band of hooks or stems projecting from workpiece 110a. By adjusting the space between head 42a and mold roll 46, the volume of molten thermoplastic resin delivered, and the speed rotation of mold roll 46a, an amount of thermoplastic resin beyond the capacity of mold cavities can be delivered to mold roll 46a. This additional thermoplastic resin resides on the periphery of mold roll 46a and is brought into contact with workpiece 110a to form base layer 122a of thermoplastic resin from which the stems of the engaging elements 124c extend. In dashed lines, an alternative method of delivering the molten resin to the mold roll, as described previously above, is also suggested.

It will be realized that the apparatus of FIGS. 45–47 do not require that the preformed carrier be flexible. It may indeed be a rigid workpiece, for instances it may be a construction material such as preformed building siding, roofing material, or a structural member, fed through the molding station on appropriate conveyors. The apparatus of all of the embodiments may be incorporated in a manufacturing line, in which the carrier or workpiece is a perform, upon which further actions are taken other than in situ bonding of fasteners or fastener stems occurs. The manufacturing line may be, e.g., for manufacture of building siding, roof shingles or packaging sheet or film.

There are other ways to form e.g. separated parallel linear bands or discrete, disconnected islands of hooks on the above-described carrier webs within certain broad aspects of the present invention. For example, at dispersed, selected locations across the width of a traveling preformed carrier web, e.g. a material defining hook-engageable loops, discrete separate molten resin deposits of the desired form, e.g. of x, y-isolated islands, or in spaced apart parallel bands, may be deposited upon the surface structure of the carrier web. Following this, upper portions of the resin deposits, while still molten, or after being reheated by an intense localized flame line, are molded into fastener stems by mold cavities that are pressed against the resin deposits. For instance, at selected widthwise separated locations along a deposit line, as the web transits the line, discrete island-form deposits are made at selected locations. Immediately, with the resin still molten, or after heat activation, the web is introduced into a molding nip, formed by a mold roll and a pressure roll. The mold roll, for instance, defines tiny fixed hook fastener cavities as described above, or smaller fastener features, e.g. of less than 0.005 inch height, or similarly shallow cavities for tiny stem preforms, that are aligned to press down upon the resin deposits under conditions in which nip pressure causes the molten resin to enter the cavities at the base of the stem portion of the cavities, and fill the molds, and be molded into a localized dense array of stem preforms or into a localized dense array of fully formed loop-engageable molded hooks. With appropriate amounts of resin in the deposits, a base layer common to all of the molded stems of a discrete island deposit can be formed by the mold roll surface, as may be desired. The mold pressure, simultaneously with the molding, causes the resin to bond firmly to the surface structure of the preformed carrier, effecting in situ lamination, Where the preformed web has a fibrous or porous makeup, as with hook-engageable loop material, the nip pressure causes the resin to commingle with the top fibers or other structure that define the surface structure of the web, without penetrating the full depth of the web. Thus the opposite side of the carrier web can remain pristine, free of the molding resin, and, if the opposite surface of the preformed web defines a uniform surface of hook-engageable loops across the full width of the article, the effectiveness of those loops can be preserved while the molded stems or fully molded hooks are molded and in situ bonding occurs.

With such arrangements it will be understood that the regions of carrier material between the separated islands remain free of the resin from which the hooks or stem preforms are molded. Thus, in the case of elastically stretchy carrier sheet preforms, whether of plain preformed elastomer sheet, or of stretchy hook-engageable loop material, the resin-free regions enable the web to be elastically stretchy, while flexibility of the article in both orthogonal (X,Y) directions in the plane of the web is achieved. Where the preformed carrier web is a non-stretchy, but flexible material, such as a bi-directionally stabilized knit loop product having hook-engageable loops on both sides, the regions between the separated islands enable the finished article to be simply flexible in both X and Y directions in the plane of the fabric.

In certain embodiments, rather than locating discrete regions of hook cavities on the mold roll, in positions to register with a pre-arranged pattern of resin deposits, the mold roll may simply have an array of mold cavities entirely occupying the mold surface of the roll, or may have such mold cavities in narrow bands separated by enlarged spacer rings or cross-wise extending ridges, as described above.

Thus, wherever it is determined to be advantageous to have molten deposits for discrete bands or islands of hooks, the deposits will register with appropriate molding structure, defining either an array of hooks (or molded stem preforms) or subsets of such hooks and preforms separated by parting or flexure regions in one or both directions, for providing a desired degree of flexibility to the islands or bands themselves. This enables the same molding nip setup to be operable with a wide range of selectable patterns of localized deposit of the molten resin, with considerable economies in capital cost and ease of operation.

Other features and advantages of the invention will be realized from the disclosure and drawings, and are within the scope of the following claims.

What is claimed is:

1. A method of forming a fastener product, the method comprising
    providing a rotating mold roll having an outer peripheral surface upon which base layer portions of resin may form and having fixed mold cavities shaped to form loop-engageable fastener hook elements on a hook side of the product, the hook elements extending integrally from such base layer portions and having molded free end portions directed generally back toward their respective base layer portions;
    introducing spaced apart amounts of molten resin to the mold roll in a manner to fill separated groups of the mold cavities and form respective resin base layer portions at the surface of the mold roll while introducing a pre-formed, elastically stretchable sheet material to the spaced-apart amounts of resin to laminate in situ a surface of the sheet material to surfaces of the resin base layer portions opposite the hook side of the product, the base layer portions being spaced-apart from each other and the elastically stretchable sheet material extending between resin base layer portions such that the sheet material is exposed in at least one resin-free region between base layer portions to provide elastic stretchability to the fastener product;
    cooling the resin in the mold cavities to form molded fastener hook elements integrally molded with and extending from the base layer portions; and
    thereafter, by application of tension to the fastener product being formed, pulling the molded fastener hook elements, including their said molded free end portions, from the fixed mold cavities of the rotating mold roll to separate the molded fastener hook elements from the mold roll to form an elastically stretchable web product carrying separated groups of fastener hook elements.

2. The method of claim 1 in which the mold roll has its mold cavities arranged to form longitudinally continuous, transversely spaced apart bands of loop-engageable fastener hook elements, and said sheet material extending transversely between spaced apart bands of the hook elements being elastically stretchable in the transverse direction.

3. The method of claim 1 or 2 in which the pre-formed sheet material is elastically stretchable in only a direction that is transverse to the longitudinal direction.

4. The method of claim 1 in which the elastically stretchable material includes at least a textile component.

5. The method of claim 4 in which the textile component comprises a stretchable material that defines hook-engageable loops.

6. The method of claim 5 in which the material is a nonwoven material which comprises a needled batt of staple fibers which has been stretched substantially in one direction only while the batt has been allowed to neck-in in the cross machine direction, with a binder having an elastomer component stabilizing the material in said stretched state, whereby the material is substantially elastically stretchable in only one direction corresponding to the direction in which it has not been stretched during manufacture.

7. The method of claim 1 in which the resin is introduced in discrete amounts spaced apart in a machine direction to form bases in the form of isolated islands.

8. The method of claim 1 in which the molded fastener hook elements are molded to have crooks that individually point in a given respective direction.

9. The method of claim 1 in which the base layer portions comprise longitudinally continuous bands of the resin, with longitudinally continuous exposed regions of transversely elastically stretchable sheet material therebetween.

10. The method of claim 1 in which the fastener hook elements each has have a molded stem that tapers toward its free end to narrower dimension from a relatively wide width at its base.

11. The method of claim 1 in which the pre-formed sheet material is stretchable in one direction and relatively inextensible in a perpendicular direction.

12. The method of claim 1 in which the pre-formed sheet material comprises a layer of thermoplastic elastomer.

13. The method of claim 1 in which the pre-formed sheet material has at least one side which defines hook-engageable loops exposed for engagement by fastener hook elements.

14. The method of claim 13 in which the side which defines hook-engageable loops lies on the same side of the pre-formed sheet material as, and closely adjacent to, the bases of the hook elements.

15. The method of claim 1 in which the pre-formed sheet material comprises multiple layers, including a pre-formed upper layer to which the base layer portions are laminated.

16. The method of claim 15 in which the pre-formed sheet material includes a lower, elastically stretchable layer.

17. The method of claim 1 wherein the resin-free region of pre-formed sheet material is wider than the base layer portions adjoining the resin-free region.

18. The method of claim 17 wherein said resin-free region is between about two and five times wider than the adjoining base layer portions.

19. The method of claim 1 in which the mold roll defines free end portions of fastener hook elements that are oriented in opposite directions.

20. The method of claim 19 in which the opposite directions are aligned with the longitudinal direction of the sheet material.

* * * * *